US012601741B2

(12) United States Patent
Blackburn et al.

(10) Patent No.: US 12,601,741 B2
(45) Date of Patent: Apr. 14, 2026

(54) DETECTION OF BIOMARKERS FOR NON-SMALL CELL LUNG CANCER

(71) Applicants:SENGENICS SDN BHD, Kuala Lumpur (MY); NATIONAL UNIVERSITY OF SINGAPORE, Singapore (SG)

(72) Inventors: Jonathan Michael Blackburn, Singapore (SG); Arif Anwar, Kuala Lumpur (MY); Boon Cher Goh, Singapore (SG); Lingzhi Wang, Singapore (SG); Sok Hwee Esther Cheow, Singapore (SG); Ross Andrew Soo, Singapore (SG); Win Lwin Thuya, Singapore (SG)

(73) Assignees: SENGENICS SDN BHD, Kuala Lumpur (MY); NATIONAL UNIVERSITY OF SINGAPORE, Singapore (SG)

( * ) Notice: Subject to any disclaimer, the term of this patent is extended or adjusted under 35 U.S.C. 154(b) by 1024 days.

(21) Appl. No.: 17/413,474

(22) PCT Filed: Dec. 12, 2019

(86) PCT No.: PCT/SG2019/050611
§ 371 (c)(1),
(2) Date: Jun. 11, 2021

(87) PCT Pub. No.: WO2020/122817
PCT Pub. Date: Jun. 18, 2020

(65) Prior Publication Data
US 2022/0260571 A1 Aug. 18, 2022

(30) Foreign Application Priority Data
Dec. 12, 2018 (SG) ............................ 10201811119X

(51) Int. Cl.
*G01N 33/574* (2006.01)
*G01N 33/543* (2006.01)
*G01N 33/68* (2006.01)
(52) U.S. Cl.
CPC . *G01N 33/57423* (2013.01); *G01N 33/54306* (2013.01); *G01N 33/6854* (2013.01)
(58) Field of Classification Search
CPC ....... G01N 33/57423; G01N 33/54306; G01N 33/6854
See application file for complete search history.

(56) References Cited

U.S. PATENT DOCUMENTS

2006/0281122 A1 12/2006 Bryant et al.
2015/0064210 A1 3/2015 GuhaThakurta et al.
2019/0204324 A1 7/2019 Cho et al.

FOREIGN PATENT DOCUMENTS

EP         1470229 B1 * 5/2006 ............. C12N 15/62
WO   WO-2009/085237 A2   7/2009
WO   WO-2011/129483 A1   10/2011
WO   WO-2018/049025      3/2018
WO    WO-2018216009 A1   11/2018
WO   WO-2020/186101      9/2020

OTHER PUBLICATIONS

Groeper et al., "Cancer/Testis Antigens in Non-Small Cell Lung Cancer: expression and immunogenicity" Doctoral Thesis. (2006). https://edoc.unibas.ch/589/1/DissB_7889.pdf (Year: 2006).*
Zarogoulidis K, Zarogoulidis P, Darwiche K, Boutsikou E, Machairi-otis N, Tsakiridis K, Katsikogiannis N, Kougioumtzi I, Karapantzos I, Huang H, Spyratos D. Treatment of non-small cell lung cancer (NSCLC). doi: 10.3978/j.issn.2072-1439.2013.07.10. PMID: (Year: 2013).*
Yu, Bin et al. "Effects of IFN-gamma and Stat1 on gene expression, growth, and survival in non-small cell lung cancer cells." Journal of interferon & cytokine research : the official journal of the International Society for Interferon and Cytokine Research vol. 27,3 (2007): 209-20. doi:10.1089/jir (Year: 2007).*
Do, H., Wong, N., Murone, C. et al. A critical re-assessment of DNA repair gene promoter methylation in non-small cell lung carcinoma. Sci Rep 4, 4186 (2014). https://doi.org/10.1038/srep04186 (Year: 2014).*
Li, Dan et al. "Strong evidence for LncRNA ZNRD1-AS1, and its functional Cis-eQTL locus contributing more to the susceptibility of lung cancer." Oncotarget vol. 7,24 (2016): 35813-35817. doi:10. 18632/oncotarget.8411 (Year: 2016).*
Matsumoto, H. et al., Abstract 518: Immunogenicity of cancer/testis antigen XAGE-1d in patients with non-small cell cancer (NSCLC). Cancer Research, Apr. 2012, vol. 72, No. 8, Supplement [Retrieved on Feb. 24, 2020] <DOI: 10.1158/1538-7445.AM2012-518>.
X Ohue, Y. et al., Spontaneous antibody, and CD4 and CDS T-cell responses against XAGE-1 b (GAGED2a) in non-small cell lung cancer patients. International Journal of Cancer, Nov. 22, 2011, vol. 131, pp. E649-E658 [Retrieved on Feb. 24, 2020] <DOI: 10.1002/1JC.27359>.
X Tang, Z.-M. et al., Serum tumor-associated autoantibodies as diagnostic A biomarkers for lung cancer: A systematic review and meta-analysis. PLoS One, Jul. 27, 2017, vol. 12, No. 7, pp. e0182117: 1-21 [Retrieved on Feb. 24, 2020] <DOI: 10.1371/JOURNAL.PONE.0182117>.
Chapman, C.J. et al., Immuno-Biomarkers in Small Cell Lung Cancer: Potential Early Cancer Signals. Clin Cancer Res, Dec. 7, 2010, vol. 17, No. 6, pp. 1474-1480 [Retrieved on Feb. 24, 2020] <DOI: 10.1158/1078-0432.CCR-10-1363>.

(Continued)

*Primary Examiner* — Gregory S Emch
*Assistant Examiner* — Mckenzie A Dunn
(74) *Attorney, Agent, or Firm* — Harness, Dickey & Pierce, P.L.C.

(57) ABSTRACT

A method for diagnosing Non-Small Cell Lung Cancer (NSCLC) from a sample extracted from a subject by testing the sample for the presence of biomarkers, the biomarkers being autoantibodies against XAGE1D, LRRFIP2 and GAGE2C. Also claimed are a method of manufacturing a kit, and compositions comprising a panel of said antigens or exosomal autoantibodies.

19 Claims, 14 Drawing Sheets
Specification includes a Sequence Listing.

(56) References Cited

OTHER PUBLICATIONS

Jia, J. et al., Development of a Multiplex Autoantibody Test for Detection of Lung Cancer. PLoS One, Apr. 22, 2014, vol. 9, No. 4, pp. e95444: 1-10 [Retrieved on Feb. 24, 2020] <DOI: 10.1371/JOURNAL.PGNE.0095444.

International Search Report and Written Opinion of the International Searching Authority issued in PCT/SG2019/050611, mailed Feb. 25, 2020; ISA/SG (11 pages).

Jin, J. et al. "LRRFIP2 negatively regulates NLRP3 inflammasome activation in macrophages by promoting Flightless-I-mediated caspase-1 inhibition" Nature Communications, (doi: 10.1038/ncomms3075), Aug. 14, 2013.

Chinese Office Action issued Mar. 14, 2024 in corresponding Chinese Patent Application No. 201980091833.4.

Nakagawa, K. et al. "XAGE-1 Expression in Non-Small Cell Lung Cancer and Antibody Response in Patients" Clin Cancer Res 2005;11(15) Aug. 1, 2005.

Yao, Y. et al. "Potential application of non-small cell lung cancer-associated autoantibodies to early cancer diagnosis." Biochem Biophys Res Commun. Jul. 6, 2012; 423(3): 613-619.

Saito, K. et al. "Immune Responses to the Cancer Testis Antigen XAGE-1b in Non Small Cell Lung Cancer Caucasian Patients" DOI:10.1371/journal.pone.0150623 Mar. 3, 2016.

Shan, Q. et al. "A cancer/testis antigen microarray to screen autoantibody biomarkers of non-small cell lung cancer" Cancer Letters 328 (2013) 160-167.

Lai Q, Zhang L, Sun Y. [Association of XAGE-1 gene expression with clinical characteristics of lung cancer]. Zhongguo Fei Ai Za Zhi. Aug. 2010;13(8):786-9. Chinese. doi: 10.3779/j.issn.1009-3419. 2010.08.07. PMID: 20704819; PMCID: PMC6000549.

* cited by examiner

Figure 6

EcoRI - 1300 - G'AATT_C
SpeI - 1306 - A'CTAG_T
NcoI - 1316 - C'CATG_G
BssHII - 1322 - G'CGCG_C

DETECTION OF BIOMARKERS FOR NON-SMALL CELL LUNG CANCER

CROSS REFERENCE TO RELATED APPLICATIONS

This application is a U.S. National Phase Application under 35 U.S.C. 371 of International Application No. PCT/SG2019/050611 filed on Dec. 11, 2019, which claims the benefit of priority from Singapore Patent Application No. 10201811119X filed on Dec. 12, 2018. The entire disclosures of all of the above applications are incorporated herein by reference.

FIELD OF INVENTION

The invention relates to the detection of biomarkers for Non-Small Cell Lung Cancer (NSCLC).

BACKGROUND

Despite technological advances in the area of proteomics research, there are only a handful of biomarkers that have entered the clinic, and 90% of the biomarkers are protein biomarkers. Autoantibody biomarkers as described herein are autoantibodies to antigens, autoantibodies being antibodies which are produced by an individual which are directed against one or more of the individual's own proteins ('self' antigens). Some of the main reasons for failure of biomarkers to make it into clinical practice are:

1) Low sensitivity and specificity of diagnosis of cancerous diseases
2) Low prognostic/predictive value
3) Not important for clinical decision making
4) Original claims fail validation (false discoveries)

For Non-small cell Lung Cancer (NSCLC), although many individual proteins have been repotted to aid diagnosis and prognosis, very few have demonstrated sufficient value to be introduced into clinical use. Furthermore, many protein biomarkers discovered in the serum/plasma samples seem to overlap with other diseases, especially other cancels and inflammatory diseases.

An aim of the invention therefore is to provide an improved panel of autoantibody biomarkers for the detection of Non-Small Cell Lung Cancer.

SUMMARY OF INVENTION

In one aspect of the invention, there is provided a method for diagnosing Non-Small Cell Lung Cancer from a sample extracted from a subject, comprising the steps of:

(i) testing the sample for the presence of autoantibody biomarkers specific for Non-Small Cell Lung Cancer;
(ii) determining whether the subject has Non-Small Cell Lung Cancer based on the detection of said autoantibody biomarkers;

characterised in that the biomarkers are autoantibodies to antigens comprising XAGE1D, LRRFIP2 and GAGE2C.

Advantageously the autoantibody biomarkers can be used in the diagnosis of non-small cell lung cancer.

In one embodiment the sample is tested using a panel of antigens that correspond to the autoantibody biomarkers. Typically the antigens are biotinylated proteins. Advantageously the biotinylation ensures that the antigens are folded in their correct form to ensure accuracy of detection by the autoantibody biomarkers.

In one embodiment the antigens further comprise one or more of DDX53, DDX43, GAGE1, MAGEA10, ZNRD1, MAP2K5, MAGEA4, STAT1, CT47A1, IGF2BP3, CTAG2, RAD23B, FADD, PTPN20A, TPM1, CTAG1A.

It should be noted that not all antigens generate an autoantibody response and it is not possible to predict a priori which antigens will do so in a given cancer patient cohort—of more than 1600 antigens tested, only autoantibodies against the 19 antigens described above are suitable as biomarkers in NSCLC. Advantageously some of the 19 antigens are recognised by autoantibody biomarkers even when the well-known EGFR test for NSCLC is negative.

In one embodiment each biotinylated protein is formed from a Biotin Carboxyl Carrier Protein (BCCP) folding marker which is fused in-frame with the protein.

In one embodiment the biotinylated proteins are bound to a streptavidin-coated substrate Advantageously full-length proteins are expressed as fusions to the BCCP folding marker which itself becomes biotinylated in vivo when the fusion partner is correctly folded By comparison misfolded fusion partners cause the BCCP to remain in the 'apo' (i.e. non-biotinylated) form such that it cannot attach to a streptavidin substrate. Thus only correctly folded fusion proteins become attached to the streptavidin substrate via the biotin moiety appended to the BCCP tag.

In one embodiment the substrate comprises a glass slide, biochip, strip, slide, bead, microtitre plate well, surface plasmon resonance support, microfluidic device, thin film polymer base layer, hydrogel-forming polymer base layer, or any other device or technology suitable for detection of antibody-antigen binding.

In one embodiment the substrate is exposed to a sample extracted from a person, such that autoantibody biomarkers from the sample may bind to the antigens.

Typically the sample comprises any or any combination of exosomes, blood, serum, plasma, urine, saliva, amniotic fluid, cerebrospinal fluid, breast milk, semen or bile.

Advantageously as exosomes contain membrane-bound proteins that reflect their originating cell, and in cancer have been shown to be implicated in the crosstalk between tumour cells and normal cells thereby facilitating the malignant process, exosomes have been found to be promising as enriched sources of diagnostic and prognostic markers. The exosomal autoantibody biomarkers detected using the BCCP folding marker technology are therefore potentially superior compared to the majority of serological biomarkers identified using conventional approaches.

In one embodiment following exposure to the sample, the substrate is exposed to a fluorescently-tagged secondary antibody to allow the amount of any autoantibodies from the sample bound to the antigens on the panel to be determined. Typically the secondary antibody is anti-human IgG, but it will be appreciated that other secondary antibodies could be used, such as anti-IgM, anti-IgG1, anti-IgG2, anti-IgG3, anti-IgG4 or anti-IgA.

In one embodiment the presence of non-small cell lung cancer corresponds to the relative or absolute amount of autoantibodies from the sample specifically binding to the antigens.

In one embodiment the method is performed in vitro.

In a further aspect of the invention, there is provided a method for manufacturing a kit for diagnosing Non-Small Cell Lung Cancer from a sample extracted from a subject, comprising the steps of:

for each antigen in a panel, cloning a biotin carboxyl carrier protein folding marker in-frame with a gene encoding the antigen and expressing the resulting biotinylated antigen, binding the biotinylated antigens to addressable locations on one or more streptavidin-coated substrates, thereby forming an antigen array;

such that the amount of autoantibodies from the sample binding to the antigens on the panel can be determined by exposing the substrate to the sample and measuring the response;

characterised in that the antigens comprise XAGE1D, LRRFIP2 and GAGE2C.

In one embodiment the antigens further comprise one or more of DDX53, DDX43, GAGE1, MAGEA10, ZNRD1, MAP2K5, MAGEA4, STAT1, CT47A1, IGF2BP3, CTAG2, RAD23B, FADD, PTPN20A, TPM1, CTAG1A.

In one embodiment the method comprises detecting upregulation/downregulation of one or more autoantibody biomarkers. Thus the method can be used for monitoring the response of a subject undergoing chemo/targeted/immunotherapy for lung cancer and stratifying the subjects based on their autoantibody profile.

In a further aspect of the invention there is provided a method for detecting non-small cell lung cancer by exposing a composition comprising a panel of antigens as herein described to a sample extracted from a person, and determining the level of autoantibodies from tire sample binding to the antigens.

In a yet further aspect of the invention there is provided a method for diagnosing non-small cell lung cancer by exposing a composition comprising a panel of antigens as herein described to a sample extracted from a person in vitro, and determining the level of autoantibodies from the sample binding to the antigens.

In further aspect of the invention, there is provided a composition comprising a panel of antigens for detecting non-small cell lung cancer, characterised in that the antigens comprise XAGE1D, LRRF1P2 and GAGE2C.

In one embodiment the antigens further comprise one or more of DDX53, DDX43, GAGE1, MAGEA10, ZNRD1, MAP2K5, MAGEA4, STAT1, CT47A1, IGF2BP3, CTAG2, RAD23B, FADD, PTPN20A, TPM1, CTAG1A.

In one embodiment the antigens are biotinylated proteins

In one embodiment the amount of one or more exosomal autoantibody biomarkers binding in vitro to the antigens in a sample from a patient can be measured to determine the presence of non-small cell lung cancer.

In yet further aspect of the invention, there is provided a composition comprising a panel of exosomal autoantibody biomarkers for detecting non small cell long cancer.

wherein the levels of exosomal autoantibody biomarkers are measured in a sample front a NSCLC patient;

characterised in that the exosomal autoantibody biomarkers are selected from autoantibodies specific for at least X Antigen Family Member 1D (XAGE1D), LRR Binding FLII Interacting Protein 2 (LRRFIP2) and G Antigen 2C (GAGE2C).

BRIEF DESCRIPTION OF DRAWINGS

It will be convenient to further describe the present invention with respect to the accompanying drawings that illustrate possible arrangements of the invention. Other arrangements of the invention are possible, and consequently the particularity of the accompanying drawings is not to be understood as superseding the generality of the preceding description of the invention.

DETAILED DESCRIPTION

Materials and Methods

Figure 8:
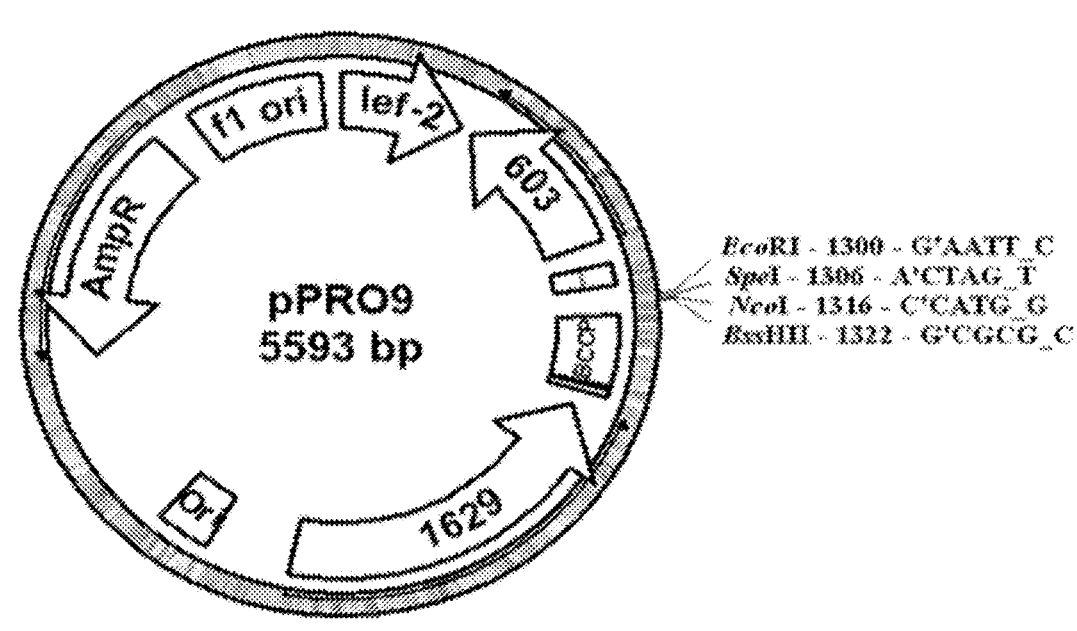
FIG. 8 illustrates the pPRO9 plasmid used as a vector.

Gene synthesis and cloning. The pPRO9 plasmid (see FIG. 8 below) was constructed by standard techniques and consists of a c-myc tag and BCCP protein domain, preceded by a multi-cloning site. A synthetic gene insert was assembled from synthetic oligonucleotides and/or PCR products. The fragment was cloned into pPRO9 using SpeI and NcoI cloning sties. The plasmid DNA was purified from transformed bacteria and concentration determined by UV spectroscopy. The final construct was verified by sequencing. The sequence congruence within the used restriction sites was 100%. 5 μg of the plasmid preparation was lyophilized for storage.

The recombinant baculoviruses are generated via co-transfection of a bacmid carrying the strong viral polyhedrin promoter together with a transfer vector carrying the coding sequences of protein of interest, into the Sf9 cell line which is a clonal isolate derived from the parental *Spodoptera frugiperda* cell line IPLB-Sf-21-AE. Homologous recombination initiated by the viral system causes the transfected cells to show signs of viral cytopathic effect (CPE) within few days of culture incubation. The most common CPE observed was the significantly enlargement of average cell size, a consequences of viral progeny propagation. These baculoviruses known as P0 were then released into the culture medium, and viral amplification were done to generate a higher titre of P1 viruses.

Protein Expression. Expressions were carried out in 24 well blocks using 3 ml cultures containing $6 \times 10^6$ Sf9 cells per well. High titre, low passage, viral stocks of recombinant baculovirus ($>10^7$ pfu/ml) were used to infect sf9 insect cells. The infected cells were then cultured for 72 hours to allow them to produce the recombinant protein of interest. The cells were washed with PBS, resuspended in buffer, and were frozen in aliquots at −80° C. ready for lysis as required. Depending on the transfer vector construct and the nature of the protein itself, recombinant protein lysate can be pelleted either from the cultured cell or the cultured medium Positive recombinant proteins were then analyzed via SDS-PAGE and Western blot against Streptavidin-HRP antibody. In total, 1630 human antigens were cloned and expressed using this methodology.

Array fabrication. HS (hydrogel-streptavidin) slides were purchased from Schott and used to print the biotinylated proteins. A total of 9 nanoliters of crude protein lysate was printed on a MS slide in quadruplicate using non-contact piezo printing technology. Print buffer that have a pH between 7.0 and 7.5 were used. The slides were dried by centrifugation (200×g for 5 min) before starting the washing and blocking. The printed arrays were blocked with solutions containing BSA or casein (concentration: 0.1 mg/ml) in a phosphate buffer. The pH was adjusted to be between 7.0 and 7.5 and cold solutions were used (4° C.-20° C.). Slides were not allowed to dry between washes, and were protected from light. In total, each resultant 'Immunome array' comprised 1630 antigens, each printed in quadruplicate.

Experimental Procedure. Each critical experimental step of running the Immunome array required a second trained person to thoroughly check, precisely record and cross-check all steps in the protocol, in order to reduce operator bias. Samples were picked, randomised and assigned to assay racks accordingly. These samples were then stored at −20° C. until the experimental setup was complete.

1. Study Cohort

A cohort comprising of 209 participants between the age of 29 and 85 was recruited for the study. The subjects were selected across more than 6 ethnicities diagnosed with different types of lung cancer including adenocarcinoma, squamous cell carcinoma, non-small cell lung carcinoma, large cell carcinoma and other types of lung malignancies. A total of 31 patients were diagnosed with early stage lung cancer while 78 patients were diagnosed with late stage lung cancer. A total of 33 subjects were smoker and 44 subjects were non-smoker. EGFR was tested positive in 30 subjects and negative in 39 subjects. A total of 100 samples from age and gender-matched healthy subjects were also collected.

2. Sample Preparation

A total of 209 plasma samples were collected from the above cohort and exosomes were isolated from each sample using an Invitrogen Total Exosome Isolation kit (Thermo Fisher cat no. 4484450). Exosomal preparations were frozen at −20° C. until use.

Exosome samples were placed in a shaking incubator set at 20° C. and allowed to thaw for 30 minutes. When completely thawed, each sample was vortexed vigorously three times at full speed and spun down for 3 minutes at 13,000 rpm using a microcentrifuge. 22.5 μL of the sample was pipetted into 4.5 mL of Serum Assay Buffer (SAB) containing 0.1% v/v Triton, 0.1% w/w BSA in PBS (20° C.) and vortexed to mix three times. The tube was tilted during aspiration to ensure that the plasma was sampled from below the lipid layer at the top but does not touch the bottom of the tube in case of presence of any sediment. This exosome dilution process was carried out in a class II biological safety cabinet. Batch records were marked accordingly to ensure that the correct samples were added to the correct tubes.

Other types of samples, such as serum, plasma, blood, urine, saliva, amniotic fluid, cerebrospinal fluid, breast milk, semen or bile were diluted as per the above protocol before assay.

3. Biomarker Assay

Each protein microarray was removed from the storage buffer using forceps, placed in the slide box and rack containing 200 mL cold SAB and shaken on an orbital shaker at 50 rpm, for 5 minutes. After washing, each protein microarray was placed, array side up, in a slide hybridization chamber with individual plasma which had been diluted earlier. All slides were scanned using the barcode scanner into the relevant batch record and incubated on a horizontal shaker at 50 rpm for 2 hours at 20° C.

4. Array Washing After Plasma Binding

The protein microarray slide was then rinsed twice in individual "Pap jars" with 30 mL SAB, followed by 200 mL of SAB buffer in the slide staining box for 20 minutes on the shaker at 50 rpm at room temperature. All slides were transferred sequentially and in the same orientation.

5. Incubation with Cy3-anti IgG

Binding of autoantibodies to the arrayed antigens on replica Immunome arrays was detected by incubation with Cy3-rabbit anti-human IgG (Dako Cytomation) labelled according to the manufacturer's recommended protocols (GE Healthcare). Arrays were immersed in hybridization solution containing a mixture of Cy3-rabbit antihuman IgG solution (diluted 1:1000 in SAB buffer) and shaken for 2 hours at 50 rpm at 20° C.

6. Washing After Incubation with Cy3-anti IgG

After incubation, each slide was washed in 200 mL of SAB buffer, 3 times for 5 minutes, with shaking at 50 rpm at room temperature. Excess buffer was removed by immersing the slide in 200 mL of pure water for a few minutes. Slides were then dried for 2 min at 240 g at room temperature. Slides were then stored at room temperature until scanning (preferably the same day). Hybridization signals were measured with a microarray laser scanner (Agilent Scanner) at 10 μm resolution. Fluorescence intensities were detected according to the manufacturer's instructions, whereby each spot is plotted using Agilent Feature Extraction software.

Spot segmentation Semi-automatic QC process was carried out in order to produce a viable result. The output from the microarray scanner is a raw tiff format image file. Extraction and quantification of each spot on the array were performed using the GenePix Pro 7 software (Molecular Devices). A GAL (GenePix Array List) file for the array was generated to aid with image analysis. GenePix Pro 7 allows for automatic spot gridding and alignment of each spot on the array for data extraction Following data extraction, a GenePix Results (GPR) file was generated for each slide which contains numerical information for each spot; Protein ID, protein name, foreground intensities, background intensities etc.

Bioinformatics Analysis

Image Analysis: Raw Data Extraction

The aim of an image analysis is to evaluate the amount of autoantibody present in the plasma sample by measuring the median intensities of all the pixels within each probed spot. A raw tiff formal image file is generated for each slide, i.e. each sample. Automatic extraction and quantification of each spot on the array are performed using the GenePix Pro 7 software (Molecular Devices) which outputs the statistics for each probed spot on the array. This includes the mean and median of the pixel intensities within a spot along with its local background. A GAL (GenePix Array List) file for the array is generated to aid with image analysis. This file contains the information of all probed spots and their positions on the array. Following data extraction, a GenePix Results (.GPR) file is generated for each slide which contains the information for each spot; Protein ID, protein name, foreground intensities, background intensities etc. In the data sheet generated from the experiment, both foreground and background intensities of each spot are represented in relative fluorescence units (RFUs).

Data Handling and Pre-Processing

For each slide, proteins and control probes are spotted in quadruplicate—4 arrays on each slide. The following steps were performed to verify the quality of the protein array data before proceeding with data analysis.

Step 1

Calculate net intensities for each spot by subtracting background signal intensities from the foreground signal intensities of each spot. For each spot, the background signal intensity was calculated using a circular region with three times the diameter of the spot, centered on the spot.

Step 2

Remove replica spots with RFU≤0.

Step 3

Zero net intensities if only 1 replica spot remaining.

Step 4

Calculating percentage of coefficient of variant (CV %) of to determine the variations between the replica spots on each slide.

$$CV \% = \frac{S.\,D.}{\text{Mean}} \times 100\% \qquad \text{Equation 1}$$

Flag a set of replica spots with only 2 or less replica/s remaining and CV %>20% as "High CV". The mean RFU of these replica spots (i.e. proteins) will be excluded from the downstream analysis.

For proteins/controls with a CV %>20% and with 3 or more replica spots remaining, the replica spots which result in this high CV % value were filtered out. This was done by calculating the standard deviation between the median value of the net intensities and individual net intensities for each set of replica spots. The spot with the highest standard deviation was removed. CV % values were re-calculated and the process repeated.

Step 5

Calculating the mean of the net intensities for the remaining replica spots.

Step 6

Inspecting signal intensities of two positive controls: IgG and Cy3-BSA.

Step 7

Composite normalisation of data using both quantile-based and total intensity-based modules. This method assumes that different samples share a common underlying distribution of their control probes while taking into account the potential existence of flagged spots within them. The Immunome array uses Cy3-labelled biotinylated BSA (Cy3-BSA) replicates as the positive control spots across slides. Hence it is considered as a housekeeping probe for normalisation of signal intensities for any given study.

The quantile module adopts the algorithm described by Bolstad et al., 2003. This reorganisation enables the detection and handling of outliers or flagged spots in any of the Cy3BSA control probes. A total intensity-based module was then implemented to obtain a scaling factor for each sample. This method assumes that post-normalisation, the positive controls should have a common total intensity value across all samples. This composite method aims to normalise the protein array data from variations in their measurements whilst preserving the targeted biological activity across samples. The steps are as follows:

Quantile-Based Normalisation of all cy3BSA across all samples (i=spot number and j=sample number)
1. Load all Cy3-BSA across all samples, j, into an i X j matrix X
2. Sort spot intensities in each column j of X to get $X_{sort}$
3. Take the mean across each row i of $X_{sort}$ to get $<X_i>$

Intensity-Based Normalisation

1. Calculate sum of the mean across each row i, $\Sigma <Xi>$
2. for each sample, k, calculate the sum of all Cy3-BSA controls, $\Sigma Xk$
3. For each sample, k, $$\text{Scaling factor } (k) = \frac{\Sigma < Xi >}{\Sigma Xk} \qquad \text{Equation 2}$$

Data Analysis

High concentrations of art arrayed protein may occasionally give a "false" positive signal in serology assays because of concentration-driven, non-selective binding of an immunoglobulin to the target. This can arise theoretically due to an avidity effect: weak, non-specific immunoglobulin binding sites on a specific protein becoming coupled across multiple neighbouring protein molecules via an antibody as a result of the high density of immobilized protein, thus making the protein appear to be highly antigenic. Whenever this phenomenon occurs, it would be expected to be observed in the healthy control samples and will give rise to high intensity signals and/or signals that are close to saturation on the arrays. In Sengenics Immunome, proteins such as RBPJ and IGHG1 show consistently high signal intensities across all samples.

For this reason, given a large sample number (i.e. 100-200 samples) and availability of sample cohort, a penetrance-based fold change (pFC) analysis method is implemented for the identification of highly expressed proteins in each case sample. This method will remove any false positive signals from the data by setting a protein-specific threshold (i.e. background threshold). This defined per-protein background threshold is calculated based on the signal intensities for each specific protein measured for a given cohort of healthy control samples. A step-by-step description of this method is as follows:

Step 1

Individual fold changes for both case and control are calculated by dividing the RFU value for each protein in each sample, H, by the mean of the RFU values of each protein across all the control samples (i.e. background threshold).

$$\text{Individual } FC = \frac{H_{Case\ or\ Control}}{\mu(H_{Control})} \qquad \text{Equation 3}$$

Step 2

For proteins with individual fold change of less than 2 fold above the background threshold, their signal intensities (RFU) are replaced with zeroes.

Step 3

Penetrance frequency (number of ease and control samples with individual fold changes ≥2 fold) for both case (Frequency$_{Case}$) and control (Frequency$_{Control}$) are determined for each protein along with their difference.

$$\text{Frequency}_{Case} = n(\text{Individual FC (Case)} \geq 2) \qquad \text{Equation 4}$$

$$\text{Frequency}_{Control} = n(\text{Individual FC (Control)} \geq 2) \qquad \text{Equation 5}$$

$$\text{Frequency}_{diff} = \text{Frequency}_{Case} - \text{Frequency}_{Control} \qquad \text{Equation 6}$$

Step 4

Penetrance Fold Changes for both case and control groups are calculated for each protein.

$$\text{Penetrance Fold Change}_{case} = \frac{\mu(H_{Case}[i])}{\mu(H_{Control})} \qquad \text{Equation 7}$$

$$\text{Penetrance Fold Change}_{control} = \frac{\mu(H_{Control}[i])}{\mu(H_{Control})} \qquad \text{Equation 8}$$

$H_{Case}[i] = H_{Case}$ with $FC$ Case ≥ 2 fold $H_{Control}[i] = H_{Control}$ with $FC$ Control ≥ 2 fold Putative biomarkers are identified and ranked according to the following criteria.

1. Penetrance Fold Change$_{Case} \geq 2$
2. % Frequency$_{Case} \geq 10\%$

% Frequency differential ≥ 10%

Figure 1:
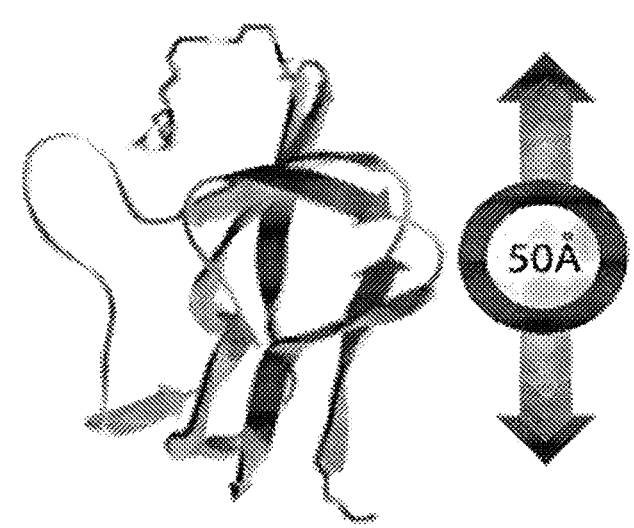
FIG. 1 illustrates the structure of the *E. coli* Biotin Carboxyl Carrier Protein domain.

The invention utilises the Biotin Carboxyl Carrier Protein (BCCP) folding marker which is cloned in-frame with the gene encoding the protein of interest, as described above and in EP1470229. The structure of the *E. coli* BCCP domain is illustrated in FIG. 1, wherein residues 77-156 are drawn (coordinate file lbdo) showing the N- and C-termini and the single biotin moiety that is attached to lysine 122 in vivo by biotin ligase.

BCCP acts not only as a protein folding marker but also as a protein solubility enhancer. BCCP can be fused to either the N- or C-terminal of a protein of interest Full length proteins are expressed as fusions to the BCCP folding marker which becomes biotinylated in vivo, but only when the protein is correctly folded. Conversely, misfolded proteins drive the misfolding of BCCP such that it is unable to become biotinylated by host biotin ligases. Hence, misfolded proteins are unable to specifically attach to a streptavidin-coated solid support. Therefore only correctly folded proteins become attached to a solid support via the BCCP tag.

The surface chemistry of the support is designed carefully and may use a three-dimensional thin film polymer base layer (polyethylene glycol; PEG), which retains protein spot morphologies and ensures consistent spot sizes across the array. The PEG layer inhibits non-specific binding, therefore reducing the high background observed using other platforms. The solid support used to immobilize the selected biomarkers is thus designed to resist non-specific macromolecule adsorption and give excellent signal-to-noise ratios and low limits of detection (i.e. improved sensitivity) by minimising non-specific background binding. In addition the PEG layer also preserves the folded structure and functionality of arrayed proteins and protein complexes post-immobilisation. This is critical for the accurate diagnosis because human serum antibodies are known in general to bind non-specifically to exposed hydrophobic surfaces on unfolded proteins, thus giving rise to false positives in serological assays on arrays of unfolded proteins, moreover, human autoantibodies typically bind to discontinuous epitopes, so serological assays on arrays of unfolded proteins or mis-folded proteins will also give rise to false negatives in autoantibody binding assays.

As biotinylated proteins bound to a streptavidin-coated surface show negligible dissociation, this interaction therefore provides a superior means for tethering proteins to a planar surface and is ideal for applications such as protein arrays, SPR and bead-based assays. The use of a compact, folded, biotinylated, 80 residue domain BCCP affords two significant advantages over for example the AviTag and intein-based tag. First, the BCCP domain is cross-recognised by eukaryotic biotin ligases enabling it to be biotinylated efficiently in yeast, insect, and mammalian cells without the need to co-express the *E. coli* biotin ligase. Second, the N- and C-termini of BCCP are physically separated from the site of biotinylation by 50 Å (as shown in FIG. 1), so the BCCP domain can be thought of as a stalk which presents the recombinant proteins away from the solid support surface, thus minimising any deleterious effects due to immobilisation.

The success rate of BCCP folding marker mediated expression of even the most complex proteins is in excess of 98%. The technology can therefore be applied in a highly parallelised pipeline resulting in high-throughput, highly consistent production of functionally validated proteins.

The addition of BCCP permits the monitoring of fusion protein folding by measuring the extent of in vivo biotinylation. This can be measured by standard blotting procedures, using SDS-PAGE or in situ colony lysis and transfer of samples to a membrane, followed by detection of biotinylated proteins using a streptavidin conjugate such as streptavidin-horseradish peroxidase. Additionally, the fact that the BCCP domain is biotinylated in vivo is particularly useful when multiplexing protein purification for fabrication of protein arrays since the proteins can be simultaneously purified from cellular lysates and immobilised in a single step via the high affinity and specificity exhibited by a streptavidin surface.

The biomarkers of the present invention can be used in early diagnosis of NSCLC, patient stratification and treatment monitoring. This includes any distinguishable manifestation of the condition, including not having NSCLC. The test can determine the presence or absence of NSCLC in a patient, the risk of developing NSCLC, the stage or severity of NSCLC and the effectiveness or response to treatment of NSCLC. Based on this status, further medical procedures may be indicated, including additional diagnostic tests or therapeutic procedures or regimens.

The microarray prototype and final product can be multiplexed far beyond the technical capability of other immunoassay systems and will enable exquisitely sensitive and specific testing of patients and high-risk population for NSCLC.

The power of a diagnostic test to correctly predict status is commonly measured as the sensitivity and specificity of the assay or the area under a receiver operated characteristic ("ROC") curve. Sensitivity is the percentage of true positives that are correctly predicted to be positive, while specificity is the percentage of true negatives that are correctly predicted to be negative. The greater the area under the ROC curve, the higher the prediction power of the test.

Autoantibody biomarkers were determined by Penetrance fold change method where age matched controls are considered as baseline to observe the elevated frequencies (≥2 Foldchange) of individual biomarkers in lung cancer patients. The list of the biomarkers identified here for diagnosis of NSCLC is shown in Table 1.

TABLE 1

| Protein | Pene-trance Fre-quency (NSCLC) | Pene-trance Fre-quency % (NSCLC) | Mean Pene-trance (NSCLC) | Pene-trance Fold Change (NSCLC) | Pene-trance Fre-quency (Con-trol) | Pene-trance Fre-quency % (Con-trol) | Mean Pene-trance (Con-trol) | Pene-trance Fold Change (Control) | Fre-quency Differ-ential | Fre-quency % Differ-ential | Pene-trance Fold Change Differ-ential | Mean (Con-trol) |
|---|---|---|---|---|---|---|---|---|---|---|---|---|
| XAGE1D | 26 | 23.85321 | 24654.94 | 9.678011 | 4 | 4 | 10338.27 | 4.058168 | 22 | 19.85321 | 5.619843 | 2547.522 |
| PTPN20A | 17 | 15.59633 | 12505.05 | 3.883074 | 4 | 4 | 12011.96 | 3.729957 | 13 | 11.59633 | 0.153117 | 3220.401 |
| TPM1 | 15 | 13.76147 | 16940.47 | 2.845931 | 6 | 6 | 25399.96 | 4.267092 | 9 | 7.761468 | −1.42116 | 5952.523 |
| CTAG1A | 14 | 12.84404 | 23341.53 | 10.43956 | 4 | 4 | 10141.22 | 4.535687 | 10 | 8.844037 | 5.903878 | 2235.872 |
| RAD23B | 14 | 12.84404 | 8193.595 | 3.231442 | 5 | 5 | 9467.406 | 3.733816 | 9 | 7.844037 | −0.50237 | 2535.585 |
| ZNRD1 | 14 | 12.84404 | 12647.16 | 2.988961 | 4 | 4 | 12658.28 | 2.991589 | 10 | 8.844037 | −0.00263 | 4231.29 |
| CTAG2 | 13 | 11.92661 | 20739.05 | 8.484654 | 5 | 5 | 10221.57 | 4.181798 | 8 | 6.926606 | 4.302857 | 2444.301 |
| LRRFIP2 | 13 | 11.92661 | 16271.97 | 3.374414 | 9 | 9 | 11729.15 | 2.432342 | 4 | 2.926606 | 0.942072 | 4822.161 |
| MAGEA10 | 13 | 11.92661 | 7393.198 | 3.156872 | 5 | 5 | 7423.496 | 3.169809 | 8 | 6.926606 | −0.01294 | 2341.938 |
| STAT1 | 13 | 11.92661 | 21774.47 | 5.037478 | 9 | 9 | 11512.56 | 2.663407 | 4 | 2.926606 | 2.374071 | 4322.495 |
| DDX43 | 12 | 11.00917 | 10360.57 | 4.337159 | 2 | 2 | 8368.541 | 3.503251 | 10 | 9.009174 | 0.833908 | 2388.793 |
| GAGE1 | 12 | 11.00917 | 12540.95 | 5.515388 | 2 | 2 | 7578.361 | 3.33289 | 10 | 9.009174 | 2.182498 | 2273.81 |
| GAGE2C | 12 | 11.00917 | 11572.43 | 5.342098 | 3 | 3 | 7604.188 | 3.510266 | 9 | 8.009174 | 1.831832 | 2166.271 |
| MAGEA4 | 12 | 11.00917 | 9790.552 | 4.88818 | 3 | 3 | 7559.253 | 3.774148 | 9 | 8.009174 | 1.114032 | 2002.903 |
| MAP2K5 | 11 | 10.09174 | 10511.43 | 3.676394 | 2 | 2 | 6913.192 | 2.417902 | 9 | 8.091743 | 1.258492 | 2859.17 |
| FADD | 10 | 9.174312 | 18237.53 | 5.423004 | 6 | 6 | 11120.35 | 3.306683 | 4 | 3.174312 | 2.116321 | 3362.994 |
| IGF2BP3 | 9 | 8.256881 | 14223.89 | 6.351528 | 2 | 2 | 6903.872 | 3.082851 | 7 | 6.256881 | 3.268677 | 2239.444 |
| CT47A1 | 8 | 7.33945 | 15453.54 | 6.885753 | 6 | 6 | 9374.437 | 4.177039 | 2 | 1.33945 | 2.708714 | 2244.278 |
| DDX53 | 7 | 6.422018 | 30847.36 | 11.16542 | 4 | 4 | 17135.53 | 6.202328 | 3 | 2.422018 | 4.963095 | 2762.758 |

Figure 2:
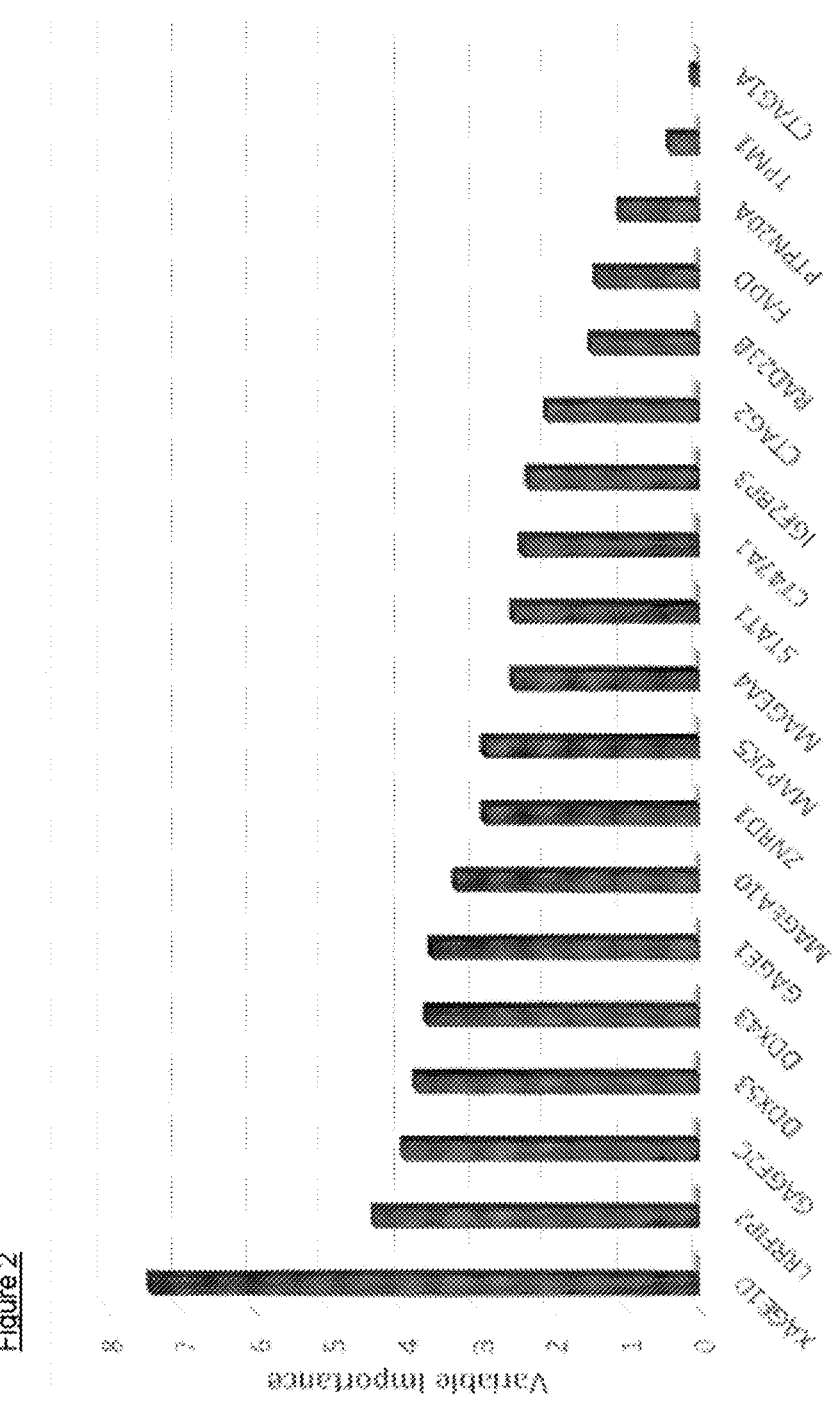
FIG. 2 is a graph illustrating variable importance scores across 19 biomarkers identified from the NSCLC study.

To evaluate the sensitivity of individual biomarkers towards lung cancer, ROC and area under the curve (AUC), 95% confidence intervals and also likelihood ratios were calculated, as set out in Table 2 Variable ranking was performed by using all combination of 19 biomarkers as separate panels and each panel was subjected to recursive feature elimination by generating random forests. The biomarkers were ranked based on random forest estimated variable importance measure derived from each panel (see FIG. 2). Mean variable importance scores determine three core set of biomarkers which are common across all biomarker panels, i.e. XAGE1D, LRRFIP2 and GAGE2C.

TABLE 2

| Protein | AUC | Confidence Interval (95% CI) | Likelihood Ratio LR-Positive | Likelihood Ratio LR-Negative | Variable Impor-tance | Rank based on Importance |
|---|---|---|---|---|---|---|
| XAGE1D | 0.696 | [0.622-0.77] | 7.75 | 0.593 | 7.39 | 1 |
| LRRFIP2 | 0.56 | [0.48-0.641] | 3.068 | 0.735 | 4.37 | 2 |
| GAGE2C | 0.612 | [0.534-0.691] | 13.321 | 0.713 | 3.98 | 3 |
| DDX53 | 0.635 | [0.557-0.714] | 3.229 | 0.614 | 3.81 | 4 |
| DDX43 | 0.641 | [0.564-0.719] | 2.601 | 0.588 | 3.67 | 5 |
| GAGE1 | 0.638 | [0.562-0.715] | 4.239 | 0.676 | 3.61 | 6 |
| MAGEA10 | 0.651 | [0.574-0.728] | 3.817 | 0.598 | 3.28 | 7 |

TABLE 2-continued

| Protein | AUC | Confidence Interval (95% CI) | Likelihood Ratio LR-Positive | LR-Negative | Variable Impor-tance | Rank based on Importance |
|---|---|---|---|---|---|---|
| ZNRD1 | 0.573 | [0.493-0.653] | 1.462 | 0.665 | 2.9 | 8 |
| MAP2K5 | 0.65 | [0.573-0.726] | 4.037 | 0.654 | 2.9 | 9 |
| MAGEA4 | 0.654 | [0.577-0.73] | 3.176 | 0.553 | 2.5 | 10 |
| STAT1 | 0.554 | [0.472-0.635] | 2.745 | 0.776 | 2.5 | 11 |
| CT47A1 | 0.623 | [0.544-0.702] | 2.382 | 0.594 | 2.39 | 12 |
| IGF2BP3 | 0.621 | [0.542-0.699] | 2.295 | 0.644 | 2.3 | 13 |
| CTAG2 | 0.619 | [0.54-0.698] | 2.637 | 0.664 | 2.04 | 14 |
| RAD23B | 0.59 | [0.51-0.67] | 2.758 | 0.722 | 1.45 | 15 |
| FADD | 0.602 | [0.522-0.681] | 3.633 | 0.737 | 1.38 | 16 |
| PTPN20A | 0.605 | [0.525-0.684] | 2.327 | 0.682 | 1.08 | 17 |
| TPM1 | 0.607 | [0.527-0.686] | 2.22 | 0.641 | 0.4 | 18 |
| CTAG1A | 0.625 | [0.547-0.703] | 2.653 | 0.687 | 0.08 | 19 |

A total of 19 potential autoantibody biomarkers have been identified for diagnosis of NSCLC; namely XAGE1D, PTPN20A, TPM1, CTAG1A, RAD23B, ZNRD1, LRRFIP2, STAT1, MAGEA10, CTAG2, GAGE1, GAGE2C, DDX43, MAGEA4, MAP2K5, FADD, IGF2BP3, CT47A1, DDX53. The Uniprot IDs, description, nucleotide sequence and protein sequence are set out in Table 5 below.

The Immunome array contains >1630 antigens, presented on the array surface in a folded, functional form, as described above Notably, it would not have been obvious a priori which specific 19 antigens out of the collection of >1630 antigens that were tested would give rise to a measurable autoantibody response that is diagnostic for NSCLC.

In this panel of 19 antigens that correspond to the 19 autoantibody biomarkers, CTAG2 is observed in 25-50% of tumor samples of melanomas, non-small-cell lung carcinomas, bladder, prostate and head and neck cancers CTAG1A is a tumor cell antigen found in various types of cancers, which makes it a good candidate for a cancer vaccine.

ZNRD1 contains two potential zinc-binding motifs and may play a role in regulation of cell proliferation. The encoded protein may be involved in cancer and human immunodeficiency virus progression.

XAGE1D and MAGEA4 RNA markers have been considered for use in screening of lung neoplasia for detecting presence of lung cancer. In normal tissues, XAGE1D is highly expressed in testis, highly expressed in breast cancer, prostate cancer and many types of lung cancers, including squamous cell carcinoma, small cell carcinoma, non-small cell carcinoma, and adenocarcinoma, as well as in Ewings cell lines, in some Ewings sarcoma patient samples, and in one of one alveolar rhabdomyosarcoma patient sample. MAGEA4 is expressed in many tumors of several types, such as melanoma, head and neck squamous cell carcinoma, lung carcinoma and breast carcinoma, but not in normal tissues except for testes and placenta.

LRRFIP2 is involved in the Wnt signalling pathway and aberrant Wnt signalling underlies a wide range of pathologies in humans. It has been suggested that the Wnt signalling pathway has important functions in stem cell biology, cardiac development and differentiation, angiogenesis, cardiac hypertrophy, cardiac failure and ageing (Rao & Kuhl, 2010). GAGE2C belongs to a family of genes that are expressed in a variety of tumors but not in normal tissues, except for the testis.

PTPN20A is present in many cell lines (at protein level) and is widely expressed. TPM1 is detected in primary breast cancer tissues but undetectable in normal breast tissues in Sudanese patients. Isoform 1 is expressed in adult and fetal skeletal muscle and cardiac tissues, with higher expression levels in the cardiac tissues Isoform 10 is expressed in adult and fetal cardiac tissues, but not in skeletal muscle.

DDX53, STAT1 and FADD expression levels were elevated in late stage group. DDX53 is a cancer-testis antigen that shows wide expression in many tumours. DDX53 has been reported to interact with EGFR and bind to the promoter sequences of EGFR. Signal transducer and activator of transcription (STAT) 1 is part of the (JAK)/STAT signalling cascade and is best known for its essential role in mediating responses to all types of interferons (IFN). A correlation of STAT1 protein expression levels with poor prognosis, increased invasive and metastatic potential has been reported in three breast cancer studies (Meissl et al., 2017). It was concluded that STAT1 can promote tumour progression, and therefore, it can be a potential marker or indicator of cancer progression (Meissl et al., 2017). Phosphorylation of FADD promotes KRAS induced lung cancer (Bowman et al. 2015). Fas-associated death domain protein (FADD) is the key adaptor molecule transmitting the apoptotic signal delivered by death receptors. It was also reported that the release of FADD by human NSCLC correlates positively with both tumour progression and aggressiveness and could be a new marker of poor prognosis (Cimino et al. 2012).

Cancer-testis antigens are a family of >1000 highly developmentally restricted fetal proteins (Wang et al., 2016; Silva et al., 2017) that are silenced in all somatic tissues except the testes and occasionally placenta, but which can be aberrantly expressed in cancerous tissues, thereby driving an autoantibody response. The Immunome array contains 202 cancer-testis antigens, presented on the array surface in a folded, functional form as described above. Notably, the 19 autoantibody biomarkers of non-small cell lung cancer identified here are significantly enriched for cancer-testis antigens, yet it would not have been obvious a priori which specific 10 cancer-testis antigens out of the collection of 202 that were tested would give rise to a measurable autoantibody response that is diagnostic for NSCLC.

The best method to verify a lung cancer diagnosis involves a multiple biomarker approach rather than a single biomarker approach.

Figure 3:
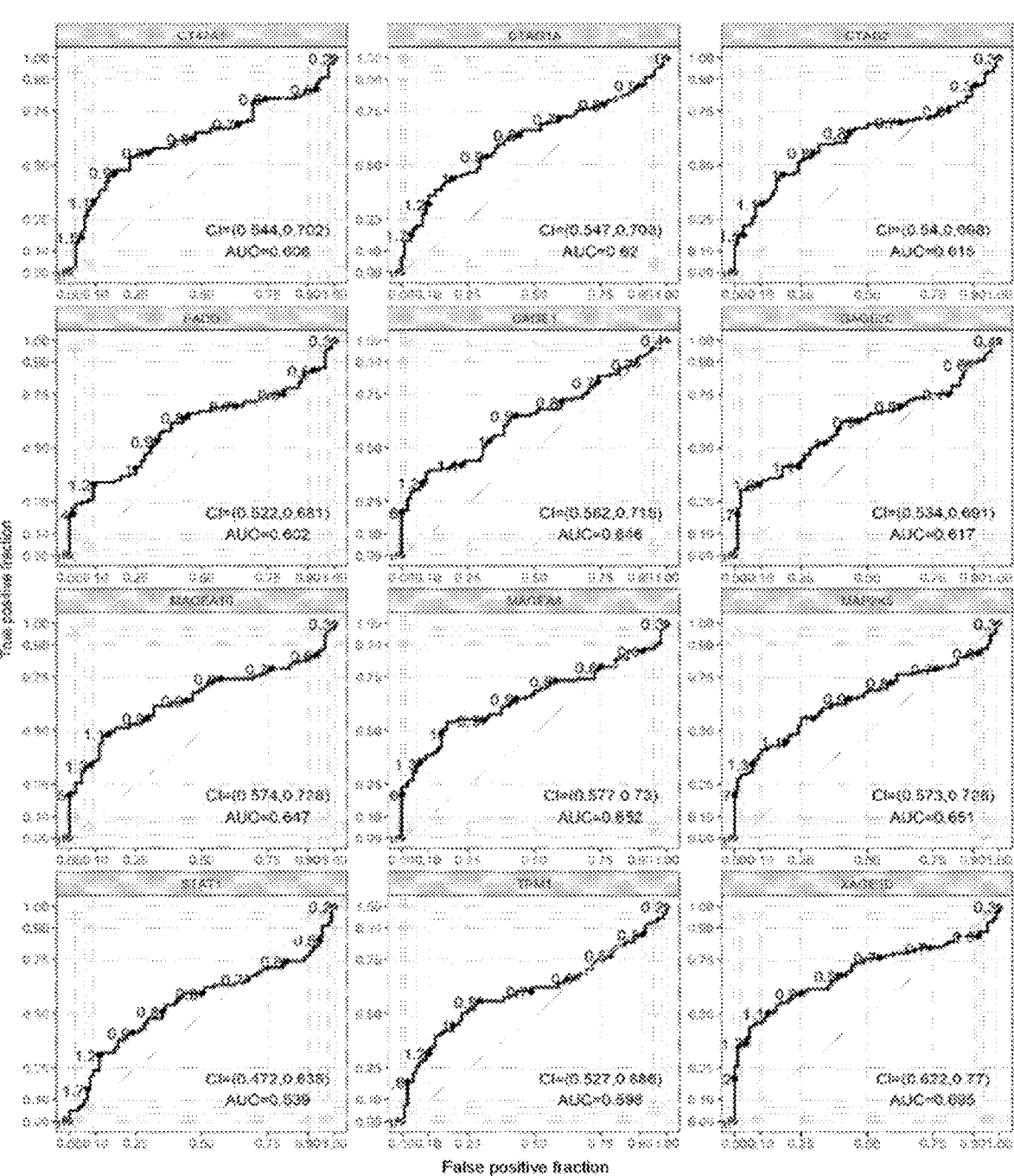
FIG. 3 illustrates ROC curves for 19 biomarkers.
Figure 3:
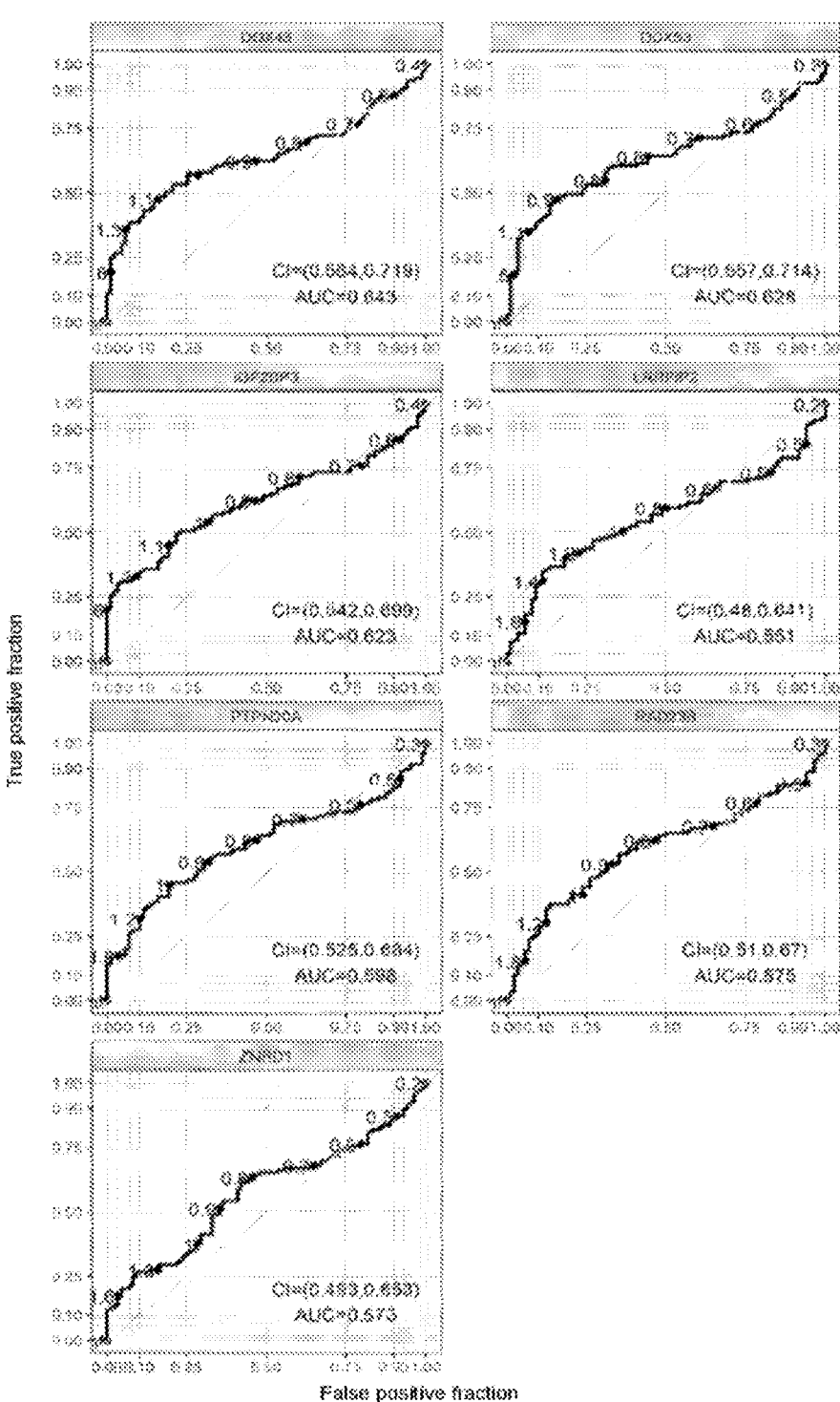
Figure 9:
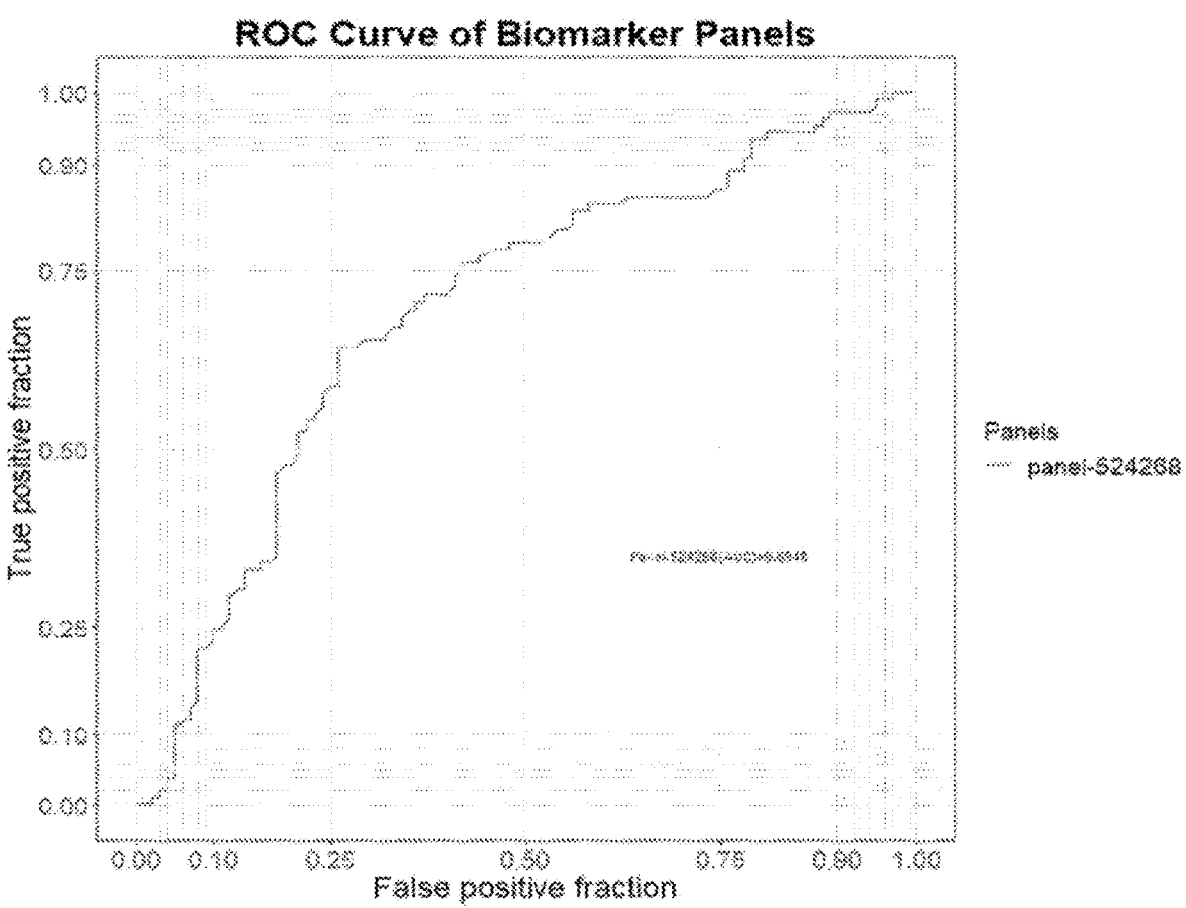
FIG. 9 illustrates the ROC curve for the 19 shortlisted biomarkers for NSCLC (XAGE1D, DDX53, GAGE2C, LRRFIP2, GAGE, DDX43, MAGEA10, ZNRD1, STAT1, MAP2K5, MAGEA4, IGF2BP3, FADD, RAD23B, CT47A1, CTAG2, PTPN20A, TPM1, CTAG1A).

As illustrated in FIG. 3, Receiver operating characteristic (ROC) curves were calculated based on individual fold changes for 19 biomarkers to show sensitivity of biomarkers towards lung cancer patients. Area under curve (AUC), 95% confidence intervals (CI) and Optimal cutoff of individual fold change (Cutoff (IFC) for each were calculated based on the method described in López-Ratón et al., (2014) using "OptimalCutpoints" R package. CI and Optimal cut-off values help to determine diagnostic ability of the biomarkers by showing positive or negative test results with lung cancer patients. The ROC curve for the panel of 19 biomarkers is illustrated in FIG. 9.

Figure 4:
FIG. 4 is a graph illustrating levels of the autoantibody biomarkers at different stages of NSCLC.

FIG. 4 shows the autoantibody biomarkers determined by Penetrance fold change (pFC) method where age matched controls are considered as baseline to observe the elevated frequencies ($\geq$2 Foldchange) of individual biomarkers in lung, cancer patients. The data was generated from profiling of Normalised RFU values of 19 biomarkers (Table 6) identified by pFC method across healthy controls (Ctrl). Early stage lung cancer patients (Early) and Late stage lung cancer patients (Late).

Figure 5:
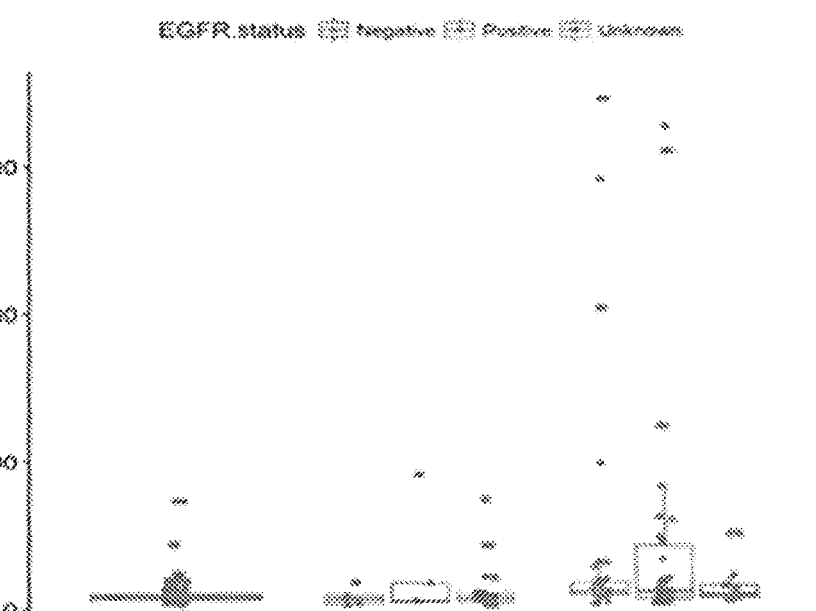
FIG. 5 illustrates a comparison of the levels of the core biomarker panel (XAGE1D, LRRFIP2 and GAGE2C) with respect to EGFR status in patients.
Figure 5:
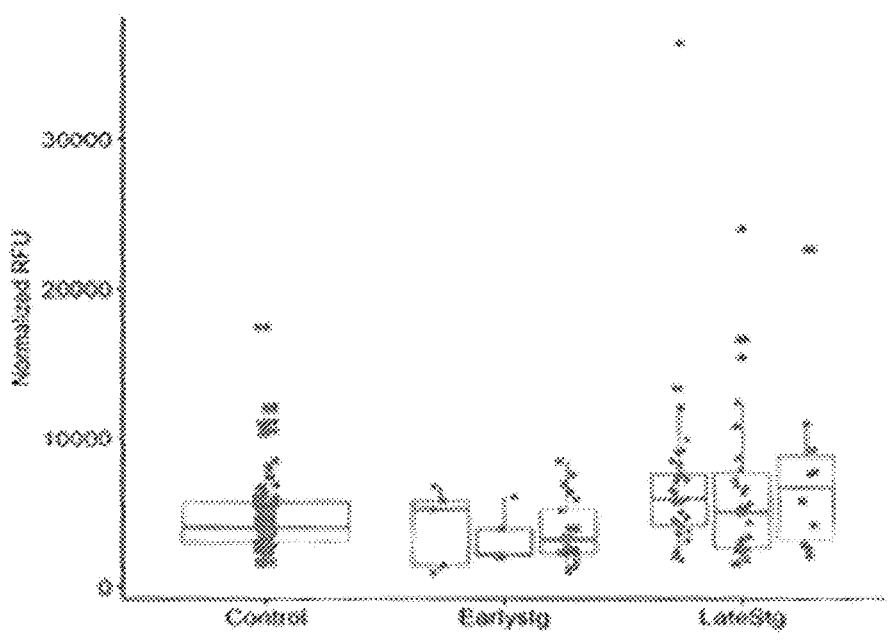
Figure 5:
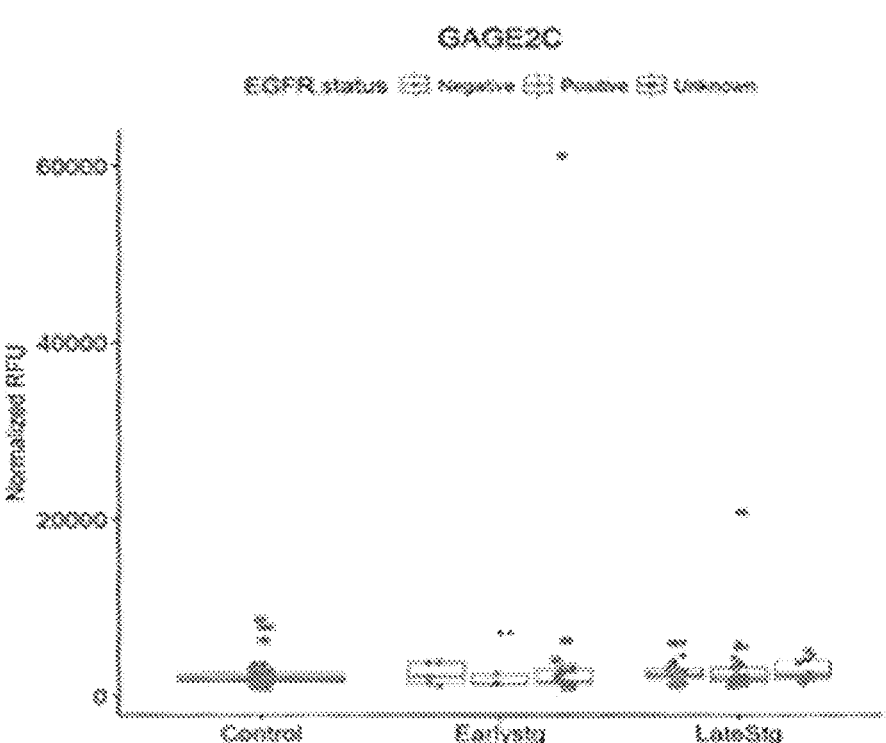

FIG. 5 shows a comparison of the core autoantibody biomarker panel (autoantibodies against antigens XAGE1D, LRRFIP2 and GAGE2C) levels with respect to EGFR status in patients. The data was generated from comparing normalised RFU values of the three ewe set of biomarkers (identified based on variable ranking using random forest) across healthy controls (Control), Early stage lung cancer patients (Earlystg) and Late stage lung cancer patients (Latestg). Patient cohorts were sub-divided based on EGFR mutation status i.e. Positive (patients with EGFR mutation), negative (patients without EGFR mutation), unknown (patients with unknown EGFR mutation status). An overall elevation of the antigen-specific autoantibody levels was observed in late stage NSCLC compared to early stage NSCLC and control.

Figure 6:
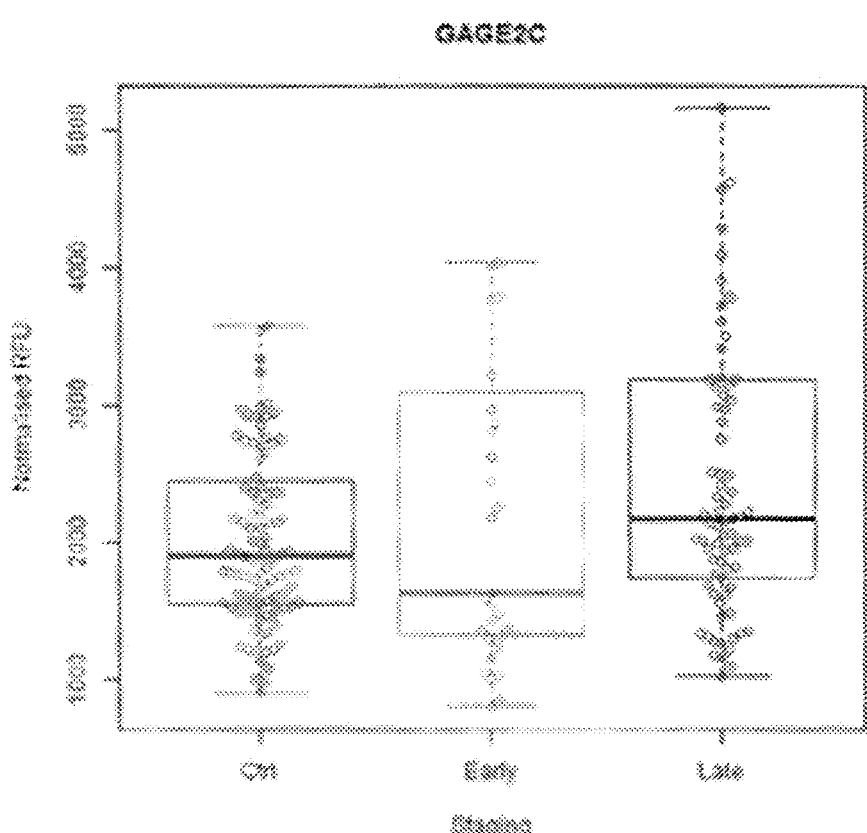
FIG. 6 illustrates the overall autoantibody profiles of the core set of biomarkers in three different stages of NSCLC.

A similar observation is seen in FIG. 6, wherein the data was generated from comparing normalised RFU values of the three core set of biomarkers (identified based on variable ranking using random forest) against healthy controls (Ctrl), Early stage lung cancer patients (Early) and Late stage lung cancer patients (Late).

Figure 7:
FIG. 7 illustrates the distinct molecular signatures for the 19 shortlisted biomarkers for NSCLC patients.

Furthermore, the elevation of antigen-specific autoantibody levels in late stage NSCLC is independent of EGFR status of patients. In addition, with further reference to FIG. 7, distinct differences in autoantibodies against XAGE1D, CTAG1A, CTAG2, GAGE1 and GAGE2C were observed in Late and Early stage NSCLC compared to the control Unsupervised clustering of individual fold changes across all healthy controls (Control), Early stage lung cancer patients (EarlyStg) and Late stage lung cancer patients (LateStg) for 19 biomarkers identified by pFC method. Clustering was performed for biomarkers based on Ward's method and distance calculated based on Euclidean distance. The shaded bar on the top of the heatmap represents patient cohorts i.e. Control, Early stage and Late Stage samples.

Validation Study Using a Custom Array Containing 19 Antigens Identified from the Phase 1 Study

Protein Expression

Nineteen BCCP-tagged antigens (XAGE1D; CTAG2; CTAG1A; STAT1; DDX53; MAGEA4; IGF2BP3; MAGEA10; LRRFIP2; ZNRD1; PTPN20A; RAD23B; CT47A1; MAP2K5; FADD, GAGE1; DDX43; GAGE2C; & TPM1) identified from the Phase 1 discovery study (see above) were expressed in insect cell cultures as previously described (see above). Cells were harvested and lysed as described above.

Custom Array Fabrication

Crude insect cell lysates for each of the 19 BCCP-tagged antigens were aliquoted into separate wells of a source plate and robotically printed on to streptavidin-coated hydrogel slides (Schott HS slides) to torn) a protein microarray. Each of the 19 antigens were printed in triplicate on one array. Sixteen replica arrays were printed in discrete areas of a 7.5×2.5 cm HS slide. Following printing, arrays were wash as stored as described above.

Study Cohort

Plasma samples from an independent cohort of 126 late stage NSCLC patients, 30 early stage NSCLC patients and 83 age-matched healthy controls were used to validate the 19 shortlisted antigens from the Phase 1 study, using the custom array fabricated as described above.

Sample Preparation, Data Handling and QC

For each plasma sample, 22.5 $\mu$L of the sample was pipetted into 4.5 mL of Serum Assay Buffer (SAB) containing 0.1% v/v Triton X-100, 0.1% w/v BSA in PBS (20° C.) and vortexed to mix three times. Diluted plasma were then assayed on custom protein microarrays, essentially as described above. Briefly, each custom protein microarray was removed from storage buffer using forceps, placed in a slide box containing 200 mL cold SAB and shaken on an orbital shaker at 50 rpm, for 5 minutes. The slides were then placed, array side up, in a slide hybridization chamber with individual plasma which had been diluted as above. All slides were scanned using a barcode scanner and incubated on a horizontal shaker at 50 rpm for 2 hours at 20° C. Each protein microarray slide was then rinsed twice with 30 mL SAB, followed by 200 mL of SAB buffer for 20 minutes on the shaker at 50 rpm at room temperature. All slides were transferred sequentially and in the same orientation. Arrays were then immersed in hybridization solution containing Cy3-rabbit anti-human IgG (diluted 1:1000 in SAB buffer) for 2 hours, with shaking at 50 rpm at 20° C.

After incubation, the slide was washed in 200 mL of SAB buffer, 3 times for 5 minutes with shaking at 50 rpm at room temperature. Excess buffer was removed by immersing the slide in 200 mL of pure water for a few minutes. Slides were then dried for 2 min at 240 g at room temperature and stored at room temperature until scanning Hybridization signals were measured with a microarray laser scanner (Agilent Scanner) at 10 $\mu$m resolution. Fluorescence intensities were detected according to the manufacturer's instructions, whereby each spot is plotted using Agilent Feature Extraction software.

Slide scanning, raw data handling and QC were carried out as described above for the Phase 1 study.

Data Analysis

A Penetrance Fold Change analysis was performed for each of the 19 antigens, comparing NSCLC patients and healthy controls, using the method described for the Phase 1 study data analysis. This demonstrated that all 19 antigens had an individual penetrance frequency >10% and a penetrance fold change >2 fold.

The results are summarised below. Table 3 shows the penetrance fold change analysis results for Late Stage NSCLC versus Healthy controls across all 19 antigens from the validation study. Table 4 shows the penetrance fold change analysis results for Early Stage NSCLC versus Healthy controls across all 19 antigens front the validation study

TABLE 3

| Protein | Penetrance Frequency (Late Stage) | Penetrance Frequency % (Late Stage) | Mean Penetrance (Late Stage) | Penetrance Fold Change (Late Stage) | Mean (Healthy Control) |
|---|---|---|---|---|---|
| XAGE1D | 33 | 26.19 | 2103.27 | 4.32 | 486.84 |
| CTAG2 | 26 | 20.63 | 1896.52 | 3.93 | 482.11 |
| CTAG1A | 25 | 19.84 | 3649.61 | 8.28 | 440.94 |
| STAT1 | 21 | 16.67 | 1219.31 | 2.70 | 451.38 |
| DDX53 | 20 | 15.87 | 7340.65 | 13.67 | 536.89 |
| MAGEA4 | 20 | 15.87 | 2722.11 | 6.17 | 440.83 |
| IGF2BP3 | 20 | 15.87 | 1428.20 | 3.13 | 455.58 |
| MAGEA10 | 20 | 15.87 | 1274.75 | 2.72 | 468.93 |
| LRRFIP2 | 20 | 15.87 | 1366.38 | 2.65 | 516.39 |
| ZNRD1 | 19 | 15.08 | 1440.51 | 2.96 | 486.98 |
| PTPN20A | 19 | 15.08 | 1244.62 | 2.67 | 466.38 |
| RAD23B | 18 | 14.29 | 1211.94 | 2.88 | 421.08 |
| CT47A1 | 18 | 14.29 | 1330.74 | 2.74 | 486.50 |
| MAP2K5 | 17 | 13.49 | 1227.44 | 2.86 | 429.29 |
| FADD | 16 | 12.70 | 1362.23 | 2.79 | 487.64 |
| GAGE1 | 16 | 12.70 | 1741.70 | 2.75 | 633.18 |
| DDX43 | 16 | 12.70 | 1274.21 | 2.70 | 471.32 |
| GAGE2C | 14 | 11.11 | 1441.22 | 2.93 | 491.95 |
| TPM1 | 13 | 10.32 | 3066.49 | 2.81 | 1090.13 |

TABLE 4

| Protein | Penetrance Frequency (EarlyStage) | Penetrance Frequency % (EarlyStage) | Mean Penetrance (EarlyStage) | Penetrance Fold Change (EarlyStage) | Mean (Control) |
|---|---|---|---|---|---|
| RAD23B | 8 | 26.67 | 992.75 | 2.36 | 421.08 |
| GAGE1 | 5 | 16.67 | 1498.35 | 2.37 | 633.18 |
| DDX43 | 5 | 16.67 | 1095.95 | 2.33 | 471.32 |
| XAGE1D | 4 | 13.33 | 3219.83 | 6.61 | 486.84 |
| LRRFIP2 | 4 | 13.33 | 1343.66 | 2.60 | 516.39 |
| MAGEA4 | 4 | 13.33 | 1141.63 | 2.59 | 440.83 |
| MAGEA10 | 4 | 13.33 | 1121.54 | 2.39 | 468.93 |
| GAGE2C | 4 | 13.33 | 1160.49 | 2.36 | 491.95 |
| CT47A1 | 4 | 13.33 | 1129.55 | 2.32 | 486.50 |
| PTPN20A | 4 | 13.33 | 1075.17 | 2.31 | 466.38 |
| MAP2K5 | 4 | 13.33 | 984.14 | 2.29 | 429.29 |
| STAT1 | 4 | 13.33 | 1033.02 | 2.29 | 451.38 |
| ZNRD1 | 4 | 13.33 | 1109.92 | 2.28 | 486.98 |
| TPM1 | 3 | 10.00 | 3102.74 | 2.85 | 1090.13 |
| CTAG1A | 3 | 10.00 | 1088.11 | 2.47 | 440.94 |
| IGF2BP3 | 3 | 10.00 | 1123.99 | 2.47 | 455.58 |
| CTAG2 | 3 | 10.00 | 1145.82 | 2.38 | 482.11 |
| DDX53 | 2 | 6.67 | 1260.99 | 2.35 | 536.89 |
| FADD | 2 | 6.67 | 1095.78 | 2.25 | 487.64 |

The performances of biomarker panels were validated by a Random Forest—Recursive feature elimination (RF-RFE) algorithm which is a backwards selection, iterative process used to select the best subset of biomarkers for the classification of NSCLC. Validation of the selected biomarkers involves using a training and testing set for model generation and performance evaluation before using an independent validation set to validate the final performance of the models.

During model generation, all possible combinations of 19 biomarkers were generated and the individual fold change values based on the biomarker combinations were used as inputs for model generation. Data front the phase I (209 samples) were separated into training (⅔rds) and test (⅓rd) datasets. Training using the RF-RFE was done using default parameters with 5-fold cross validation and panel size being fixed to the number of biomarkers in each model. The generated models were used to predict both the testing and validation sets to evaluate the performance of the panels in the stratification of NSCLC. All recursive feature elimination and Random Forest analyses were performed using the caret (Kuhn. 2008 (https://www.jstatsoft.org/article/view/v028i05)) package in R.

The performance of the RF-RFE models on the training dataset are summarized in Table 7 which includes results for the performance of the core biomarkers, 19 biomarkers and the top 20 panels based on descending AUC values.

Figure 10:
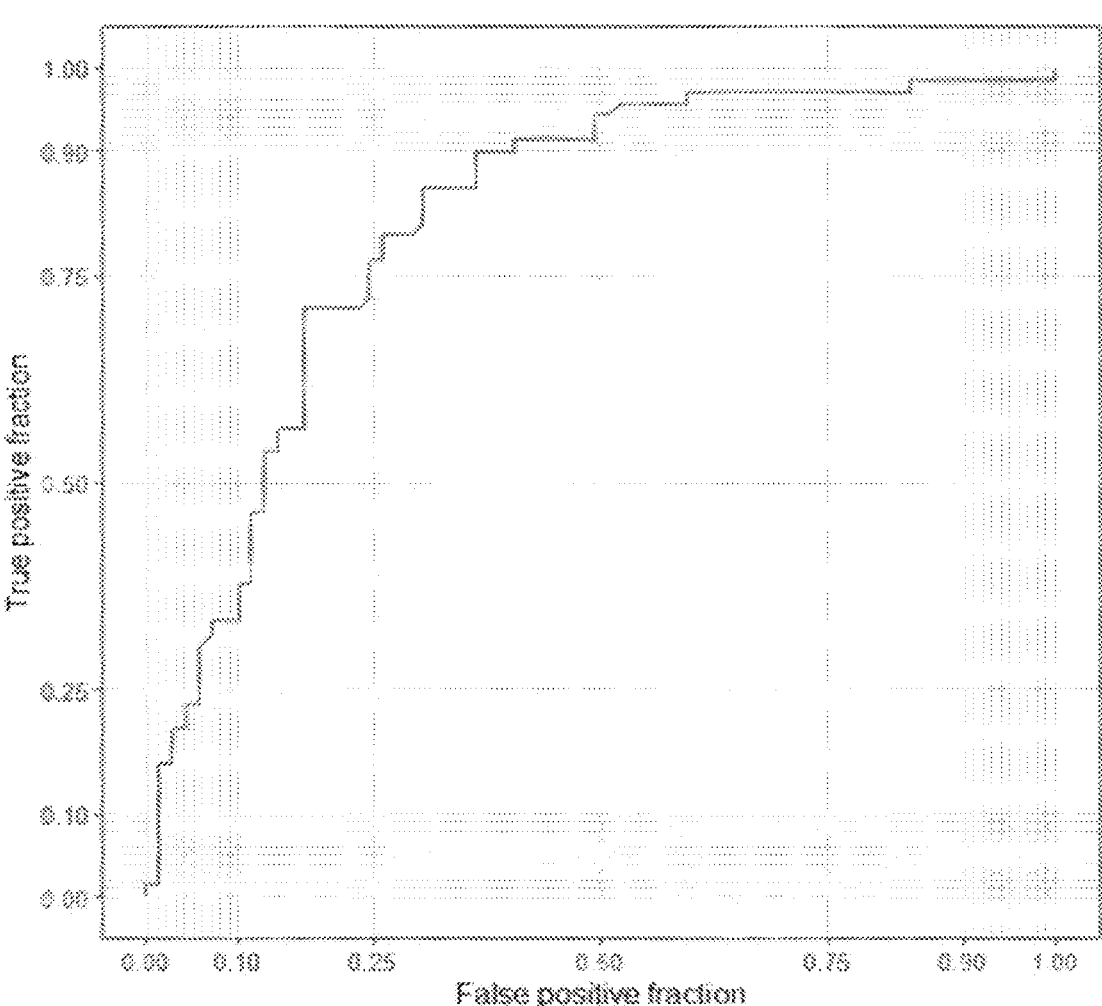
FIG. 10 illustrates the ROC curves for the best panel of 7 biomarkers in the validation study.
Figure 11:
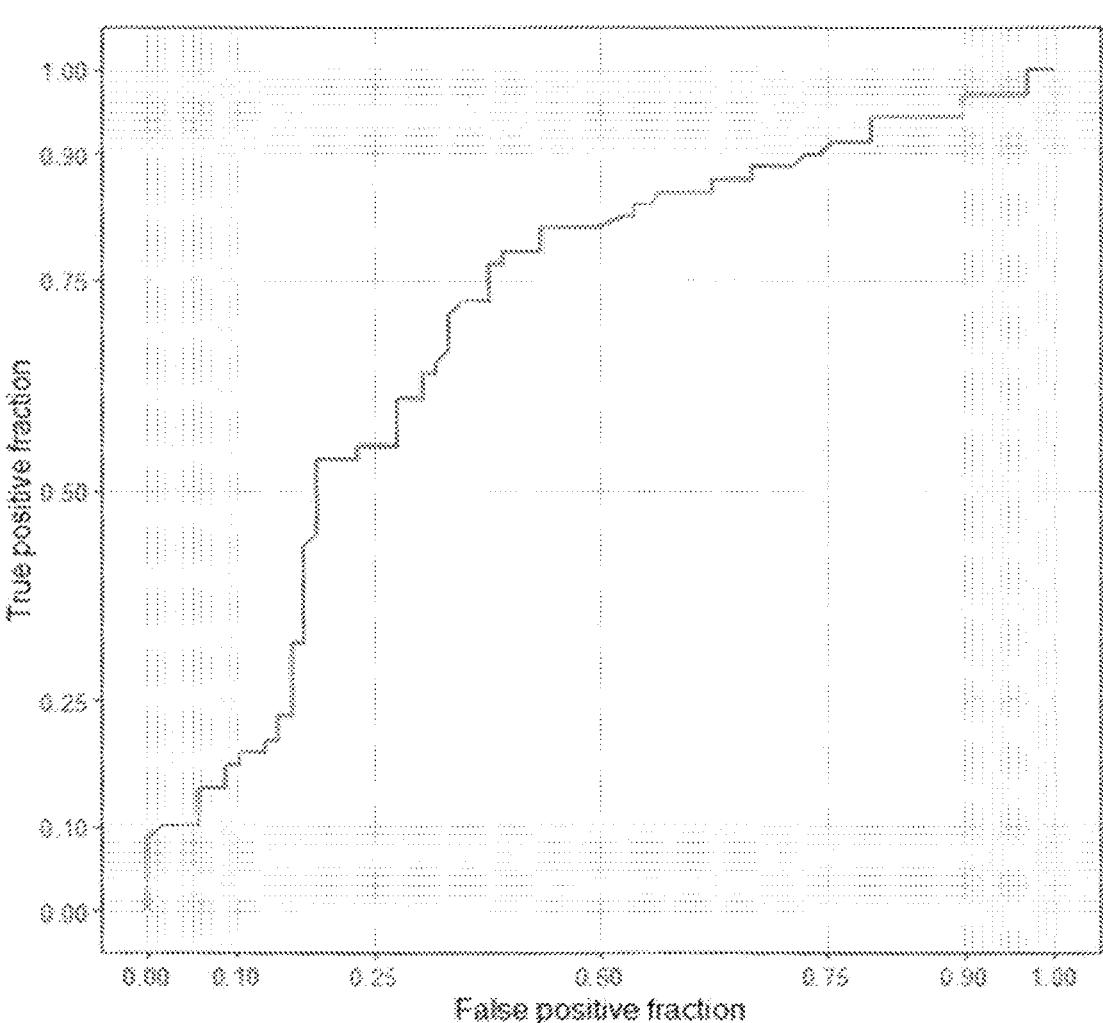
FIG. 11 illustrates the ROC curves for the 19 biomarkers in the validation study.

Results have demonstrated that the panel of 7 biomarkers which includes the core biomarkers (XAGE1D, LRRFIP2, GAGE2C) outperform a panel of 19 biomarkers with Sensitivity and Specificity of 0.753 and 0.721 compared to 0.680 and 0.652 respectively. FIGS. 10 and 11 show the ROC curves for the best panel of 7 biomarkers (XAGE1D, LRRFIP2, MAGEA10, GAGE2C, STAT1, ZNRD1, RAD23B; with an AUC of 0.818), and the 19 biomarkers (with an AUC of 0.702) respectively.

Extracellular vesicles can be divided into three main categories, namely apoptotic bodies, microvesicles, and exosomes. Exosomes are the smallest extracellular vesicles which are naturally secreted by almost every cell type and can be found in almost all biological fluids including blood, serum, plasma, urine, saliva, amniotic fluid, cerebrospinal fluid, breast milk, semen and bile. In general, cells release exosomes via two mechanisms. The classic pathway involves the formation of intraluminal vesicles within multi vesicular endosomes. In turn, the membrane of multivesicular endosomes fuses with the plasma membrane, resulting in the release of intraluminal vesicles. When secreted, intraluminal vesicles are called exosomes. Alternatively, the direct pathway involves the release of vesicles, indistinguishable from exosomes, directly from the plasma membrane (van der Pol et al. 2012) interestingly, exosomes from cancer cells have been shown to promote angiogenesis, modulate the immune system and remodel the surrounding parenchymal tissue, all factors supporting tumor progression (Hessvik and Llorente, 2018).

Exosome samples from patients with NSCLC and healthy controls were collected and isolated using Invitrogen Total Exosome Isolation (from plasma) kit (Thermo Fisher Scientific.) based on the established protocol from the manufacturer.

The discovery of these autoantibody biomarkers using exosome samples can be more disease-specific and meaningful as they contain membrane-bound proteins that reflect their originating cell. In cancer, exosomes have been shown to be implicated in the crosstalk between tumour cells and normal cells thereby facilitating the malignant process. Several studies have found exosomes to be promising as diagnostic and prognostic markers (Sanfeld-Paulsen et al., 2016).

It will be appreciated by persons skilled in the art that the present invention may also include further additional modifications made to the system which does not affect the overall functioning of the system.

REFERENCES

Bolstad, B. M. et al (2013) A comparison of normalization methods for high density oligonucleotide array data based on variance and bias. Bioinformatics 19(2), 185-93.

Cimino, Y. et al. (2012). FADD protein release mirrors the development and aggressiveness of human non-small cell lung cancer. British Journal of Cancer, 106, 1989-1996.

Hessvik N P and Llorente A (2018) Current knowledge on exosome biogenesis and release. Cell Mol Life Sci., 75(2): 193-208.

Lopez-Ratón, M., Rodriguez-Álvarez, M. X., Cadarso-Suárez, C., & Gude-Sampedro, F. (2014). OptimalCutpoints: an R package for selecting optimal cutpoints in diagnostic tests Journal of Statistical Software, 61(8), 1-36

Maniatis T. et al (1989) Molecular Cloning: A Laboratory Manual Cold Spring Harbor Press Meissl et al. (2017). The good and the bad faces of STAT1 in solid tumours. Cytokine, vol 89, pages 12-20.

Sanfeld-Paulsen, B et al. (2016). Exosomal proteins as prognostic biomarkers in non-small cell lung cancer. Molecular Oncology, Vol 10, issue 10, pages 1595-1602.

Silva et al. (2017). Genome-wide identification of cancer/testis genes and their association with prognosis in a pan-cancer analysis Oncotarget 8.92966.

van der Pol, Edwin et al. (2012). Pharmacological reviews Classification, Functions, and Clinical Relevance of Extracellular Vesicles.

Rao, T P & Kuhl, M. (2010) An updated overview on Wnt signalling pathways: a prelude for more Circ Res 25; 106(12): 1798-806.

Wang et al. (2016) Systematic identification of genes with a cancer-testis expression pattern in 19 cancer types. Nature Communications 7, 10499.

www.genecards.org

TABLE 5

| Protein Name | UniprotID | Description |
|---|---|---|
| XAGE1D | Q9HD64 | >P003055_Q211_Q211_tube_XAGE1_9503_0_NM_020411.2_0_Q9HD64_0_Insert sequence is gene optimized by GeneArt_0_0_0 |

Nucleotide Sequence (Seq ID No. 1):
ATGGAATCCCCCAAGAAGAAGAACCAGCAGCTGAAGGTCGGAATCCTGCACCTGGGTTCCCGTCAGAAGAAGA
TCCGTATCCAGCTGCGTTCCCAGTGCGCTACCTGGAAGGTCATCTGCAAGTCCTGCATCTCCCAGACCCCCGG
TATCAACCTGGACCTGGGCTCCGGTGTCAAGGTCAAGATCATCCCCAAGGAAGAACACTGGAAGATGCCCGAG
GCTGGCGAGGAACAGCCCCAGGTG Protein Sequence (Seq ID No. 20):
MESPKKKNQQLKVGILHLGSRQKKIRIQLRSQCATWKVICKSCISQTPGINLDLGSGVKVKIIPKEEHCKMPEAGEEQPQV

| LRRFIP2 | Q9Y608 | >P001894_Q305_Q305p2_LRRFIP2_9209_Homo sapiens leucine rich repeat (in FLII) interacting protein 2_BC053668.1_AAH53668.1_Q9Y608_0_0_1203_0_1200 |

Nucleotide Sequence (Seq ID No. 2):
ATGGGGACTCCTGCTTCTGGAAGGAAAAGAACACCTGTGAAAGACCGATTTTCTGCAGAAGATGAAGCTTTGAG
TAACATTGCCAGAGAGGCAGAGGCAAGGCTGGCAGCAAAACGGGCTGCCCGGGCAGAAGCAAGAGATATACG
CATGAGAGAACTGGAACGACAACAAAAAGAGTTGGATGAAAAATCTGACAAACAGTATGCTGAAAATTATACAA
GACCTTCATCTCGAAATTCTGCCTCAGCAACAACCCCTCTAAGTGGAAACTCATCCAGACGAGGAAGTGGGGAC
ACCAGCAGCTTAATAGATCCAGACACTTCATTAAGTGAATTGCGGGAATCTTTGTCTGAAGTGGAAGAAAAATAC
AAGAAAGCCATGGTTTCCAATGCACAGTTAGACAATGAGAAGAACAATTTGATCTACCAAGTAGACACACTCAAG
GATGTTATTGAAGAGCAGGAGGAACAGATGGCAGAATTTTATAGAGAAAATGAAGAAAAATCAAAGGAGTTAGA
AAGGCAGAAACATATGTGTAGTGTGCTGGAGCATAAGATGGAAGAACTTAAAGAAGGCCTGCGGCAAAGAGAT
GAGCTTATTGAGAAACATGGCTTAGTTATAATCCCCGATGGCACTCCCAATGGTGATGTCAGTCATGAACCAGT
GGCTGGAGCCATCACTGTTGTGTCTCAGGAAGCTGCTCAGGTCTTGGAGTCAGCAGGAGAAGGGCCATTAGAT
GTAAGGCTACGAAAACTTGCTGGAGAGAAGGAAGAACTACTGTCACAGATTAGAAAACTGAAGCTTCAGTTAGA
GGAGGAACGACAGAAATGCTCCAGGAATGATGGCACAGTGGGTGACCTGGCAGGACTGCAGAATGGCTCAGA
CTTGCAGTTCATCGAAATGCAGAGAGATGCCAATAGACAAATTAGCGAATACAAATTTAAGCTTTCAAAAGCAGA
ACAGGATATAACTACCTTGGAGCAAAGTATTAGGCGGCTTGAGGGACAGGTTCTGAGATATAAAACTGCTGCTG
AGAATGCTGAGAAAGTTGAAGATGAATTGAAAGCAGAAAAACGGAAGCTACAACGAGAGTTACGAACAGCACTG
GACAAGATTGAGGAGATGGAGATGACCAACAGCCACCTGGCCAAGCGGCTGGAGAAGATGAAGGCCAATAGG
ACAGCACTTCTGGCCGAGCAG TABLE 5-continued

| Protein Name | UniprotID | Description |
| --- | --- | --- |

Protein Sequence (Seq ID No.21)
MGTPASGRKRTPVKDRFSAEDEALSNIAREAEARLAAKRAARAEARDIRMRELERQQKELDEKSDKQYAENYTAPS
SRNSASATTPLSGNSSRRGSGDTSSLIDPDTSLSELRESLSEVEEKYKKAMVSNAQLDNEKNNLIYQVDTLKDVIEEQ
EEQMAEFYRENEEKSKELERQKHMCSVLQHKMEELKEGLRQRDELIEKHGLVIIPDGTPNGDVSHEPVAGAITVVSQ
EAAQVLESAGEGPLDVRLRKLAGEKEELLSQIRKLKLQLEEERQKCSRNDGTVGDLAGLQNGSDLQFIEMQRDANR
QISEYKFKLSKAEQDITTLEQSISRLEGQVLRYKTAAENAEKVEDELKAEKRKLQRELRTALDKIEEMEMTNSHLAKRL
EKMKANPTALLAQQ

| GAGE2C | Q13066 | >P003037_Q211_Q211_tube_GAGE2C_2574_0_NM_001472.2_0_Q13066_0_Insert sequence is gene optimized by GeneArt_0_0_0 |

Nucleotide Sequence (Seq ID No. 3):
ATGTCCTGGCGTGGTCGTTCCACCTACCGTCCCCGTCCTCGTCGTTACGTCGAGCCCCCCGAGATGATCGGTC
CCATGCGTCCCGAGCAGTTCTCCGACGAGGTCGAGCCCGCTACCCCCGAGGAAGGCGAGCCTGCTACTCAGC
GTCAGGACCCCGCTGCTGCTCAAGAGGGCGAGGACGAGGGCGCTTCCGCTGGCCAGGGTCCTAAGCCCGAG
GCTCACTCCCAAGAGCAGGGTCACCCCCAGACCGGTTGCGAGTGCGAGGACGGTCCCGACGGTCAAGAGATG
GACCCCCCCAACCCTGAGGAAGTCAAGACCCCCGAAGAGGGCGAAAAGCAGTCCCAGTGC Protein Sequence (Seq ID No. 22):
MSWRGRSTYRPRPRRYVEPPEMIGPMRPEQFSDEVEPATPEEGEPATQRQDPAAAQEGEDEGASAGQGPKPEAH
SQEQGHPQTGCECEDGPDGQEMDPPNPEEVKTPEEGEKQSQC

| DDX53 | Q86TM3 | >P003022_Q211_Q211_tube_DDX53_168400_0_NM_182699.2_0_Q86TM3_0_Insert sequence is gene optimized by GeneArt_0_0_0 |

Nucleotide Sequence(Seq ID No. 4):
ATGTCCCACTGGGCTCCCGAGTGGAAGCGTGCTGAGGCTAACCCCCGTGACCTGGGCGCTTCTTGGGACGTG
CGCGGTTCCCGTGGTAGCGGTTGGAGCGGTCCCTTCGGTCACCAAGGTCCCCGTGCTGCTGGTTCCCGCGAG
CCCCCCGTGCTTCAAGATCAAGAACAACATGGTCGGAGTGGTCATCGGTTACTCCGGTTCCAAGATCAAGG
ACCTGCAGCACTCCACCAACACCAAGATCCAGATCATCAACGGCGAGTCCGAGGGCTAAGGTCCGCATCTTCGG
CAACCGCGAGATGAAGGCTAAGGCCAAGGCTGCTATCGAGACTCTGATCCGCAAGCAAGAGTCCTACAACTCC
GAGTCCTCCGTGGCAACGCTGCTTCCCAGAGCCCCATCGGTCGTAACCTGGGTCGTAACGACATCGTGGGC
GAGGCTGAGCCCTGTCCAACTGGGACCGTATCCGCGCTGCTGTGGTCGAGTGCGAGAAGCGCAAGTGGGCT
GACCTGCCCCCCGTGAAGAAGAACTTCTACATCGAGTCCAAGGCTACCTCCTGCATGTCCGAGATGCAAGTGA
TCAACTGGCGCAAGGAAAACTTCAACATCACTTGCGACGACCTGAAGTCCGGCGAGAAGCGTCTGATCCCCAA
GCCTACCTGCCGTTTCAAGGACGCTTTCCAGCAGTACCCCGACCTGCTGAAGTCCATCATCCGTGTGGGTATC
GTGAAGCCCACCCCCATCCAGTCCCAGGCTTGGCCAATCATCCTGCAGGGTATCGACCTGATCGTGGTGGCTC
AGACCGGCACCGGCAAGACCCTGTCCTACCTGATGCCCGGTTTCATCCACCTGGACTCCCAGCCCATCTCCCG
CGAGCAGCGTAACGGTCCCGGCATGCTGGTGCTGACCCCCTACCCGTGAACTGGCTCTGCACGTCGAGGCTGA
GTGCTCCAAGTACTCCTACAAGGGCCTGAGTCTATCTGCATCTACGGTGGTCGTAACCGTAACGGCCAGATC
GAGGACATCTCCAAGGGTGTCGACATCATCATTGCTACCCCCGGTCGTCTGAACGACCTGCAGATGAACAACT
CCGTGAACCTGCGTTCCATCACCTACCTGGTCATCGACGAGGCTGACAAGATGCTGGACATGGAGTTCGAGCC
CCAGATCCGCAAGATCCTGCTGGACGTGCGTCCCGACCGTCAGACCGTGATGACCTCCGCTACCTGGCCCGA
CACCGTGCGTCAGCTGGCTCTGTCTTACCTGAAGGACCCCATGATCGTGTACGTGGGCAACCTGAACCTGGTG
GCTGTGAACACCGTGAAGCAGAACATCATCGTGACCACCGAGAAGGAAAAGAGGGCTCTGACCCAAGAGTTCG
TCGAGAACATGTCCCCCAACGACAAGGTCATCATGTTCGTGTCCCAGAAGCACATTGCTGACGACCTGTCCTCC
GATTTCAACATCCAAGGCATCTCCGCTGAGTCCCTGCACGGCAACTCCGAGCAGTCCGACCAAGAGCGTGCTG
TCGAGGACTTCAAGTCCGGCAACATCAAGATCCTCATCACCACCGACATCGTGTCCCGTGGCCTGGACCTGAA
CGACGTGACCCACGTGTACAACTACGACTTCCCCCGTAACATCGACGTGTACGTGCACCGTGTGGGTTACATC
GGTCGCACCGGAAAGACCGGAACCTCCGTGACCCTGATCACCCAGCGCGACTCCAAGATGGCTGGCGAGCTG
ATCAAGATCTTGGACCGTGCTAACCAGTCCGTGCCCGAGGACCTGGTGGTCATGGCTGAGCAGTACAAGCTGA
ACCAGCAGAAGCGTCACCGCGAGACTCGTTCCCGCAAGCCCGGACAGCGTCGCAAGGAGTTCTACTTCCTGTC
C Protein Sequence(Seq ID No. 23):
MSHWAPEWKRAEANPRDLGASWDVRGSRGSGWSGPFGHQGPRAAGSREPPLCFKIKNNMVGVVIGYSGSKIKDL
QHSTNTKIQIINGESEAKVRIFGNREMKAKAKAAIETLIRKQESYNSESSVDNAASQTPIGRNLGRNDIVGEAEPLSNW
DRIRAAVVECEKRKWADLPPVKKNFYIESKATSCMSEMQVINWRKENFNITCDDLKSGEKRLIPKPTCRFKDAFQQY
PDLLKSIIRVGIVKPTPIQSQAWPIILQGIDLIVVAQTGTGKTLSYLMPGFIHLDSQPISREQRNGPGMLVLTPTRELALH
VEAECSKYSYKGLKSICIYGGRNRNGQIEDISKGVDIIIATPGRLNDLQMNNSVNLRSITYLVIDEADKMLDMEFEPQIR
KILLDVRPDRQTVMTSATWPDTVRQLALSYLKDPMIVYVGNLNLVAVNTVKQNIIVTTEKEKRALTQEFVENMSPNDK
VIMFVSQKHIADDLSSDFNIQGISAESLHGNSEQSDQERAVEDFKSGNIKILITTDIVSRGLDLNDVTHVYNYDFPRNID
VYVHRVGYIGRTGKTGTSVTLITQRDSKMAGELIKILDRANQSVPEDLVVMAEQYKLNQQKRHRETRSRKPGQRRKE
FYFLS

| DDX43 | Q9NXZ2 | >P003043_Q211_Q211_tube_DDX43_55510_0_NM_018665.2_0_Q9NXZ2_0_Insert sequence is gene optimized by GeneArt_0_0_0 |

Nucleotide Sequence(Seq ID No. 5):
ATGTCCCACCACGTGGTGCTCCCAAGGCTTCCACCTGGGTGGTGGCTTCCCGTCGTTCCTCCAGCGTGTCCC
GTGCTCCCGAGCGTCGTCCCGCTGAGGAACTGAACCGTACCGGTCCCGAGGGCTACTCCGTGGGTCGTGGTG
GTCGTTGGCGTGGCACCTCTCGTCCCCCTGAGGCTGTGGCTGTGGTCACGAGGAACTGCCCCCTGTGCTTCG
CTCTGAAGTCCCACTTCGTGGGTGCTGTGATCGGTCGCGGTGGTTCCAAGATCAAGAACATCCAGTCCACCAC
CAACACCACCATCCAGATCATCAAGAGCAGCCCGAGTCCCTGGTCAAGATCTTCGGTTCCAAGGCTATGCAG
ACCAAGGCTAAGGCTGTGATCGACAACTTCGTGAAGAAGCTGGAAGAGAACTACAACTCCGAGTGCGGTATCG
ACACCGCTTTCCAGCCCTCCGTGGGCAAGGACGGTTCCACCGACAACAACGATGGTGGCTGGCGACCGTCCCC
TGATCGACTGGGACCAGATCCGTGAAGAGGGCCTGAAGTGGCAAAAGACCAAGTGGGCTGACCTGCCCCCCA
TCAAGAAGAACTTCTACAAGGAATCCACCGCTACCTCCGCTATGTCCAAGGTCGAGGCTGACTCCTGGCGCAA
GGAAAACTTCAACATCACCTGGGACGACCTGAAGGACGGCGAGAAGCGTCCCATCCCCAACCCTACCTGCACC
TTCGACGACGCTTTCCAGTGCTACCCCGAAGTGATGGAAAACATCAAGAAGGCTGGTTTCCAGAAGCCCACCC
CCATCCAGTCCCAGGCTTGGCCCCATCGTGCTGCAGGGTATCGACCTGATCGGTGTCGCTCAGACCGGCACCG TABLE 5-continued

| Protein Name | UniprotID | Description |
| --- | --- | --- |

GCAAGACCCTGTGCTACCTGATGCCCGGTTTCATCCACCTGGTGCTGCAGCCCTCCCTGAAGGGGCAGCGTAA
CCGTCCCGGCATGCTGGTGCTGACCCCTACCCGCGAACTGGCTCTGCAGGTCGAGGGCGAGTGCTGCAAGTA
CTCCTACAAGGGCCTGCGTTCCGTGTGCGTGTACGGTGGTGGCAACCGTGACGAGCAGATCGAGGAACTCAA
GAAGGGTGTCGACATCATCATCGCTACCCCCGGTCGTCTGAACGACCTGCAGATGTCCAACTTCGTCAACCTG
AAGAACATCACCTACCTGGTCCTGGACGAGGCTGACAAGATGCTGGACATGGGTTTCGAGCCCCAGATCATGA
AGATCCTGCTGGACGTGCGTCCCGACCGTCAGACCGTGATGACCTCCGCTACCTGGCCCCACTCCGTGCACC
GTCTGGCTGAGTCCTACCTGAAGGAACCCATGATCGTGTACGTGGGCACCCTGGACCTGGTGGCTGTGTCCTC
CGTGAAGCAGAACATCATCGTGACCACCGAGGAAGAGAAGTGGTCCCACATGCAGACTTTCTTGCAGTCCATG
TCCTCTACCGACAAGGTCATCGTGTTCGTGTCCCGCAAGGCTGTCGCTGACCACCTGTCCTCCGACCTGATCC
TGGGCAACATCTCCGTCGAGTCCCTGCACGGCGACCGCGAGCAGCGTGACCGCGAGAAGGCTCTCGAGAACT
TCAAGACCGGCAAGGTCCGCATCCTGATCGCTACCGACCTGGCTTCCCGCGGACTGGACGTGCACGACGTGA
CCCACGTGTACAACTTCGACTTCCCCCGTAACATCGAGGAATACGTGCAGCGTATCGGTCGTACCGGTCGTGC
TGGTCGCACCGGTGTCTCCATCACCACCCTGACCCGTAACGACTGGCGTGTGGCTTCCGAGCTGATCAACATC
CTCGAGCGTGCTAACCAGTCCATCCCCGAGGAACTGGTGTCTATGGCTGAGCGTTTCAAGGCTCACCAGCAAA
AGCGCGAGATGGAACGCAAGATGGAACGTCCCCAGGGTCGTCCCAAGAAGTTCCAC

Protein Sequence(Seq ID No. 24):
MSHHGGAPKASTWVVASRRSSTVSRAPERRPAEELNRTGPEGYSVGRGGRWRGTSRPPEAVAAGHEELPLCFAL
KSHFVGAVIGRGGSKIKNIQSTTNTTQIIQEQPESLVKIFGSKAMQTKAKAVIDNFVKKLEENYNSECGIDTAFQPSVG
KDGSTDNNVVAGDRPLIDWDQIREEGLKWQKTKWADLPPIKKNFYKESTATSAMSKVEADSWRKENFNITWDDLKD
GEKRPIPNPTCTFDDAFQCYPEVMENIKKAGFQKPTPIQSQAWPIVLQGIDLIGVAQTGTGKTLCYLMPGFIHLVLQPS
LKGQRNRPGMLVLTPTRELALGVEGECCKYSYKGLRSVCVYGGGNRDEQIEELKKGVDIIIATPGRLNDLQMSNFVN
LKNITYLVLDEADKMLDMGFEPQIMKILLDVRPDRQTVMTSATWPHSVHRLAQSYLKEPMIVYVGTLDLVAVSSVKQN
IIVTTEEEKWSHMQTFLGSMSSTDKVIVFVSRKAVADHLSSDLILGNISVESLHGDREQRDREKALENFKTGKVRILIAT
DLASRGLDVHDVTHVYNFDFPRNIEEYVHRIGRTGRAGRTGVSITTLTRNDWRVASELINILERANQSIPEELVSMAE
RFKAHQQKREMERKMERPQGRPKKFH GAG1          Q13065      >P003036_Q211_Q211_tube_GAG1_2543_0_NM_001040663.2_0_Q13068_0_Insert
                          sequence is gene optimized by GeneArt_0_0_0
Nucleotide Sequence(Seq ID No. 6):
ATGTCCTGGCGTGGTCGTTCCACCTACTACTGGCCCCCGTCCCCGTCGTTACGTGCAGCCCGCCGAGATGATCG
GTCCCATGCGTCCCGAGCAGTTCTCCGACGAGGTCGAGCCCGCTACCCCCGAGGAAGGCGAGCCTGCTACTC
AGCGTCAGGACCCCGCTGCTGCTCAAGAGGGCGAGGACGAGGGCGCTTCCGCTGGCCAGGGTCCTAAGCCC
GAGGCTGACTCCCAAGAGCAGGGTCACCCCCAGACCGGTTGCGAGTGCGAGGACGGTCCCGACGGTCAAGA
GATGGACCCCCCCAACCCTGAGGAAGTCAAGACCCCCGAAGAGGGCGAAGGCCAGTCCCAGTGC Protein Sequence(Seq ID No. 25):
MSWRGRSTYYWPRPRRYVQPPEMIGPMRPEQFSDEVEPATPEEGEPATQRQDPAAAQEGEDEGASAGQGPKPE
ADSQEQGHPQTGCECEDGPDGQEMDPPNPEEVKTPEEEMRSHYVAQTGILWLLMNNCFLNLSPRKP MAGEA10       P43363      >P003053_Q211_Q211_tube_MAGEA10_4109_0_NM_001011543.1_0_P43363_0_Insert
                          sequence is gene optimized by GeneArt_0_0_0
Nucleotide Sequence(Seq ID No. 7):
ATGCCCCGTGCTCCCAAGCGTCAGCGTTGCATGCCCGAAGAGGACCTGCAGTCCCAGTCCGAGACTCAGGGC
CTCGAGGGTGCTCAGGCTCCCCTGGCTGTGGAAGAGGACGCTTCCAGCTCTACCTCTACCTCCTGCAGCTTCC
CCAGCAGCTTCCCATCCTCCAGCTCCTCTAGCTCCTCCTCCTGCTACCCCCTGATCCCCTCCACCCCCGAGGA
AGTGTCCGCTGACGACGAGACTCCCAACCCCCCCCAGTCCGCTCAGATCGCTTGCTCCTCCCCCTCCGTGGTG
GCTTCCCTGCCTCTGGACCAGTCCGACGAGGGTTCCAGCTCCCAGAAGGAAGAGTCCCCCAGCACCCTGCAG
GTCCTGCCCGACTCCGAGTCCCTGCCCCGTTCCGAGATCGACGAGAAGGTTACAGACCTGGTGCAGTTCCTGC
TGTTCAAGTACCAGATGAAGGAACCCATCACCAAGGCTGAGATCCTCGAGTCCGTGATCAAGAACTACGAGGA
CCACTTCCCCCTGCTGTTCTCCGAGGCTTCCGAGTGCATGCTGCTGGTGTTCGGTATCGACGTGAAGGAAGTG
GACCCTACCGGTCACTCCTTCGTGCTGGTCACCTCCCTGGGCCTGACCTACGACGGCATGCTGTCCGACGTGC
AGTCCATGCCCAAGACCGGTATCCTGATCCTCATCCTGTCCATCATCTTCATCGAGGGCTACTGCACTCCTGAG
GAAGTGATCTGGGAGGCTCTGAACATGATGGGCCTGTACGACGGAATGGAACACCTGATCTACGGCGAGCCC
CGCAAGCTGCTGACCCAGGACTGGGTGCAAGAGAACTACCTCGAGTACCGTCAGGTGCCCGGTTCCGACCCC
GCTCGTTACGAGTTCCTGTGGGGTCCCCGTGCTCACGCTGAGATCCGCAAGATGTCCCTGCTGAAGTTCCTGG
CTAAGGTCAACGGCTCCGACCCCCGTTCCTTCCCACTGTGGTACGAGGAAGCTCTGAAGGACGAGGAAGAGA
GGGCTCAGGACCGTATCGCTACCACCGACGACACCACCGCTATGGCTTCCGCTTCCTCTAGCGCTACCGGTTC
CTTCAGCTACCCCGAG Protein Sequence(Seq ID No. 26):
MPRAPKRQPCMPEEQLQSQSETQGLEGAQAPLAVEEDASSSTSTSSSFPSSFPSSSSSSSSSCYPLIPSTPEEVSA
DDETPNPPQSAQIACSSPSVVASLPLDQSDEGSSSQKEESPSTLQVLPDSESLPRSEIDEKVTDLVGFLLFKYQMKE
PITKAEILESVIRNYEDHFPLLFSEASECMLLVFGIDVKEVDPTGHSFVLVTSLGLTYDGMLSDVQSMPKTGILILILSIVF
IEGYCTPEEVIWEALNMMGLYDGMEHLIYGEPRKLLTQDWVQENYLEYRQVPGSDPARYEFLWGPRAHAEIRKMSL
LKFLAKVNGSDPRSFPLWYEEALKDEEERAQDRIATTDDTTAMASASSSATGSFSYPE ZNRD1         Q9P1U0      >P000875_TRN_TRNp2_ZNRD1_30834_Homo sapiens zinc ribbon domain
                          containg 1 transcript variant
                          b_BC010898.1_AAH10898.1_Q9P1U0_0_0_381_0_378
Nucleotide Sequence(Seq ID No. 8):
ATGTCTGTCATGGACCTCGCCAATACTTGCTCCAGCTTTCAGTCGGACCTGGATTTCTGTTCAGATTGCGGCTC
GGTCCTGCCTCTGCCCGGGGCTCAGGATACGGTCACCTGTATTCGCTGTGGCTTCAACATCAACGTTCGGGAC
TTTGAGGGGAAGGTTGTGAAGACTTCGGTTGTGTTCCACCAACTGGGGACAGCCATGCCTATGTCGGTGGAGG
AAGGGCCTGAGTGCCAGGGACCTGTGGTTGACAGGCGCTGCCCTCGATGTGGTCATGAAGGAATGGCATACC
ACACCAGACAGATGCGTTCAGCCGATGAAGGGCAAACTGTCTTCTACACCTGTACCAACTGCAAGTTCCAGGA
GAAGGAAGACTCT TABLE 5-continued

| Protein Name | UniprotID | Description |
| --- | --- | --- |

Protein Sequence(Seq ID No. 27):
MSVMDLANTCSSFQSDLDFCSDCGSVLPLPGAQDTVTCIRCGFNINVRDFEGKVVKTSVVFHQLGTAMPMSVEEGP
ECQGPVVDRRCPRCGHEGMAYHTRQMRSADEGQTVFYTCTNCKFQEKEDS MAP2K5　　　　　Q1363　　　　>P000081_KIN96_KIN_MAP2K5_5607_*Homo sapiens* mitogen-activated
　　　　　　　　　　　　　　　　protein kinase kinase 5, transcript variant
　　　　　　　　　　　　　　　　A_BC008838.2_AAH08838.1_Q13163_4111679_0_1347_0_1344
Nucleotide Sequence(Seq ID No. 9):
ATGCTGTGGCTAGCCCTTGGCCCCTTTCCTGCCATGGAGAACCAGGTGCTGGTAATTCGCATCAAGATCCCAAA
TAGTGGCGCGGTGGACTGGACAGTGCACTCCGGGCCGCAGTTACTCTTCAGGGATGTGCTGGATGTGATAGG
CCAGGTTCTGCCTGAAGCAACAACTAGAGCATTTGAATATGAAGATGAAGATGGTGATCGAATTACAGTGAGAA
GTGATGAGGAAATGAAGGCAATGCTGTCATATTATTATTCCACAGTAATGGAACAGCAAGTAAATGGACAGTTAA
TAGAGCCTCTGCAGATATTTCAAGAGCCTGCAAGCCTCCTGGGGAACGGAACATACATGGCCTGAAGGTGAA
TACTCGGGCCGGACCCTCTCAACACAGCAGCCCAGCAGTCTCAGATTCACTTCCAAGCAATAGCTTAAAGAAGT
CTTCTGCTGAACTGAAAAAAAATACTAGCCAATGGCCAGATGAATGAACAAGACATACGATATCGGGACACTCTT
GGTCATGGCAACGGAGGCACAGTCTACAAAGCATATCATGTCCCGAGTGGGAAAATATTAGCTGTAAAGGTCAT
ACTACTAGATATTACACTGGAACTTCAGAAGCAAATTATGTCTGAATTGGAATTCTTTATAAGTGCGATTCATCA
TATATCATTGGATTTTATGGAGCATTTTTTGTAGAAAACAGGATTTCAATATGTACAGAATTCATGGATGGGGGAT
CTTTGGATGTATATAGGAAAATGCCGAACATGTCCTTGGAAGAATTGCAGTAGCAGTTGTTAAAGGCCTTACTT
ATTGTGGAGTTTAAAGATTTTACATAGAGACGTGAAGCCCTCCAATATGCTAGTAAACACAAGAGGACAGGTTA
AGCTGTGTGATTTTGGAGTTAGCACTCAGCTGGTGAATTCTATAGCCAAGACGTATGTTGGAACAAATGCTTATA
TGGCGCCTGAAAGGATTTCAGGGGAGCAGTATGGAATTCATTCTGATGTCTGGAGCTTAGGAATCTCTTTTATG
GAGCTTGCTCTTGGGAGGTTTCCATATCCTCAGATTCAGAAAAACCAGGGATCTTTAATGCCTCTCCAGCTTCTG
CAGTGCATTGTTGATGAGGATTCGCCCGTCCTTCCAGTTGGAGAGTTCTCGGAGCCATTTGTACATTTCATCAG
TCAGTGTATGCGAAAACAGCCAAAAGAAAGGCCAGCACCTGAAGAATTGATGGGCCACCCGTTCATCGTGCAG
TTCAATGATGGAAATGCCGCCGTGGTGTCCATGTGGGTGTGCCGGGCGCTGGAGGAGAGGCGGAGCCAGCAG
GGGCCCCCG Protein Sequence(Seq ID No. 28):
MLWLALGPFPAMENQVLVIRIKIPNSGAVDWTVHSGPQLLFRDVLDVIGQVLPEATTTAFEYEDEDGDRITVRSDEEM
KAMLSYYYSTVMEQQVNGQLIEPLQIFPPRACKPPGERNIHGLKVNTRAGPSQHSSPAVSDSLPSNSLKKSSAELKKIL
ANGQMNEQDIRYRDTLGHGNGGTVYKAYHVPSGKILAVKVILLDITLELQKQIMSELEILYKCDSSYIIGFYGAFFVENR
ISICTEFMDGGSLDVYRKMPEHVLGRIAVAVVKGLTYLWSLKILHRDVKPSNMLVNTRGQVKLCDFGVSTQLVNSIAK
TYVGTNAYMAPERISGEQYGIHSDVWSLGISFMELALGRFPYPQIQKNQGSLMPLQLLQCIVDEDSPVLPVGEFSEPF
VHFITQCMRKQPKERPAPEELMGHPFIVQFNDGNAAVVSMWVCRALEERRSQQGPP MAGEA4　　　　　P43358　　　　>P001216_CAG_CAGp1_MAGEA4_3103_*Homo sapiens* melanoma antigen
　　　　　　　　　　　　　　　　family A_4_BC017723.1_AAH17723.1_P43358_0_0_054_0_951
Nucleotide Sequence(Seq ID No. 10):
ATGTCTTCTGAGCAGAAGAGTCAGCACTGCAAGCCTGAGGAAGGCGTTGAGGCCCAAGAAGAGGCCCTGGGC
CTGGTGGGTGCACAGGCTCCTACTACTGAGGAGCAGGAGGCTGCTGTCTCCTCCTCCTCTCCTCTGGTCCCTG
GCACCCTGGAGGAAGTGCCTGCTGCTGAGTCAGCAGGTCCTCCCCAGAGTCCTCAGGGAGCCTCTGCCTTAC
CCACTACCATCAGCTTCACTTGCTGGAGGCAAGCCAATGAGGGTTCCAGCAGCCAAGAAGAGGAGGGGGCAA
GCACCTCGCCTGACGCAGAGTCCTTGTTCCGAGAAGCACTCAGTAACAAGGTGGATGAGTTGGCTCATTTTCTG
CTCCGCAAGTATCGAGCCAAGGAGCTGGTCACAAAGGCAGAAATGCTGGAGAGAGTCATCAAAAATTACAAGC
GCTGCTTTCCTGTGATCTTCGGCAAAGCCTCCGAGTCCCTGAAGATGATCTTTGGCATTGACGTGAAGGAAGTG
GACCCCACCAGCAACACCTACACCCTTGTCACCTGCCTGGGCCTTTCCTATGATGGCCTGCTGGGTAATAATCA
GATCTTTCCCAAGACAGGCCTTCTGATAATCGTCCTGGGCACAATTGCAATGGAGGGCGACAGCGCCTCTGAG
GAGGAAATCTGGGAGGAGCTGGGTGTGATGGGGGTGTATGATGGGAGGGAGCACACTGTCTATGGGGAGCCC
AGGAAACTGCTCACCCAAGATTGGGTGCAGGAAAACTACCTGGAGTACCGGCAGGTACCCGGCAGTAATCCTG
CGCGCTATGAGTTCCTGTGGGGTCCAAGGGCTCTGGCTGAAACCAGCTATGTGAAAGTCCTGGAGCATGTGGT
CAGGGTCAATGCAAGAGTTCGCATTGCCTACCCATCCCTGCGTGAAGCAGCTTTGTTAGAGGAGGAAGAGGGA
GTC Protein Sequence(Seq ID No. 29):
MSSEQKSQHCKPEEGVEAQEEALGLVGAQAPTTEEQEAAVSSSSPLVPGTLEEVPAAESAGPPQSPQGASALPTTI
SFTCWRGPNEGSSSQEEEGPSTSPDAESLFREALSNKVDELAHFLLRKYRAKELVTKAEMLERVIKNYKRCFPVIFG
KASESLKMIFGIDVKEVDPASNTYTLVTCLGLSYDGLLGNNQIFPKTGLLIIVLGTIAMEGDSASEEEIWEELGVMGVYD
GREHTVYGEPRKLLTQDWVQENYLEYRQVPGSNPARYEFLWGPRALAETSYVKVLEHVVRVNARVRIAYPSLREAA
LLEEEEGV STAT1　　　　　P42224　　　　>P000068_KIN96_KIN_STAT1_6772_*Homo sapiens* signal trasducer and
　　　　　　　　　　　　　　　　activator of transcription 1 91 kDa transcript
　　　　　　　　　　　　　　　　varian_BC002704.2_AAH02704.1_P42224_93992.15_0_2139_0_2136
Nucleotide Sequence(Seq ID No. 11):
ATGTCTCAGTGGTACGAACTTCAGCAGCTTGACTCAAAATTCCTGGAGCAGGTTCACCAGCTTTATGATGACAG
TTTTCCCATGGAAATCAGACAGTACCTGGCAGAGTGGTTAGAAAAGCAAGACTGGGAGCACGCTGCCAATGAT
GTTTCATTTGCCACCATCCGTTTTCATGACCTCCTGTCACAGCTGGATGATCAATATAGTCGCTTTTCTTTGGAG
AATAACTTCTTGCTACAGCATAACATAAGGAAAAGCAAGCGTAATCTTCAGGATAATTTTCAGGAAGACCCAATC
CAGATGTCTATGATCATTTACAGCTGTCTGAAGGAAGAAAGGAAATTCTGGAAAACGCCCAGAGATTTAATCAG
GCTCAGTCGGGGAATATTCAGAGCACAGTGATGTTAGACAAACAGAAAGAGCTTGACAGTAAAGTCAGAAATGT
GAAGGACAAGGTTATGTGTATAGAGCATGAAATCAAGAGCCTGGAAGATTTACAAGATGAATATGACTTCAAATG
CAAAACCTTGCAGAACAGAGAACACGAGACCAATGGTGTGGCAAAGAGTGATCAGAAACAAGAAACGCTGTTA
CTCAAGAAGATGTATTTAATGCTTGACAATAAGAGAAAGGAAGTAGTTCACAAAATAATAGAGTTGCTGAATGTC
ACTGAACTTACCCAGAATGCCCTGATTAATGATGAACTAGTGGAGTGGAAGCGGAGACAGCAGAGCGCCTGTA
TTGGGGGGCCGCCCAATGCTTGCTTGGATCAGCTGCAGAACTGGTTCACTATAGTTGCGGAGAGTCTGCAGCA
AGTTCGGCAGCAGCTTAAAAAGTTGGAGGAATTGGAACAGAAATACACCTACGAACATGACCCTATCACAAAAA
ACAAACAAGTGTTATGGGACCGCACCTTCAGTCTTTTCCAGCAGCTCATTCAGAGGTCGTTTGTGGTGGAAAGA TABLE 5-continued

| Protein Name | UniprotID | Description |
| --- | --- | --- |

CAGCCCTGCATGCCAACGCACCCTCAGAGGCCGCTGGTCTTGAAGACAGGGGTCCAGTTCACTGTGAAGTTGA
GACTGTTGGTGAAATTGCAAGAGCTGAATTATAATTTGAAAGTCAAAGTCTTATTTGATAAAGATGTGAATGAGA
GAAATACAGTAAAAGGATTTAGGAAGTTCAACATTTTGGGCACGCACACAAAAGTGATGAACATGGAGGAGTCC
ACCAATGGCAGTCTGGCGGCTGAATTTCGGCACCTGCAATTGAAAGAACAGAAAAATGCTGGCACCAGAACGA
ATGAGGGTCCTCTCATCGTTACTGAAGAGCTTCACTCCCTTAGTTTTGAAACCCAATTGTGCCAGCCTGGTTTG
GTAATTGACCTCGAGACGACCTCTCTGCCCGTTGTGGTGATCTCCAACGTCAGCCAGCTCCCGAGCGGTTGGG
CCTCCATCCTTTGGTACAACATGCTGGTGGCGGAACCCAGGAATCTGTCCTTCTTCCTGACTCCACCATGTGCA
CGATGGGCTCAGCTTTCAGAAGTGCTGAGTTGGCAGTTTTCTTCTGTCACCAAAAGAGGTCTCAATGTGGACCA
GCTGAACATGTTGGGAGAGAAGCTTCTTGGTCCTAACGCCAGCCCCGATGGTCTCATTCCGTGGACGAGGTTT
TGTAAGGAAAATATAAATGATAAAAATTTTCCCTTCTGGCTTTGGATTGAAAGCATCCTAGAACTCATTAAAAAAC
ACCTGCTCCCTCTCTGGAATGATGGGTGCATCATGGGCTTCATCAGCAAGGAGCGAGAGCGTGCCCTGTTGAA
GGACCAGCAGCCGGGGACCTTCCTGCTGCGGTTCAGTGAGAGCTCCCGGGAAGGGGCCATCACATTCACATG
GGTGGAGCGGTCCCAGAACGGAGGCGAACCTGACTTCCATGCGGTTGAACCCTACACGAAGAAGAACTTTCT
GCTGTTACTTTCCCTGACATCATTCGCAATTACAAAGTCATGGCTGCTGAGAATATTCCTGAGAATCCCCTGAAG
TATCTGTATCCAAATATTGACAAAGACCATGCCTTTGGAAAGTATTACTCCAGGCCAAAGGAAGCACCAGAGCC
AATGGAACTTGATGGCCCTAAAGGAACTGGATATATCAAGACTGAGTTGATTTCTGTGTCTGAAGTG

Protein Sequence(Seq ID No. 30):
MSQWYELQQLDSKFLEQVHQLYDDSFPMEIRQYLAQWLEKQDWEHAANDVSFATIRFHDLLSQLDDQYSRFSLEN
NFLLQHNIRKSKRNLQDNFQEDPIQMSMIIYSCLKEERKILENAQRFNQAQSGNIQSTVMLDKQKELDSKVRNVKDKV
MCIEHEIKSLEDLQDEYDFKCKTLQNREHETNGVAKSDQKQEQLLLKKMYLMLDNKRKEVVHKIIELLNVTELTQNALI
NDELVEWKRRQQSACIGGPPNACLDQLQNWFTIVAESLQQVRQQLKKLEELEQKYTYEHDPITKNKQVLWDRTFSL
FQQLIQSSFVVERQPCMPTHPQRPLVKTGVQFTVKLRLLVKLQELNYNLKVKVLFDKDVNERNTVKGFRKFNILGTH
TKVMNMEESTNGSLAAEFRHLQLKEQKNAGTRTNEGPLITEELHSLSFETQLCQPGLVIDLETTSLPVVVISNVSQL
PSGWASILWYNMLVAEPRNLSFFLTPPCARWAQLSEVLSWQFSSVTKRGLNVDQLNMLGEKLLGPNASPDGLIPWT
RFCKENINDKNFPFWLWIESILELIKKHLLPLWNDGCIMGFISKERERALLKDQQPGTFLLRFSESSREGAITFTWVER
SQNGGEPDFHAVEPYTKKELSAVTFPDIIRNYKVMAAENIPENPLKYLYPNIDKDHAFGKYYSRPKEAPEPMELDGPK
GTGYIKTELISVSEV CT47A1            Q5JQC4         >P003099_Q211_Q211_tube_CT47A1_728096_0_NM_001080146.1_0_Q5JQC4_0_Insert
                                          sequence is gene optimized by GeneArt_0_0_0
Nucleotide Sequence(Seq ID No. 12):
ATGTCCGCTACCGGCGACCGTCACCCTACCCAGGGCGACCAAGAGGCTCCCGTGTCCCAAGAGGGTGCTCAG
GCTGAGGCTGCTGGTGCTGGCAACCAGGAAGGTGGCGACTCCGGTCCCGACTCCTCCGACGTGGTGCCTGCT
GCTGAGGTCGTGGGTGTCGCTGGTCCTGTCGAGGGCCTGGGAGAGGAAGAGGGCGAGCAGGCTGCTGGCCT
GGCTGCTGTGCGTCGTGGTGGTTCCGCTGAAGAGGACTCCGACATCGGTCCCGCTACCGAGGAAGAGGAAGA
AGAAGAGGGCAACGAGGCTGCTAACTTCGACCTGGCTGTGGTGGCTCGTCGTTACCCCGCTTCCGGTATCCAC
TTCGTGCTGCTGGACATGGTGCACTCCCTGCTGCACCGTCTGTCCCACAACGACCACATCCTGATCGAGAACC
GTCAGCTGTCCCGTCTGATGGTCGGACCCCACGCTGCTGCTCGTAACCTGTGGGGCAACCTGCCCCCCCTGC
TGCTGCCTCAACGTCTGGGAGCTGGTGCTGCTGCTAGGGCTGAGGGGACTGGGCCTGATCCAAGAGGCTG
CTTCCGTGCCCGAGCCCGCTGTGCCTGCTGACTTGGCTGAGATGGCCCGCGAGCCTGCTGAGGAAGCTGCTG
AAGAGAAGCTGTCCGAGGAAGCCACCGAGGAACCCGACGCTGAGGAACCAGCTACTGAGGAACCCACCGCTC
AAGAGAAGCTGTCCGAGGAAGCCACCGAGGAACCCGACGCTGAGGAACCAGCTACTGAGGAACCCACCGCTC
CTGGCGAGGAAGAGAAGGAACAAGAAAAGGAAAAGGACGCCGAGAACAAGGTCAAGAACTCCAAGGGCACC Protein Sequence(Seq ID No. 31):
MSATGDRHPTQGDQEAPVSQEGAQAEAAGAGNQEGGDSGPDSSDVVPAAEVVGVAGPVEGLGEEEGEQAAGLA
AVPRGGSAEEDSDIGPATEEEEEEEGNEAANFDLAVVARRYPASGIHFVLLDMVHSLLHRLSHNDHILIENRQLSRLM
VGPHAAARNLWGNLPPLLLPQRLGAGAAARAGEGLGLIQEAASVPEPAVPADLAEMAREPAEEAAEEKLSEEATEE
PDAEEPATEEPTAQEATAPEEVTKSQPEKWDEEAQDAAGEEEKEQEKEKDAENKVKNSKGT IGF2BP3        O00425         >P003224_Q311_Q311_tube_IGF2BP3_10643_0_NM_006547.2_0_O00425_0_Insert
                                          sequence is gene optimized by GeneArt_0_0_0
Nucleotide Sequence(Seq Id No. 13):
ATGAACAAGCTGTACATCGGCAACCTGTCCGAGAACGCTGCTCCCTCCGACCTCGAGTCCATCTTCAAGGACG
CTAAGATCCCCGTGTCCGGACCCTTCCTGGTCAAGACCGGTTACGCTTTCGTGGACTGCCCCGACGAGTCCTG
GGCTCTGAAGGCTATCGAGGCTCTGTCCGGCAAGATCGAGCTGCACGGCAAGCCCATCGAGGTCGAGCACTC
CGTGCCCAAGCGTCAGCGTATCCGCAAGCTGCAGATCCGTAACATCCCCCCACACCTCCAGTGGGAGGTGCT
GGACTCCCTGCTGGTGCAGTACGGTGTCGTCGAGTCCTGCGAGCAAGTGAACACCGACTCCGAGACTGCTGT
GGTCAACGTGAGCTACTCCTCCAAGGACCAGGCTCGTCAGGCTCTGGACAAGCTGAACGGTTTCCAGCTCGAG
AACTTCACCCTGAAGGTGGCCTACATCCCCGACGAGATGGCTGCTCAGCAGACCCCCTGCAGCAGCCCCGT
GGTCGTCGTGGACTGGGACAGCGTGGTAGCTCCCGTCAGGGTTCCCCGGTTCCGTGTCCAAGCAGAAGCCC
TGCGACCTGCCCCCTGCGTCTGCTGGTGCCTACCCAGTTCGTGGGTGCTATCATCGGCAAGGAAGGTGCTACCA
TCCGCAACATCACCAAGCAGACCCAGTCCAAGATCGACGTCCACCGCAAGGAAAACGCTGGCGCTGCTGAGAA
GTCCATCACCATCCTGTCCACCCCCGAGGGCACCTCCGGCTGCTTCATCTTCTCGAGATCATGCACAAG
GAAGCCCAGGACATCAAGTTCACCGAGGAAATCCCCCTGAAGATCCTGGCTCACAACAACTTCGTGGGTCGTC
TGATCGGAAAGGAAGGCCGTAACCTGAAGAAGATCGAGCAGGACACCGACACCAAGATCACCATCTCCCCACT
GCAAGAGCTGACCCTGTACAACCCCGAGCGTACCATCACCGTGAAGGGCAACGTGGAAACCTGCGCTAAGGC
TGAAGAGAAAATCATGAAGAAGATCCGCGAGTCCTACGAGAACGATATCGCTTCCATGAACCTGCAGGCTCAC
CTGATCCCCGGCCTGAACCTGAACGCTCTGGGCCTGTTCCCCCCTACCTCCGGCATGCCTCCTCCCACCTCTG
GTCCCCCCTCCGCTATGACCCCCCCATACCCCCAGTTCGAGCAGTCCGAGACTGAGACTGTGCACCTGTTCAT
CCCCGCTCTGTCCGTCGGTGCCATCATCGGAAAGCAGGGCCAGCACATCAAGCAGCTGTCCCGTTTCGCTGGT
GCTTCCATCAAGATCGCTCCCGCTGAGGCTCCCGACGCTAAGGTCCGCATGGTCATCATCACCGGTCCCCCCG
AGGCTCAGTTCAAGGCTCAGGGTCGTATCTACGGCAAGATCAAGGAAGAGAACTTCGTCAGCCCCAAGGAAGA
AGTGAAGCTCGAGGCTCACATCCGTGTGCCATCCTTCGCTGCTGGTCGTGTTATCGGCAAGGGTGGCAAGACC
GTGAACGAGCTGCAGAACCTGTCCTCCGCTGAGGTGGTGGTGCCCCGTGACCAGACCCCTGACGAGAACGAC
CAGGTGGTGGTCAAGATCACCGGTCACTTCTACGCTTGCCAGGTGGCCCAGCGCAAGATCCAAGAGATCCTGA
CCCAAGTGAAGCAGCACCAGCAGCAGAAGGCTCTGCAGTCCGGTCCCCCTCAGTCCCGTCGCAAG TABLE 5-continued

| Protein Name | UniprotID | Description |
| --- | --- | --- |

Protein Sequence(Seq ID No. 32):
MNKLYIGNLSENAAPSDLESIFKDAKIPVSGPFLVKTGVAFVDCPDESWALKAIEALSGKIELHGKPIEVEHSVPKRQRI
RKLQIRNIPPHLQWEVLDSLLVQYGVVESCEQVNTDSETAVVNVTYSSKDQARQALDKLNGFQLENFTLKVAYIPDE
MAAQQNPLQQPRGRRGLGQRGSSRQGSPGSVSKQKPCDLPLRLLVPTQFVGAIIGKEGATIRNITKQTQSKIDVHRK
ENAGAAEKSITILSTPEGTSAACKSILEIMHKEAQDIKFTEEIPLKILAHNNFVGRLIGKEGRNLKKIEQDTDTKITISPLQE
LTLYNPERTITVKGNVETCAKAEEEIMKKIRESYENDIASMNLQAHLIPGLNLNALGLFPPTSGMPPPTSGPPSAMTPP
YPQFEQSETETVHLFIPALSVGAIIGKQGQHIKQLSRFAGASIKIAPAEAPDAKVRMVIITGPPEAQFKAQGRIYGKIKEE
NFVSPKEEVKLEAHIRVPSFAAGRVIGKGGKTVNELQNLSSAEVVVPRDQTPDENDQVVVKITGHFYACQVAQRKIQ
EILTQVKQHQQQKALQSGPPQSRRK CTAG2                O75638        >P001440_CAG_CAGp2_CTAG2_30848_*Homo sapiens* cancer/testis antigen
                                   2 transcript variant 2_BC002833.2_AAH02833.1_O75638_0_0_633_0_630
Nucleotide Sequence(Seq ID No. 14):
ATGCAGGCCGAAGGCCGGGGCACAGGGGGTTCGACGGGCGATGCTGATGGCCCAGGAGGCCCTGGCATTCC
TGATGGCCCAGGGGGCAATGCTGGCGGCCCAGGAGAGGCGGGTGCCACGGGCGGCAGAGGTCCCCGGGGC
GCAGGGGCAGCAAGGGCCTCGGGGCCGAGAGGAGGCGCCCCGCGGGGTCCGCATGGCGGTGCCGCTTCTG
CGCAGGATGGAAGGTGCCCCTGCGGGGCCAGGAGGCCGGACAGCCGCCTGCTTGAGTTGCACATCACGATG
CCTTTCTCGTCGCCCATGGAAGCGGAGCTGGTCCGCAGGATCCTGTCCCGGGATGCCGCACCGCTCCCCCGA
CCAGGGGCGGTTCTGAAGGACTTCACCGTGTCCGGCAACCTACTGTTTATGTCAGTTCGGGACCAGGACAGGG
AAGGCGCTGGGCGGATGAGGGTGGTGGGTTGGGGGCTGGGATCCGCCTCCCCGGAGGGGCAGAAAGCTAGA
GATCTCAGAACACCCAAACACAAGGTCTCAGAACAGAGACCTGGTACACCAGGCCCGCCGCCACCCGAGGGA
GCCCAGGGAGATGGGTGCAGAGGTGTCGCCTTTAATGTGATGTTCTCTGCCCCTCACATT Protein Sequence(Seq ID No. 33):
MQAEGQGTGGSTGDADGPGGPGIPDGPGGNAGGPGEAGATGGRGPRGAGAARASGPRGGAPRGPHGGAASAQ
DGRCPCGARRPDSRLLQLHITMPFSSPMEAELVRRILSRDAAPLPRPGAVLKDFTVSGNLLFMSVRDQDREGAGRM
RVVGWGLGSASPEGQKARDLRTPKHKVSEQRPGTPGPPPPEGAQGDGCRGVAFNVMFSAPHI RAD23B               P54727        >P00309_SIG_SIG1-1_RAD23B_5887_*Homo sapiens* RAD23 homolog B (*S.*
                                   *cerevisiae*)_BC020973.2_AAH20973.1_P54727_54173_0_1230_0_1227
Nucleotide Sequence(Seq ID No. 15):
ATGCAGGTCACCCTGAAGACCCTCCAGCAGCAGACCTTCAAGATAGACATTGACCCCGAGGAGACGGTGAAAG
CACTGAAAGAGAAGATTGAATCTGAAAAGGGGAAAGATGCCTTTCCAGTAGCAGGTCAAAAATTAATTTATGCA
GGCAAAATCCTCAATGATGATACTGCTCTCAAAGAATATAAAATTGATGAGAAAAACTTTGTGGTGGTTATGGTG
ACCAAACCCAAAGCAGTGTCCACACCAGCACCAGCTACAACTCAGCAGTCAGTCCTGCCAGCACTACAGCAG
TTACTTCCTCCACCACCACAACTGTGGCTCAGGCTCCAACCCCTGTCCCTGCCTTGGCCCCCACTTCCACACCT
GCATCCATCACTCCAGCATCAGCGACAGCATCTTCTGAACCTGCACCTGCTAGTGCAGCTAAACAAGAGAAGCC
TGCAGAAAAGCCAGCACAGACACCAGTGGCTACTAGCCCAACAGCAACTGACAGTACATCGGGTGATTCTTCT
CGGTCAAACCTTTTGAAGATGCAACGAGTGCACTTGTGACGGGTCAGTCTTTACGAGAAATATGGTAACTGAGAT
CATGTCAATGGGCTATGAACGAGAGCAAGTAATTGCAGCCCTGAGAGCCAGTTTCAACAACCCTGACAGAGCA
GTGGAGTATCTTTTAATGGGAATCCCTGGAGATAGAGAAAGTCAGGCTGTGGTTGACCCCCCTCAAGCAGCTA
GTACTGGGGTTCCTCAGTCTTCAGCAGTGGCTGCAGCTGCAGCAACTACGACAGCAACAACTACAACAACAAG
TTCTGGAGGACATCCCCTTGAATTTTTACGGAATCAGCCTCAGTTTCAACAGATGAGACAAATTATTCAGCAGAA
TCCTTCCTTGCTTACTACAGCAGATAGGTCAGGAGAATCCTCAATTACTTCAGCAAATTAGCCAACA
CCAGGAGCATTTTATTCAGATGTTAAATGAACCAGTTCAAGAAGCTGGTGGTCAAGGAGGAGGAGGTGGAGGT
GGCAGTGGAGGAATTGCAGAAGCTGGAAGTGGTCATATGAACTACATTCAAGTAACACCTCAGGAAAAAGAAG
CTATAGAAAGGTTAAAGGCATTAGGATTTCCTGAAGGACTTGTGATACAAGCGTATTTTGCTTGTGAGAAGAATG
AGAATTTGGCTGCCAATTTTCTTCTACAGCAGAACTTTGATGAAGAT Protein Sequence(Seq ID No. 34):
MQVTLKTLQQQTFKIDIDPEETVKALKEKIESEKGKDAFPVAGQKLIYAGKILNDDTALKEYKIDEKNFVVVMVTKPKAV
STPAPATTQQSAPASTTAVTSSTTTTVAQAPTPVPALAPTSTPASITPASATASSEPAPASAAKQEKPAEKPAETPVA
TSPTATDSTSGDSSRSNLFEDATSALVTGQSYENMVTEIMSMGYEREQVIAALRASFNNPDRAVEYLLMGIPGDRES
QAVVDPPQAASTGAPQSSAVAAAATTATTTTTSSGGHPLEFLRNQPQFQQMRQIIQQNPSLLPALLQQIGRENPQ
LLQQISQHQEHFIQMLNEPVQEAGGQGGGGGGGSGGIAEAGSGHMNYIQVTPQEKEAIERLKALGFPEGLVIQAYFA
CEKNENLAANFLLQQNFDED FADD                 Q13158        >P000417_SIG_SIG1-2_FADD_8772_*Homo sapiens* Fas (TNFRSF6)-
                                   associated via death
                                   domain_BC000334.2_AAH00334.1_Q13158_34265.45_0_627_0_624
Nucleotide Sequence(Seq ID No. 16):
ATGGACCCGTTCCTGGTGCTGCTGCACTCGGTGTCGTCCAGCCTGTCGAGCAGCGAGCTGACCGAGCTCAAG
TTCCTATGCCTCGGGCGCGTGGGCAAGCGCAAGCTGGAGCGCGTGCAGAGCGGCCTAGACCTCTTCTCCATG
CTGCTGGAGCAGAACGACCTGGAGCCCGGGCACACCGAGCTCCTGCGCGAGCTGCTGCCTCCCTGCGGCG
CCACGACCTGCTGCGGCGCGTCGACGACTTCGAGGCGGGGCGGCGGCCGGGGCCGCGCCTGGGGAAGAA
GACCTGTGTGCAGCATTTAACGTCATATGTGATAATGTGGGGAAAGATTGGAGAAGGCTGGCTCGTCAGCTCAA
AGTCTCAGACACCAAGATCGACAGCATCCAGGACAGATACCCCCGCAACCTGACAGAGCGTGTGCGGGAGTC
ACTGAGAATCTGGAAGAACACAGAGAAGGAGAACGCAACAGTGGCCCACCTGGTGGGGGGCTCTCAGGTCCTG
CCAGATGAACCTGGTGGCTGACCTGGTACAAGAGGTTCAGCAGGCCCGTGACCTCCAGAACAGGAGTGGGGC
CATGTCCCCGATGTCATGGAACTCAGACGCATCTACCTCCGAAGCGTCC TABLE 5-continued

| Protein Name | UniprotID | Description |
|---|---|---|

Protein Sequence(Seq ID No. 35):
MDPFLVLLHSVSSSLSSSELTELKFLCLGRVGKRKLERVQSGLDLFSMLLEQNDLEPGHTELLRELLASLRRHDLLRR
VDDFEAGAAAGAAPGEEDLCAAFNVICDNVGKDWRRLARQLKVSDTKIDSIEQRYPRNLTERVRESLRIWKNTEKEN
ATVAHLVGALRSCQMNLVADLVQEVQQARDLQNRSGAMSPMSWNSDASTSEAS

| PTPN20A | Q4JDL3 | >P003090_Q211_Q211_tube)PTPN20A_653129_0_NM_001042387.1_0_Q4JDL3_0_Insert sequence is gene optimized by GeneArt_0_0_0 |
|---|---|---|

Nucleotide Sequence(Seq ID No. 17):
ATGTCCTCCCCCGTGACTTCCGTGCTGAGCCCGTGAACGACTACGAGGGCAACGACTCCGAGGCTGAGGAC
CTGAACTTCCGTGAAACCCTGCCCTCCAGCTCCCAAGAGAACCACCCCCCGTTCCAAGGTGTTCGAGAACAAGG
TCAACTCCGAGAAGGTCAAGCTGTCCCTGCGCAACTTCCCCCCACAACGATTACGAGGACGTGTTCGAGGAACC
CTCCGAGTCCGGTTCCGACCCCTCCATGTGGACCGCTCGTGGTCCCTTCCGTCGTGACCGTTGGTCCTCCGAG
GACGAGGAAGCTGCTGGACCCTCCCAGGCTCTGTCCCCCCTGCTGTCCGACACCCGCAAGATCGTGTCCGAG
GGCGAGCTGGACCAGCTGGCTCAGATCCGTGCCCTGATCTTCAACTTCCACGAGCAGACCGCTATCAAGGACT
GCCTGAAGATCCTCGAGGAAAAGACCGCTGCTTACGACATCATGCAAGAGTTCATGGCTCTCGAGCTGAAGAA
CCTGCCCGGCGAGTTCAACTCCGGCAACCAGCCCTCCAACCGCGAGAAGAACCGTTACCGTGACATCCTGCCT
TTCCAGCACCACGGTTACTCCGGTCCCAACGAGCGTACCACCTTCTGGCACGGTTCCAACGAGGGTGCTGTGT
CCCTGCTGCTGCGCTACTGCGCT Protein Sequence(Seq ID No. 36):
MSSPRDFRAEPVNDYEGNDSEAEDLNFRETLPSSSQENTPRSKVFENKVNSEKVKLSLRNFPHND¥EDVFEEPSES
GSDPSMWTARGPFRRDRWSSEDEEAAGPSQALSPLLSDTRKIVSEGELDQLAQIRPLIFNFHEQTAIKDCLKILEEKT
AAYDIMQEFMALELKNLPGEFNSGNQPSNREKNRYRDILPYDSTRVPLGKSKDYINASYIRIVNCGEEYFYIATQGPLL
STIDDFWQMVLENNSNVIAMITREIEGGIIKCYHYWPISLKKPLELKHFRVFLENYQILQYFIIRMFQVVEKSTGTSHSVK
QLQFTKWPDHGTPASADSFIKYIRYARKSHLTGPMVVHCSAGIGRTGVFLCVDVVFCAIVKNCSFNIMDIVAQMREQ
RSGMVQTKEQYHFCYDIVLEVLRKLLTLD

| TPM1 | P09493 | >P001454_CAG_CAGp2_TPM1_7168_Homo sapiens_ tropomyosin 1 (alpha)_BC007433_2_AAH07433.1_P09493_0_0_855_0_852 |
|---|---|---|

Nucleotide Sequence(Seq ID No. 18):
ATGGACGCCATCAAGAAGAAGATGCAGATGCTGAAGCTCGACAAGGAGAACGCCTTGGATCGAGCTGAGCAG
GCGGAGGCCGACAAGAAGGCGGCGGAAGACAGGAGCAAGCAGCTGGAAGATGAGCTGGTGTCACTGCAAAA
GAAACTCAAGGGCACCGAAGATGAACTGGACAAATATTCTGAGGCTCTCAAAGATGCCCAGGAGAAGCTGGAG
CTGGCAGAGAAAAAGGCCACCGATGCTGAAGCCGACGTAGCTTCTCTGAACAGACGCATCCAGCTGGTTGAGG
AAGAGTTGGATCGTGCCCAGGAGCGTCTGGCAACAGCTTTGCAGAAGCTGGAGGAAGCTGAGAAGGCAGCAG
ATGAGAGTGAGAGAGGCATGAAAGTCATTGAGAGTCGAGCCCAAAAAGATGAAGAAAAATGGAAATTCAGGA
GATCCAACTGAAAGAGGCAAAGCACATTGCTGAAGATGCCGACCGCAAATATGAAGAGGTGGCCCGTAAGCTG
GTCATCATTGAGAGCGACCTGGAACGTGCAGAGGAGCGGGCTGAGCTCTCAGAAGGCCAAGTCCGACAGCTG
GAAGAACAATTAAGAATAATGGATCAGACCTTGAAAGCATTAATGGCTGCAGAGGATAAGTACTCGCAGAAGGA
AGACAGATATGAGGAAGAGATCAAGGTCCTTTCCGACAAGCTGAAGGAGGCTGAGACTCGGGCTGAGTTTGCG
GAGAGGTCAGTAACTAAATTGGAGAAAAGCATTGATGACTTAGAAGACGAGCTGTACGCTCAGAAACTGAAGTA
CAAAGCCATCAGCGAGGAGCTGGACCACGCTCTCAACGATATGACTTCCATG Protein Sequence(Seq ID No. 37):
MDAIKKKMQMLKLDKENALDRAEQAEADKKAAEDRSKQLEDELVSLQKKLKGTEDELDKYSEALKDAQEKLELAEKK
ATDAEADVASLNRRIQLVEEELDRAQERLATALQKLEEAEKAADESERGMKVIESRAQKDEEKMEIQEIQLKEAKHIA
EDADRKYEEVARKLVIIESDLERAEERAELSEGKCAELEEELKTVTNNLKSLEAQAEKYSQKEDRYEEEIKVLSDKLKE
AETRAEFAERSVTKLEKSIDDLEDELYAQKLKYKAISEELDHALNDMTSI

| CTAG1A | P78358 | >P003024_Q211_Q211_tube_CTAG1A_246100_0_NM_139250.1_0_P78358_0_Insert sequence is gene optimized by GeneArt_0_0_0 |
|---|---|---|

Nucleotide Sequence(Seq ID No. 19):
ATGCAGGCTGAGGGTCGTGGCACCGGTGGTTCCACTGGCGACGCTGACGGTCCCGGTGGTCCTGGTATCCCC
GACGGTCCTGGTGGCAACGCTGGTGGTCCAGGCGAGGCTGGTGCTACCGGTGGTCGTGGTCCTCGTGGTGCT
GGTGCTGCTCGTGCTTCCGGTCCAGGTGGTGGTGCTCCCCGTGGTCCTCACGGTGGTGCTGCTTCCGGCCTG
AACGGTTGCTGCCGTTGCGGTGCTCGCGGTCCCGAGTCCCGTCTGCTCGAGTTCTACCTGGCTATGCCCTTCG
CTACCCCTATGGAAGCTGAGCTGGCTCGTCGTTCCCTGGCTCAGGACGCTCCTCCTCTGCCCGTGCCCGGTGT
CCTGCTGAAGGAGTTCACTGTCTCCGGCAACATCCTGACCATCCGTCTGACCGCTGCTGACCACCGTCAGCTC
CAGCTGTCCATCTCCTCATGCCTGCAGCAGCTGTCCCTGCTGATGTGGATCACCCAGTGTTTCTTGCCCGTGTT
GGTGGCTCAGCCCCCCTCCGGTCAACGTCGT Protein Sequence(Seq ID No. 38):
MQAEGRGTGGSTGDADGPGGPGIPDGPGGNAGGPGEAGATGGRGPRGAGAARASGPGGGAPRGPHGGAASGL
NGCCRCGARGPESRLLEFYLAMPFATPMEAELARRSLAQDAPPLPVPGVLLKEFTVSGNILTSRLTAADHRQLQLSIS
SCLQQLSLLMWITQCFLPVFLAQPPSGQRR

---

TABLE 6

Normalised RFU values for the 19 biomarkers

| Protein | CT47A1 | CTAG1A | CTAG2 | DDX43 | DDX53 | FADD | GAGE1 | GAGE2C |
|---|---|---|---|---|---|---|---|---|
| Control1_021608 | 1509.358 | 1665.573 | 1625.151 | 2051.253 | 2063.69 | 2342.416 | 1936.961 | 2921.207 |
| Control1_021611 | 744.8538 | 840.2482 | 689.2973 | 1011.785 | 1008.013 | 1106.472 | 1000.557 | 905.3507 |
| Control1_021630 | 2308.622 | 2320.635 | 3698.177 | 2686.878 | 2394.465 | 4457.038 | 2656.298 | 1767.186 |

TABLE 6-continued

| | | | Normalised RFU values for the 19 biomarkers | | | | |
|---|---|---|---|---|---|---|---|
| Control1_021631 | 1648.979 | 1653.373 | 2014.062 | 1947.228 | 1745.636 | 3154.698 | 1963.353 | 2408.739 |
| Control1_021642 | 1908.076 | 2463.134 | 2466.247 | 2669.508 | 2731.679 | 3765.574 | 2711.856 | 2790.404 |
| Control1_021643 | 903.8178 | 1280.729 | 1094.733 | 1480.856 | 1737.577 | 1901.206 | 1653.898 | 1536.486 |
| Control1_021650 | 2268.797 | 2064.734 | 3027.739 | 1922.742 | 1862.127 | 6656.163 | 1702.062 | 1538.051 |
| Control1_021660 | 1646.455 | 1641.704 | 2635.412 | 2104.055 | 2228.304 | 2471.875 | 2434.567 | 2913.973 |
| Control1_021661 | 1813.748 | 2232.638 | 1907.396 | 3502.799 | 3281.528 | 2910.518 | 3433.232 | 2851.365 |
| Control1_021663 | 7361.666 | 1747.892 | 1808.937 | 3356.196 | 2994.698 | 2869.315 | 2993.111 | 2762.496 |
| Control1_021674 | 1065.267 | 1391.603 | 1352.962 | 2290.515 | 2156.563 | 2278.898 | 2439.543 | 1912.377 |
| Control1_021679 | 1154.795 | 956.4944 | 1118.479 | 1632.494 | 1530.023 | 2318.788 | 1627.435 | 1436.882 |
| Control1_021680 | 3498.123 | 1930.224 | 1855.749 | 2352.687 | 2406.267 | 2802.602 | 2489.483 | 2315.313 |
| Control1_021681 | 8854.106 | 8411.776 | 8780.085 | 4507.529 | 18451.28 | 9194.071 | 4543.1 | 3534.392 |
| Control1_021682 | 1968.383 | 1557.664 | 1865.677 | 2790.045 | 2426.774 | 2398.539 | 2494.837 | 2171.401 |
| Control2_021005 | 19062.75 | 18286.29 | 21721.06 | 7277.07 | 7509.16 | 21723.39 | 8024.274 | 7810.164 |
| Control2_021007 | 3700.532 | 4218.712 | 3151.603 | 4712.313 | 3869.997 | 4623.076 | 2852.438 | 2929.432 |
| Control2_021016 | 2798.772 | 1907.347 | 2099.19 | 2252.848 | 2179.747 | 3351.127 | 2478.487 | 1937.812 |
| Control2_021017 | 1753.571 | 1402.848 | 1540.14 | 1802.829 | 1780.391 | 2588.142 | 1590.338 | 1678.784 |
| Control2_021025 | 1559 | 2078.736 | 1612.691 | 2155.411 | 2566.253 | 2697.4 | 2064.229 | 1783.645 |
| Control2_021037 | 1640.906 | 1349.049 | 1760.375 | 1917.732 | 2594.986 | 2383.889 | 1833.83 | 1568.244 |
| Control2_021038 | 1296.442 | 1068.401 | 1352.522 | 1510.341 | 1483.263 | 1730.292 | 1498.059 | 1215.978 |
| Control2_021045 | 1755.101 | 1821.33 | 1657.713 | 2107.653 | 2190.138 | 2525.574 | 2252.285 | 1949.365 |
| Control2_021046 | 2544.023 | 3285.646 | 3830.951 | 3493.117 | 4036.784 | 3754.021 | 2887.819 | 2281.996 |
| Control2_021401 | 1790.79 | 2078.056 | 1554.37 | 2146.542 | 2368.271 | 2731.86 | 2223.912 | 2136.282 |
| Control2_021405 | 1633.525 | 1266.149 | 1722.513 | 1767.528 | 1695.027 | 2204.463 | 1972.807 | 1588.648 |
| Control2_021406 | 1231.18 | 1052.587 | 1221.755 | 1492.635 | 1419.205 | 1617.316 | 1516.808 | 1242.477 |
| Control2_021419 | 1161.514 | 969.2148 | 1340.876 | 1298.33 | 1271.956 | 1791.68 | 1169.562 | 1080.648 |
| Control2_021420 | 1134.712 | 1149.875 | 1308.413 | 1473.83 | 1407.462 | 1798.174 | 1488.179 | 1345.406 |
| Control2_021423 | 2775.048 | 2484.158 | 3319.35 | 3998.832 | 3444.215 | 5014.536 | 2747.573 | 2749.234 |
| Control2_021426 | 1832.683 | 3149.643 | 3941.681 | 3331.141 | 3193.393 | 8540.402 | 2683.709 | 2773.037 |
| Control2_021430 | 1740.691 | 1262.074 | 1439.203 | 1784.948 | 1981.945 | 2212.359 | 1632.47 | 1614.165 |
| Control2_021436 | 1238.38 | 1622.209 | 1339.236 | 1766.58 | 1570.416 | 1970.871 | 1839.317 | 6397.377 |
| Control2_021451 | 2114.425 | 1537.93 | 2366.879 | 2916.57 | 2079.048 | 3845.347 | 2548.36 | 2707.548 |
| Control2_021453 | 1618.877 | 1772.711 | 1704.868 | 2010.795 | 1923.692 | 2306.765 | 1938.773 | 1756.808 |
| Control2_021454 | 1238.661 | 1215.827 | 1245.483 | 1523.407 | 1445.537 | 1949.649 | 1606.287 | 1406.954 |
| Control2_021455 | 2118.806 | 2056.799 | 2135.804 | 2460.721 | 2409.344 | 3278.959 | 2368.928 | 2369.251 |
| Control2_021463 | 3277.456 | 2954.683 | 6329.681 | 4028.11 | 3885.942 | 8013.651 | 3643.477 | 3340.58 |
| Control2_021470 | 1404.397 | 1243.895 | 1509.513 | 1683.949 | 1605.746 | 2041.225 | 1716.442 | 1589.304 |
| Control2_021477 | 3228.131 | 2485.288 | 2693.976 | 3065.942 | 3048.999 | 4125.412 | 2669.848 | 2729.497 |
| Control2_021478 | 2702.577 | 2203.357 | 3179.785 | 2097.886 | 1878.866 | 3515.833 | 1795.588 | 1763.884 |
| Control2_021484 | 1867.657 | 1752.908 | 1825.902 | 2021.439 | 1897.227 | 4221.542 | 2058.948 | 1997.38 |
| Control2_021494 | 1226.113 | 1187.936 | 1371.995 | 1461.011 | 1289.884 | 1730.896 | 1411.166 | 1264.948 |
| Control2_021495 | 7510.731 | 6547.905 | 8569.185 | 9460.011 | 24887.84 | 11979 | 7132.448 | 8605.022 |
| Control2_021497 | 2103.323 | 2325.289 | 2423.39 | 2140.501 | 1881.936 | 2612.635 | 1915.289 | 1828.612 |
| Control2_021801 | 1684.077 | 1614.954 | 1535.561 | 2231.253 | 1987.477 | 1996.131 | 2130.707 | 1799.308 |
| Control2_021802 | 1196.061 | 1161.766 | 1299.801 | 1585.175 | 1516.791 | 1907.229 | 1876.651 | 1209.1 |
| Control2_021804 | 1813.897 | 1627.858 | 1980.221 | 2420.979 | 2252.938 | 2496.24 | 2142.618 | 1722.867 |
| Control2_021805 | 1823.253 | 1975.388 | 1764.159 | 1876.648 | 2049.388 | 2313.581 | 1586.62 | 1558.38 |
| Control2_021806 | 3227.12 | 2526.679 | 3146.424 | 3098.552 | 2464.066 | 3832.353 | 2866.158 | 2476.056 |
| Control2_021809 | 7768.215 | 1240.79 | 1653.211 | 1662.744 | 1754.941 | 2201.225 | 1664.758 | 1504.47 |
| Control2_021810 | 2441.267 | 2074.878 | 2048.36 | 2517.456 | 2467.174 | 2497.116 | 2520.784 | 2145.236 |
| Control2_021811 | 2362.442 | 1943.874 | 2300.76 | 1417.942 | 1302.352 | 2023.503 | 1786.874 | 2726.91 |
| Control2_021812 | 3601.507 | 3159.063 | 3554.258 | 4238.192 | 3735.361 | 4730.045 | 3681.06 | 3574.706 |
| Control2_021818 | 1212.13 | 1505.043 | 1698.016 | 2248.258 | 17693.85 | 3775.838 | 1669.632 | 1509.442 |
| Control2_021822 | 1783.632 | 3716.23 | 1896.898 | 2328.595 | 2554.369 | 4283.265 | 2294.682 | 2177.366 |
| Control2_021823 | 1099.564 | 2210.086 | 1106.176 | 1579.562 | 2073.087 | 2047.938 | 1886.623 | 1732.564 |
| Control2_021824 | 5689.149 | 3643.473 | 5707.856 | 2441.248 | 1596.983 | 7271.611 | 2337.595 | 1735.312 |
| Control2_021825 | 1927.505 | 1370.127 | 1906.145 | 2845.125 | 2542.267 | 3858.186 | 2619.755 | 2365.264 |
| Control2_021826 | 2170.275 | 2212.367 | 2186.7 | 2585.956 | 3076.474 | 2347.794 | 2926.708 | 2668.387 |
| Control2_021829 | 727.9997 | 821.4169 | 966.9506 | 1252.757 | 1200.859 | 1308.101 | 1360.473 | 991.0163 |
| Control2_021831 | 1082.576 | 1191.876 | 1338.483 | 1541.967 | 1694.252 | 1659.618 | 1599.125 | 1224.445 |
| Control2_021834 | 2115.083 | 2133.577 | 2971.31 | 2478.802 | 2751.062 | 4492.736 | 2664.171 | 2371.209 |
| Control2_021835 | 1800.552 | 4143.1 | 2827.079 | 2165.51 | 1599.139 | 3511.991 | 1954.184 | 1569.674 |
| Control2_021836 | 1245.328 | 3282.619 | 1606.868 | 2021.895 | 2213.233 | 2169.312 | 1826.482 | 1525.452 |
| Control2_021837 | 1232.15 | 1843.519 | 1565.995 | 1737.465 | 1662.996 | 3514.607 | 1634.608 | 1499.075 |
| Control2_021839 | 1520.202 | 1957.838 | 1960.711 | 2279.169 | 2273.681 | 3209.642 | 2471.854 | 2103.487 |
| Control2_021840 | 1006.846 | 1466.336 | 1352.943 | 1436.497 | 1554.106 | 2073.867 | 1482.862 | 2043.637 |
| Control2_021844 | 1527.763 | 2143.553 | 2124.143 | 2583.149 | 2526.574 | 3471.964 | 2444.126 | 2209.262 |
| Control2_021845 | 1708.471 | 2597.062 | 3056.738 | 2764.51 | 2509.027 | 3627.698 | 2486.593 | 2214.397 |
| Control2_021848 | 1511.619 | 1337.722 | 1397.268 | 1647.631 | 1456.605 | 2385.061 | 1408.622 | 1224.608 |
| Control2_021849 | 1866.328 | 2832.416 | 4456.51 | 2224.86 | 2056.029 | 3537.863 | 2201.666 | 1893.812 |
| Control2_021850 | 2220.246 | 1058.777 | 1760.467 | 2172.435 | 1948.469 | 2902.667 | 2243.549 | 1943.425 |
| Control2_021851 | 3033.04 | 2883.127 | 3632.569 | 3669.286 | 3355.756 | 4199.051 | 3220.745 | 3010.425 |
| Control2_021852 | 1652.118 | 1463.437 | 1920.526 | 2158.32 | 1879.306 | 2640.924 | 2086.825 | 1879.865 |
| Control2_021853 | 891.6693 | 1094.034 | 1197.545 | 1478.783 | 1579.288 | 1847.533 | 1463.02 | 1369.585 |
| Control2_021855 | 1430.95 | 1762.848 | 1859.345 | 2189.602 | 2208.481 | 2695.143 | 2471.515 | 1924.412 |
| Control2_021861 | 1597.079 | 1676.007 | 1582.567 | 1887.047 | 1917.212 | 2577.912 | 2051.175 | 1694.966 |
| Control2_021862 | 1113.862 | 1470.806 | 1490.145 | 1769.074 | 1888.085 | 2226.298 | 1665.863 | 1505.797 |
| Control2_021864 | 1668.539 | 1449.478 | 1434.442 | 1329.608 | 1308.309 | 1871.11 | 1584.434 | 1139.643 |
| Control2_021866 | 2106.947 | 3537.804 | 2356.46 | 3515.985 | 3030.057 | 4083.057 | 3325.615 | 2975.695 |

TABLE 6-continued

| | | | Normalised RFU values for the 19 biomarkers | | | | | |
|---|---|---|---|---|---|---|---|---|
| Control2_021869 | 3801.609 | 4345.063 | 4445.315 | 2569.386 | 2154.123 | 5376.007 | 1874.028 | 1627.357 |
| Control2_021870 | 1405.225 | 1733.58 | 1940.332 | 2278.261 | 2483.545 | 3020.657 | 2064.894 | 1919.133 |
| Control2_021872 | 1286.815 | 7318.886 | 2611.127 | 2152.928 | 2157.179 | 2850.372 | 2268.582 | 2110.246 |
| Control2_021874 | 1724.234 | 2365.071 | 2544.429 | 2717.166 | 2505.942 | 3590.685 | 2480.078 | 2400.147 |
| Control2_021875 | 1417.375 | 1366.168 | 1691.543 | 2298.582 | 2233.337 | 2976.039 | 2081.084 | 2989.963 |
| Control2_021876 | 1537.92 | 1520.497 | 1819.945 | 2074.254 | 2079.594 | 2127.166 | 1807.031 | 1649.114 |
| Control2_021877 | 2169.568 | 2520.335 | 2805.955 | 2901.827 | 2795.744 | 3439.995 | 2824.899 | 2605.987 |
| Control2_021882 | 1853.488 | 1463.824 | 2709.683 | 2630.134 | 2613.521 | 4889.535 | 2481.181 | 2151.083 |
| Control2_021884 | 1966.939 | 1262.075 | 1971.59 | 2222.155 | 2054.503 | 2464.76 | 2088.945 | 3236.594 |
| Control2_021885 | 2316.15 | 1641.508 | 2386.34 | 2210.695 | 2094.819 | 2590.088 | 2073.195 | 1878.722 |
| Control2_021887 | 1531.977 | 1308.395 | 1976.089 | 1951.533 | 1830.006 | 2269.807 | 1804.872 | 1627.947 |
| Control2_021888 | 1816.136 | 1727.809 | 2177.399 | 2355.914 | 2248.237 | 3075.7 | 2270.959 | 2016.192 |
| Control2_021889 | 1191.999 | 1224.372 | 1456.478 | 1671.608 | 1769.808 | 1729.559 | 1738.464 | 1479.342 |
| Control2_021893 | 961.8649 | 863.8429 | 1231.316 | 1339.618 | 1244.098 | 1399.984 | 1578.939 | 1009.998 |
| Control2_021896 | 1175.956 | 1869.874 | 1542.43 | 1767.732 | 1848.923 | 2319.642 | 1848.402 | 1313.737 |
| Control2_021898 | 1421.408 | 1274.498 | 1793.884 | 2191.324 | 2017.862 | 2316.975 | 2054.023 | 1780.855 |
| Control2_021899 | 1169.115 | 1018.919 | 1380.195 | 1747.41 | 1623.652 | 2066.902 | 1759.251 | 1608.307 |
| Control2_021900 | 1805.134 | 2272.669 | 2339.801 | 2877.322 | 2870.634 | 3650.904 | 3154.306 | 2943.415 |
| Control2_021962 | 1299.376 | 1469.512 | 1752.46 | 2072.822 | 2154.644 | 3048.746 | 1847.226 | 1801.589 |
| EarlyStg1_021633 | 888.7379 | 1083.956 | 1139.705 | 1745.988 | 1624.386 | 2126.853 | 1864.5 | 2451.019 |
| EarlyStg1_021651 | 1718.134 | 1869.381 | 2002.153 | 2829.701 | 2301.549 | 3393.112 | 2494.653 | 2191.697 |
| EarlyStg1_021654 | 1414.691 | 2009.296 | 1875.053 | 3674.002 | 3193.332 | 2959.501 | 3266.428 | 2816.123 |
| EarlyStg1_021655 | 2360.272 | 2071.366 | 2048.578 | 4079.875 | 3856.399 | 3233.548 | 3060.038 | 2967.291 |
| EarlyStg1_021662 | 1046.279 | 1038.759 | 1247.205 | 1608.22 | 1934.638 | 1675.178 | 1641.528 | 1478.774 |
| EarlyStg1_021675 | 2008.526 | 2211.421 | 2262.93 | 3836.686 | 3311.173 | 4348.88 | 3947.239 | 3216.422 |
| EarlyStg1_021678 | 809.411 | 1196.975 | 1171.397 | 1416.018 | 1513.61 | 1406.448 | 3201.611 | 3765.569 |
| EarlyStg2_021024 | 1666.611 | 2348.44 | 1861.542 | 1900.112 | 2175.75 | 2635.829 | 2138.762 | 1641.05 |
| EarlyStg2_021403 | 864.2702 | 908.2656 | 966.5297 | 1152.405 | 1152.189 | 1208.682 | 1132.829 | 999.4889 |
| EarlyStg2_021435 | 818.7927 | 946.9137 | 862.6614 | 1138.72 | 1062.796 | 1348.046 | 1297.819 | 1024.028 |
| EarlyStg2_021440 | 1115.634 | 1262.505 | 1256.625 | 1676.983 | 1456.852 | 1876.273 | 1804.083 | 1597.008 |
| EarlyStg2_021443 | 2209.834 | 2323.86 | 2268.553 | 4227.051 | 2746.796 | 3529.186 | 2838.406 | 2627.111 |
| EarlyStg2_021458 | 2764.343 | 2321.842 | 3096.833 | 2692.237 | 2468.356 | 3620.752 | 2475.345 | 2253.773 |
| EarlyStg2_021462 | 1168.597 | 1095.781 | 1259.984 | 1473.306 | 1355.856 | 1573.764 | 1735.746 | 1327.889 |
| EarlyStg2_021466 | 2917.855 | 2471.582 | 2442.846 | 3334.242 | 3444.158 | 3068.349 | 2739.576 | 2864.376 |
| EarlyStg2_021489 | 3814.376 | 64378.83 | 54002.38 | 1724.073 | 1619.1 | 2201.599 | 1688.194 | 1538.798 |
| EarlyStg2_021496 | 2140.219 | 2044.7 | 2620.907 | 2860.923 | 2714.917 | 3523.228 | 2716.084 | 4006.147 |
| EarlyStg2_021814 | 1434.233 | 1436.983 | 1273.89 | 1802.932 | 1544.033 | 1577.473 | 1621.802 | 1248.348 |
| EarlyStg2_021815 | 6157.471 | 3813.734 | 3852.406 | 8214.276 | 10197.87 | 7104.856 | 5543.301 | 6291.762 |
| EarlyStg2_021820 | 1272.23 | 1459.923 | 1404.584 | 2228.886 | 1796.769 | 2841.497 | 3885.665 | 4033.956 |
| EarlyStg2_021827 | 616.5434 | 786.2398 | 791.7878 | 977.2698 | 979.6347 | 1131.393 | 1511.574 | 838.4045 |
| EarlyStg2_021830 | 1350.571 | 1322.662 | 1347.479 | 1637.868 | 1574.216 | 1864.733 | 1802.094 | 1318.946 |
| EarlyStg2_021832 | 685.3966 | 768.7034 | 771.6687 | 907.4298 | 959.8832 | 881.5877 | 1484.217 | 1441.072 |
| EarlyStg2_021842 | 559.1504 | 728.8939 | 773.4969 | 886.8648 | 874.0025 | 1128.443 | 1246.985 | 812.1934 |
| EarlyStg2_021843 | 998.7775 | 1042.343 | 1037.048 | 1316.874 | 1545.713 | 1488.783 | 1464.504 | 1162.424 |
| EarlyStg2_021847 | 847.6904 | 834.0404 | 1065.834 | 1241.691 | 984.5962 | 1537.282 | 1765.055 | 1053.372 |
| EarlyStg2_021858 | 2884.206 | 3845.013 | 4219.314 | 3940.725 | 3779.591 | 4932.521 | 3850.321 | 3779.076 |
| EarlyStg2_021867 | 1027.782 | 3742.673 | 1421.976 | 1480.335 | 1415.318 | 1834.294 | 1702.586 | 1363.897 |
| EarlyStg2_021873 | 1991.314 | 64387.9 | 68263.43 | 2576.418 | 2450.923 | 3204.567 | 61022.98 | 61141.06 |
| EarlyStg2_021895 | 1309.615 | 1142.613 | 1833.176 | 1552.477 | 1668.209 | 2018.585 | 1748.757 | 1350.093 |
| EarlyStg2_021960 | 2893.513 | 3014.18 | 3981.726 | 31577.67 | 4138.143 | 6326.917 | 4832.018 | 7208.038 |
| LateStg1_021607 | 2233.818 | 33710.4 | 27509.89 | 2683.862 | 2431.354 | 5415.112 | 2263.816 | 2008.929 |
| LateStg1_021631 | 1077.574 | 1286.721 | 1463.395 | 1459.115 | 1434.265 | 1880.945 | 1247.632 | 1032.569 |
| LateStg1_021632 | 3286.639 | 1480.678 | 1291.98 | 1680.948 | 1599.405 | 1828.069 | 1593.324 | 1280.285 |
| LateStg1_021683 | 1332.092 | 920.1105 | 1136.96 | 1548.33 | 1181.713 | 1415.653 | 1581.494 | 1335.489 |
| LateStg1_021691 | 3844.224 | 3683.971 | 6199.383 | 3335.339 | 3994.33 | 8536.385 | 2753.94 | 2503.818 |
| LateStg1_021692 | 1632.176 | 7969.794 | 4384.263 | 2698.668 | 2282.849 | 2693.694 | 2417.603 | 2147.67 |
| LateStg1_021696 | 6599.412 | 5823.924 | 6186.081 | 5783.523 | 4699.548 | 7686.687 | 5192.874 | 4561.238 |
| LateStg1_021699 | 908.5383 | 943.1396 | 1345.248 | 1535.726 | 1361.538 | 2004.212 | 1679.826 | 1162.804 |
| LateStg2_021004 | 3221.85 | 4463.517 | 3620.611 | 3510.513 | 3849.087 | 5065.177 | 3227.483 | 3134.377 |
| LateStg2_021006 | 2339.927 | 2435.977 | 2422.967 | 3627.886 | 4482.165 | 3510.889 | 2848.815 | 2488.987 |
| LateStg2_021028 | 2707.792 | 4469.606 | 3026.737 | 4088.437 | 4885.905 | 4633.554 | 4514.939 | 5517.361 |
| LateStg2_021029 | 4950.915 | 4573.694 | 5365.522 | 5212.313 | 5258.751 | 7136.894 | 4720.304 | 4089.176 |
| LateStg2_021039 | 3522.816 | 3382.284 | 4025.145 | 4416.734 | 5475.508 | 4942.533 | 4098.692 | 4279.457 |
| LateStg2_021040 | 2002.684 | 1739.248 | 2184.697 | 2733.813 | 2964.582 | 2841.992 | 2364.913 | 2064.116 |
| LateStg2_021402 | 1361.542 | 1273.69 | 1436.17 | 30543.01 | 1661.542 | 2105.953 | 1792.681 | 1556.671 |
| LateStg2_021404 | 1825.759 | 1561.872 | 1859.06 | 2102.176 | 1937.207 | 2621.452 | 1884.312 | 1886.038 |
| LateStg2_021409 | 1821.798 | 1622.475 | 1888.661 | 2005.027 | 2042.316 | 2466.845 | 2172.961 | 1965.279 |
| LateStg2_021411 | 12831.44 | 2658.677 | 2981.266 | 3455.966 | 66480.3 | 3872.695 | 2669.909 | 2881 |
| LateStg2_021412 | 1375.199 | 1239.54 | 1325.421 | 1639.334 | 3807.727 | 1852.533 | 1571.277 | 1348.274 |
| LateStg2_021413 | 1771.981 | 1487.26 | 2007.343 | 1924.228 | 2049.404 | 2192.016 | 1768.964 | 1748.733 |
| LateStg2_021418 | 1312.756 | 1172.529 | 1327.484 | 1582.212 | 1511.383 | 2946.084 | 1518.947 | 1320.067 |
| LateStg2_021421 | 3372.893 | 1793.388 | 1865.367 | 1997.554 | 2003.966 | 2556.354 | 2058.865 | 1860.537 |
| LateStg2_021422 | 2876.725 | 2164.961 | 2960.132 | 2820.349 | 4247.47 | 3985.439 | 2012.289 | 1996.894 |
| LateStg2_021424 | 1510.005 | 1436.097 | 1764.94 | 2312.824 | 2095.89 | 2981.925 | 2034.561 | 2011.813 |
| LateStg2_021425 | 4155.837 | 3164.881 | 3549.289 | 4399.627 | 3495.884 | 69262.64 | 3726.524 | 3610.125 |
| LateStg2_021427 | 6471.712 | 5562.278 | 5414.813 | 2359.317 | 1931.492 | 5062.902 | 2487.975 | 2015.596 |
| LateStg2_021428 | 1315.405 | 1923.432 | 1325.323 | 1540.169 | 1567.625 | 1995.128 | 1862.058 | 1623.103 |
| LateStg2_021429 | 2123.084 | 2559.612 | 2236.494 | 3001.687 | 2607.627 | 3412.53 | 2292.985 | 2415.871 |

TABLE 6-continued

Normalised RFU values for the 19 biomarkers

| | | | | | | | | |
|---|---|---|---|---|---|---|---|---|
| LateStg2_021431 | 1761.144 | 1820.044 | 2118.511 | 2601.028 | 2288.129 | 3056.034 | 2245.269 | 3071.717 |
| LateStg2_021432 | 2360.041 | 2259.147 | 2011.696 | 2624.354 | 2347.857 | 3114.266 | 2267.014 | 2232.296 |
| LateStg2_021433 | 2535.536 | 2996.462 | 2903.991 | 3686.228 | 3635.17 | 44392.76 | 3044.162 | 3183.385 |
| LateStg2_021437 | 2480.932 | 2964.578 | 2577.313 | 3395.92 | 3330.783 | 3915.391 | 2871.597 | 3034.91 |
| LateStg2_021441 | 2178.753 | 3019.759 | 2484.399 | 3276.622 | 3424.187 | 4497.703 | 4627.948 | 5516.538 |
| LateStg2_021442 | 1402.243 | 1687.07 | 1595.617 | 2190.64 | 2035.534 | 2949.132 | 1854.978 | 1630.612 |
| LateStg2_021450 | 72225 | 4925.92 | 5586.278 | 7038.924 | 6264.657 | 9305.774 | 5407.448 | 6106.828 |
| LateStg2_021452 | 2351.882 | 2117.25 | 2515.784 | 2714.059 | 2709.585 | 3236.665 | 2472.468 | 2335.358 |
| LateStg2_021456 | 2281.465 | 1624.104 | 2069.136 | 2084.323 | 1906.072 | 2652.478 | 2118.836 | 1945.565 |
| LateStg2_021457 | 7111.74 | 5438.97 | 6081.31 | 7192.698 | 6515.937 | 8094.362 | 5778.938 | 6053.032 |
| LateStg2_021459 | 1662.911 | 1488.942 | 1709.95 | 5439.639 | 1756.361 | 2467.384 | 2151.735 | 1685.922 |
| LateStg2_021467 | 2871.091 | 2477.123 | 2697.42 | 3051.383 | 2669.106 | 4019.018 | 2084.887 | 2514.498 |
| LateStg2_021468 | 2239.595 | 2067.363 | 2455.974 | 2399.43 | 2260.627 | 3172.673 | 2334.31 | 2192.644 |
| LateStg2_021469 | 1134.769 | 1041.707 | 1124.96 | 1394.012 | 1423.355 | 1609.735 | 1685.225 | 1274.357 |
| LateStg2_021471 | 1883.788 | 1395.216 | 2140.146 | 2416.612 | 2918.033 | 2983.943 | 2138.6 | 2029.309 |
| LateStg2_021476 | 3258.855 | 2759.33 | 2993.915 | 3391.916 | 2972.729 | 4209.934 | 2853.457 | 3199.763 |
| LateStg2_021479 | 2880.929 | 2591.085 | 2935.565 | 3095.02 | 2751.518 | 3877.997 | 2929.471 | 2761.362 |
| LateStg2_021485 | 3236.978 | 2840.985 | 3298.95 | 3514.251 | 3336.928 | 4831.199 | 4070.197 | 5153.553 |
| LateStg2_021490 | 2055.398 | 2328.332 | 2304.917 | 2529.798 | 2578.518 | 2827.262 | 2270.409 | 2361.421 |
| LateStg2_021493 | 2089.283 | 1969.834 | 2252.854 | 2541.756 | 2554.018 | 3403.82 | 2142.646 | 2208.38 |
| LateStg2_021498 | 3994.694 | 3345.87 | 3519.226 | 4221.659 | 4350.851 | 4858.934 | 3506.732 | 3779.842 |
| LateStg2_021499 | 2712.5 | 2477.536 | 2535.785 | 3120.787 | 3083.258 | 4619.17 | 3050.456 | 3503.044 |
| LateStg2_021803 | 2568.571 | 2524.476 | 2509.832 | 2820.704 | 2609.458 | 2990.457 | 2279.461 | 2172.796 |
| LateStg2_021817 | 2184.182 | 2720.577 | 2811.529 | 4809.278 | 63866.5 | 4006.276 | 3240.366 | 2969.606 |
| LateStg2_021819 | 2690.661 | 2528.864 | 2868.553 | 3699.345 | 4265.994 | 3856.545 | 3302.492 | 2991.057 |
| LateStg2_021821 | 3862.728 | 5570.37 | 2950.673 | 3903.449 | 4548.635 | 5141.088 | 3771.425 | 3412.051 |
| LateStg2_021828 | 3612.2 | 32668.33 | 13719.52 | 3451.276 | 3465.224 | 5624.391 | 2798.934 | 3131.383 |
| LateStg2_021833 | 988.1922 | 1768.821 | 1152.149 | 1436.283 | 1414.762 | 1567.374 | 1619.189 | 1172.344 |
| LateStg2_021838 | 1659.286 | 2605.402 | 1884.594 | 2379.837 | 2659.232 | 2909.178 | 2613.869 | 2226.825 |
| LateStg2_021841 | 7280.658 | 8393.207 | 6239.35 | 5096.393 | 4927.956 | 7779.298 | 5001.383 | 4618.61 |
| LateStg2_021846 | 1017.125 | 1024.531 | 1290.688 | 1716.599 | 2259.379 | 2301.196 | 1865.429 | 1345.855 |
| LateStg2_021854 | 1631.081 | 2256.517 | 1994.206 | 2089.055 | 2115.195 | 2810.059 | 2315.125 | 1818.905 |
| LateStg2_021856 | 1757.762 | 1863.022 | 1772.417 | 2268.092 | 2477.31 | 2647.954 | 2176.189 | 1961.227 |
| LateStg2_021857 | 3901.552 | 3670.615 | 3626.944 | 4188.205 | 4158.46 | 4751.309 | 3987.096 | 3730.004 |
| LateStg2_021859 | 1470.294 | 1885.057 | 1935.032 | 2271.902 | 2294.143 | 3048.345 | 2117.187 | 1776.545 |
| LateStg2_021860 | 1377.228 | 1912.527 | 1545.966 | 2029.096 | 3843.036 | 2294.62 | 2148.919 | 1831.696 |
| LateStg2_021863 | 1389.546 | 1225.311 | 1220.319 | 1592.922 | 1506.453 | 1743.039 | 37436.57 | 20785.09 |
| LateStg2_021865 | 847.9526 | 72243.9 | 58963.65 | 1584.339 | 1561.829 | 1890.786 | 1446.563 | 1301.552 |
| LateStg2_021868 | 841.1623 | 1730.123 | 1106.992 | 1520.119 | 1326.74 | 1839.049 | 1526.568 | 1216.93 |
| LateStg2_021871 | 4293.53 | 11133.89 | 6076.056 | 6914.307 | 6755.11 | 13075.63 | 5942.146 | 5916.069 |
| LateStg2_021880 | 1790.208 | 1980.132 | 2614.285 | 2057.024 | 2096.017 | 3959.8 | 1832.259 | 1487.634 |
| LateStg2_021881 | 2384.826 | 1999.357 | 2666.056 | 2852.15 | 3033.592 | 3377.481 | 4271.626 | 3901.21 |
| LateStg2_021883 | 2065.41 | 1622.946 | 2569.527 | 2671.253 | 4642.282 | 3220.608 | 2297.504 | 2061.914 |
| LateStg2_021890 | 3022.65 | 1988.88 | 2282.66 | 2251.566 | 2248.979 | 3052.289 | 2415.519 | 2128.133 |
| LateStg2_021891 | 1124.762 | 961.2568 | 1354.482 | 1361.077 | 1241.26 | 1576.201 | 1462.741 | 1096.385 |
| LateStg2_021892 | 2474.483 | 4105.839 | 4501.21 | 2967.051 | 2868.365 | 4078.879 | 2353.423 | 2167.423 |
| LateStg2_021894 | 2221.702 | 1767.34 | 2488.434 | 1923.35 | 2652.345 | 5760.332 | 4985.451 | 1684.064 |
| LateStg2_021897 | 2094.173 | 1872.113 | 2564.54 | 3134.878 | 3177.1 | 3170.251 | 2812.481 | 2291.9 |
| LateStg2_021959 | 1944.575 | 1075.842 | 1370.23 | 6504.857 | 55850.97 | 2370.069 | 1624.237 | 1465.625 |
| LateStg2_021961 | 2126.008 | 2601.519 | 2931.139 | 3868.475 | 3742.739 | 5313.381 | 3308.218 | 3188.797 |
| LateStg2_021499 | 2712.5 | 2477.536 | 2535.785 | 3120.787 | 3083.258 | 4619.17 | 3050.456 | 3503.044 |

| Protein | IGF2BP3 | LRRFIP2 | MAGEA10 | MAGEA4 | MAP2K5 | PTPN20A |
|---|---|---|---|---|---|---|
| Control1_021608 | 1864.379 | 10256.51 | 1707.204 | 1270.237 | 2062.856 | 3315.828 |
| Control1_021611 | 984.5742 | 1642.046 | 949.5056 | 717.2795 | 980.4752 | 1986.406 |
| Control1_021630 | 2495.178 | 3443.966 | 2016.665 | 1715.477 | 2661.723 | 5203.608 |
| Control1_021631 | 1769.07 | 2760.66 | 2086.983 | 2381.255 | 2711.591 | 2212.801 |
| Control1_021642 | 2347.117 | 5726.215 | 2239.27 | 1819.513 | 2590.68 | 5952.694 |
| Control1_021643 | 1577.693 | 2475.029 | 1392.899 | 1095.408 | 1734.76 | 1687.801 |
| Control1_021650 | 1712.624 | 3158.91 | 2166.367 | 3076.026 | 3988.011 | 4640.239 |
| Control1_021660 | 2025.719 | 10491.47 | 1699.251 | 1931.718 | 2483.095 | 2033.607 |
| Control1_021661 | 2947.112 | 4964.015 | 2260.505 | 1715.278 | 2982.163 | 2494.186 |
| Control1_021663 | 2921.823 | 3766.776 | 2208.297 | 1894.731 | 2643.505 | 2964.772 |
| Control1_021674 | 1885.233 | 5666.105 | 1571.638 | 1156.283 | 2244.439 | 2457.223 |
| Control1_021679 | 1483.428 | 2188.354 | 1499.469 | 1066.008 | 2001.052 | 1444.111 |
| Control1_021680 | 2291.881 | 7936.889 | 2166.929 | 1679.373 | 2362.385 | 3149.52 |
| Control1_021681 | 3826.813 | 10582.86 | 6322.936 | 4911.227 | 5544.572 | 13939.81 |
| Control1_021682 | 2371.601 | 4526.223 | 1991.898 | 1569.11 | 4169.351 | 2907.473 |
| Control2_021005 | 6199.772 | 11076.7 | 11112.01 | 9611.882 | 6652.302 | 19237.07 |
| Control2_021007 | 3216.338 | 5692.778 | 3194.603 | 2842.006 | 4446.303 | 3910.378 |
| Control2_021016 | 1894.693 | 3015.911 | 2324.273 | 1948.089 | 2766.241 | 2710.309 |
| Control2_021017 | 1714.025 | 3137.241 | 1811.556 | 1476.747 | 2095.534 | 2572.001 |
| Control2_021025 | 2301.794 | 5997.156 | 1928.071 | 1764.336 | 2214.804 | 2567.013 |
| Control2_021037 | 1786.695 | 11870.33 | 1835.236 | 1526.275 | 2408.522 | 3380.793 |
| Control2_021038 | 1468.671 | 2967.612 | 1523.531 | 1207.042 | 2009.926 | 1666.915 |
| Control2_021045 | 1833.289 | 2309.808 | 2015.164 | 1736.922 | 2395.172 | 2511.068 |
| Control2_021046 | 3026.465 | 6848.673 | 2894.598 | 2433.767 | 3258.239 | 5672.938 |

TABLE 6-continued

| | | Normalised RFU values for the 19 biomarkers | | | |
|---|---|---|---|---|---|
| Control2_021401 | 2153.839 | 3751.081 | 2099.173 | 2967.183 | 2414.103 | 2164.446 |
| Control2_021405 | 1577.527 | 2708.492 | 1709.801 | 1549.398 | 2091.493 | 2295.796 |
| Control2_021406 | 1377.186 | 3379.66 | 1510.359 | 1138.178 | 1824.205 | 1522.514 |
| Control2_021419 | 1327.409 | 2950.186 | 1288.873 | 1206.732 | 1920.516 | 3093.032 |
| Control2_021420 | 1427.761 | 3191.296 | 1505.299 | 1258.148 | 1800.616 | 1843.103 |
| Control2_021423 | 3570.623 | 6620.853 | 3579.061 | 2918.362 | 4426.904 | 4727.215 |
| Control2_021426 | 2939.504 | 8472.987 | 2853.974 | 2939.304 | 5489.914 | 2777.067 |
| Control2_021430 | 1712.129 | 3839.469 | 1920.69 | 1343.425 | 2271.696 | 2344.028 |
| Control2_021436 | 1492.531 | 2310.743 | 1607.355 | 1279.09 | 1830.218 | 1714.501 |
| Control2_021451 | 2780.555 | 3572.501 | 2861.352 | 2283.854 | 3366.02 | 3448.814 |
| Control2_021453 | 1955.682 | 6044.063 | 2175.041 | 1564.877 | 2295.219 | 2062.084 |
| Control2_021454 | 1577.288 | 2848.697 | 1455.822 | 1306.672 | 1894.117 | 1759.484 |
| Control2_021455 | 2564.917 | 4994.603 | 2530.726 | 1924.332 | 3277.945 | 2818.599 |
| Control2_021463 | 4073.638 | 10964.05 | 4476.259 | 3557.854 | 4176.659 | 5050.335 |
| Control2_021470 | 1751.386 | 5710.754 | 1632.83 | 1402.099 | 2130.032 | 2535.66 |
| Control2_021477 | 3498.464 | 6047.108 | 2975.548 | 2798.397 | 3279.928 | 6853.659 |
| Control2_021478 | 1975.51 | 4209.962 | 3187.603 | 1924.962 | 2382.097 | 3422.74 |
| Control2_021484 | 2030.785 | 4996.788 | 2260.441 | 1635.343 | 2426.476 | 2468.278 |
| Control2_021494 | 1358.159 | 6289.746 | 1428.486 | 1155.8 | 1760.796 | 3294.846 |
| Control2_021495 | 7607.972 | 10760.02 | 8813.236 | 8154.649 | 4858.083 | 8017.285 |
| Control2_021497 | 2022.71 | 2381.643 | 2071.199 | 1836.147 | 2880.86 | 2694.962 |
| Control2_021801 | 2131.438 | 2938.354 | 1934.592 | 1637.284 | 2040.849 | 2076.451 |
| Control2_021802 | 1582.688 | 1721.553 | 1333.201 | 1159.959 | 2289.404 | 5436.568 |
| Control2_021804 | 2513.429 | 4985.019 | 1938.967 | 1565.209 | 2898.718 | 2946.264 |
| Control2_021805 | 1813.176 | 4710.699 | 1744.263 | 1476.581 | 3112.112 | 2164.224 |
| Control2_021806 | 2214.155 | 3592.359 | 3411.004 | 2731.398 | 4373.876 | 4083.713 |
| Control2_021809 | 1756.475 | 3069.143 | 1770.113 | 1568.689 | 2315.789 | 1870.303 |
| Control2_021810 | 2409.725 | 4595.2 | 2483.45 | 2014.932 | 3161.544 | 2782.631 |
| Control2_021811 | 1230.763 | 1702.497 | 1990.884 | 1592.71 | 2056.904 | 2890.082 |
| Control2_021812 | 3736.236 | 6074.945 | 5099.298 | 3351.37 | 5101.794 | 4984.095 |
| Control2_021818 | 1723.422 | 3067.722 | 1692.577 | 2609.891 | 2401.301 | 1806.957 |
| Control2_021822 | 2258.871 | 5106.237 | 2454.382 | 1692.475 | 2726.053 | 2685.046 |
| Control2_021823 | 1782.433 | 5978.676 | 1373.312 | 1059.723 | 2141.575 | 2758.369 |
| Control2_021824 | 1929.38 | 3387.352 | 5770.001 | 3186.82 | 2379.998 | 6112.298 |
| Control2_021825 | 2894.506 | 12133.5 | 3019.027 | 2065.98 | 3470.955 | 3126.288 |
| Control2_021826 | 2975.528 | 3619.189 | 2449.931 | 1765.577 | 2665.075 | 4058.315 |
| Control2_021829 | 1078.297 | 2541.436 | 1017.431 | 829.9832 | 1492.023 | 1211.206 |
| Control2_021831 | 1388.789 | 17426.87 | 1383.007 | 1163.831 | 1803.056 | 2659.547 |
| Control2_021834 | 2731.65 | 3946.079 | 2371.834 | 2448.149 | 3712.545 | 3132.718 |
| Control2_021835 | 1425.636 | 4211.808 | 2462.035 | 1860.317 | 2387.911 | 3136.524 |
| Control2_021836 | 2048.427 | 3871.687 | 1729.768 | 1484.16 | 2294.109 | 1869.645 |
| Control2_021837 | 1745.759 | 2669.79 | 1544.561 | 1699.246 | 2605.019 | 2069.25 |
| Control2_021839 | 2341.041 | 3813.47 | 2127.806 | 1811.276 | 2915.472 | 2172.454 |
| Control2_021840 | 1466.736 | 2785.596 | 1425.364 | 1161.345 | 1872.754 | 1764.8 |
| Control2_021844 | 2580.429 | 5380.09 | 2196.979 | 1899.78 | 3372.265 | 2346.553 |
| Control2_021845 | 2724.959 | 4277.382 | 2346.401 | 1932.341 | 3312.14 | 2775.452 |
| Control2_021848 | 1456.744 | 2689.313 | 1499.23 | 1191.049 | 2159.648 | 6106.434 |
| Control2_021849 | 1987.449 | 3206.646 | 2118.117 | 2061.679 | 4011.126 | 3273.238 |
| Control2_021850 | 2179.94 | 2594.357 | 2051.556 | 1817.563 | 2913.705 | 2595.519 |
| Control2_021851 | 3358.091 | 5593.778 | 3204.729 | 3319.564 | 7174.081 | 5437.286 |
| Control2_021852 | 1963.275 | 2311.181 | 1711.839 | 1746.169 | 2653.722 | 2219.421 |
| Control2_021853 | 1542.191 | 2405.584 | 1254.529 | 2225.92 | 1840.036 | 1395.407 |
| Control2_021855 | 2092.828 | 5193.978 | 1821.72 | 1955.116 | 3112.859 | 2274.963 |
| Control2_021861 | 1766.345 | 2249.844 | 1485.959 | 1441.116 | 2357.153 | 1741.011 |
| Control2_021862 | 1758.152 | 3119.105 | 1388.473 | 1208.254 | 2264.852 | 1470.605 |
| Control2_021864 | 1228.498 | 1617.374 | 1600.64 | 1097.203 | 1773.925 | 1405.638 |
| Control2_021866 | 3340.706 | 3692.312 | 3083.481 | 2305.219 | 4003.694 | 3172.705 |
| Control2_021869 | 2041.283 | 5513.359 | 4128.772 | 3249.421 | 2908.544 | 5007.78 |
| Control2_021870 | 2274.004 | 5381.599 | 3390.585 | 1763.338 | 3202.194 | 2078.389 |
| Control2_021872 | 2353.007 | 7394.805 | 1774.071 | 1518.602 | 2707.483 | 2249.85 |
| Control2_021874 | 2754.599 | 5223.595 | 2337.521 | 1887.844 | 3652.429 | 2367.014 |
| Control2_021875 | 2835.615 | 6109.194 | 1990.811 | 1606.504 | 2701.638 | 2239.367 |
| Control2_021876 | 2026.153 | 5614.535 | 1726.306 | 1692.19 | 2859.931 | 2391.009 |
| Control2_021877 | 2683.601 | 4044.607 | 2816.4 | 2392.499 | 3991.897 | 3151.645 |
| Control2_021882 | 2432.832 | 5635.096 | 2318.964 | 3012.98 | 3779.524 | 3017.525 |
| Control2_021884 | 2162.308 | 4175.698 | 1896.357 | 1930.513 | 2802.656 | 2045.35 |
| Control2_021885 | 2322.551 | 2360.523 | 2020.608 | 2019.363 | 2912.89 | 3519.932 |
| Control2_021887 | 1907.668 | 8062.939 | 1698.869 | 1543.445 | 2905.972 | 2107.129 |
| Control2_021888 | 2362.468 | 6705.703 | 2263.509 | 2009.607 | 3116.232 | 2917.681 |
| Control2_021889 | 1724.205 | 3193.269 | 1365.617 | 1264.229 | 2102.197 | 4013.068 |
| Control2_021893 | 1266.354 | 1532.566 | 1124.324 | 1133.104 | 1673.636 | 1486.05 |
| Control2_021896 | 1786.878 | 3973.447 | 1376.932 | 1401.714 | 2109.678 | 1795.883 |
| Control2_021898 | 2163.932 | 4514.717 | 2123.111 | 1578.816 | 2815.736 | 2178.103 |
| Control2_021899 | 1791.442 | 2999.335 | 1525.146 | 1254.638 | 2230.895 | 2104.384 |
| Control2_021900 | 3060.013 | 3837.566 | 3456.82 | 2574.759 | 3255.242 | 3745.962 |
| Control2_021962 | 2115.775 | 5116.496 | 1706.608 | 1628.084 | 2814.555 | 2084.987 |
| EarlyStg1_021633 | 1599.96 | 3890.38 | 1465.2 | 1037.369 | 1668.078 | 1451.583 |
| EarlyStg1_021651 | 2351.123 | 6750.972 | 2161.845 | 1771.912 | 2854.07 | 2561.211 |

TABLE 6-continued

| | | Normalised RFU values for the 19 biomarkers | | | |
|---|---|---|---|---|---|
| EarlyStg1_021654 | 2713.403 | 3945.555 | 2002.649 | 1859.56 | 2533.283 | 3189.184 |
| EarlyStg1_021655 | 3210.863 | 6902.838 | 2143.019 | 1764.912 | 3295.438 | 3250.834 |
| EarlyStg1_021662 | 1536.208 | 2295.528 | 1315.652 | 1296.914 | 2313.41 | 1630.089 |
| EarlyStg1_021675 | 3272.398 | 5877.409 | 2722.891 | 1721.796 | 3145.656 | 3171.789 |
| EarlyStg1_021678 | 1243.303 | 5240.118 | 1195.363 | 849.612 | 4169.675 | 1276.357 |
| EarlyStg2_021024 | 1784.729 | 2599.311 | 1926.939 | 1678.941 | 2398.034 | 2452.743 |
| EarlyStg2_021403 | 1193.16 | 2495.09 | 1988.684 | 8670.834 | 1149.056 | 1061.351 |
| EarlyStg2_021435 | 1020.547 | 1300.412 | 1315.539 | 812.8782 | 1992.811 | 12849.7 |
| EarlyStg2_021440 | 1495.375 | 6394.945 | 1536.416 | 1220.193 | 1741.883 | 1759.137 |
| EarlyStg2_021443 | 2716.052 | 3346.902 | 2821.284 | 2199.833 | 4253.328 | 3857.54 |
| EarlyStg2_021458 | 2492.874 | 5134.364 | 2902.898 | 2525.073 | 3200.766 | 7027.378 |
| EarlyStg2_021462 | 1447.512 | 1962.651 | 1353.171 | 1190.796 | 1692.075 | 2083.382 |
| EarlyStg2_021466 | 3539.669 | 3898.782 | 3162.375 | 2048.981 | 7417.409 | 5946.867 |
| EarlyStg2_021489 | 1833.571 | 2224.745 | 1882.389 | 1361.955 | 1828.498 | 2600.137 |
| EarlyStg2_021496 | 2532.979 | 8436.43 | 2620.774 | 2268.858 | 4002.257 | 3331.943 |
| EarlyStg2_021814 | 1184.509 | 2266.998 | 1189.78 | 1175.504 | 1929.441 | 1631.434 |
| EarlyStg2_021815 | 14434.92 | 7528.605 | 5889.771 | 5140.262 | 11153.38 | 23529.81 |
| EarlyStg2_021820 | 1791.473 | 2298.301 | 1780.983 | 1591.671 | 2375.364 | 2462.813 |
| EarlyStg2_021827 | 862.3957 | 1000.234 | 745.288 | 700.6462 | 1164.85 | 862.7676 |
| EarlyStg2_021830 | 1509.441 | 2078.313 | 1378.075 | 1235.311 | 1996.329 | 1743.144 |
| EarlyStg2_021832 | 940.8926 | 955.0221 | 749.3359 | 680.3148 | 1144.174 | 877.5483 |
| EarlyStg2_021842 | 787.061 | 1720.34 | 740.0612 | 1044.132 | 1072.525 | 843.0966 |
| EarlyStg2_021843 | 1227.167 | 1199.951 | 1252.088 | 932.2355 | 1420.142 | 1299.8 |
| EarlyStg2_021847 | 988.6661 | 1455.479 | 1061.089 | 976.3165 | 2364.797 | 1223.133 |
| EarlyStg2_021858 | 3654.264 | 5782.754 | 6309.748 | 4035.687 | 5097.5 | 4892.059 |
| EarlyStg2_021867 | 1471.776 | 2148.901 | 1221.715 | 1187.602 | 1867.458 | 2958.356 |
| EarlyStg2_021873 | 2437.692 | 3159.13 | 6431.019 | 2019.762 | 3573.626 | 2866.673 |
| EarlyStg2_021895 | 1657.107 | 3322.74 | 1374.092 | 1347.937 | 2303.925 | 2011.179 |
| EarlyStg2_021960 | 4473.527 | 6067.125 | 2660.867 | 3715.26 | 5565.572 | 4084.967 |
| LateStg1_021607 | 2639.71 | 4167.536 | 21571.06 | 20747.58 | 2873.485 | 7195.459 |
| LateStg1_021612 | 1283.638 | 1777.645 | 1451.691 | 1189.345 | 1739.08 | 1653.534 |
| LateStg1_021632 | 1799.823 | 3101.039 | 2060.273 | 1602.773 | 5195.655 | 1645.745 |
| LateStg1_021683 | 1143.095 | 2445.638 | 1851.534 | 4298.669 | 8690.543 | 1780.728 |
| LateStg1_021691 | 2924.456 | 8177.706 | 4079.96 | 2844.118 | 2816.506 | 6253.56 |
| LateStg1_021692 | 8336.307 | 2067.293 | 2052.88 | 3534.455 | 2314.055 | 2435.415 |
| LateStg1_021696 | 5254.942 | 7300.942 | 5486.125 | 3686.07 | 10444.32 | 10842.8 |
| LateStg1_021699 | 1463.845 | 1553.582 | 1393.758 | 1065.26 | 1777.222 | 1628.989 |
| LateStg2_021004 | 3447.883 | 6800.578 | 3186.653 | 2627.675 | 3490.451 | 4227.487 |
| LateStg2_021006 | 3785.679 | 12021 | 3061.898 | 3122.281 | 3726.921 | 3191.783 |
| LateStg2_021028 | 4012.385 | 4351.325 | 3588.626 | 3046.919 | 4898.403 | 3893.103 |
| LateStg2_021029 | 4817.28 | 7556.265 | 4689.437 | 4079.114 | 5566.21 | 8339.843 |
| LateStg2_021039 | 4220.891 | 10757.38 | 3931.166 | 3348.218 | 5050.079 | 7727.377 |
| LateStg2_021040 | 2472.303 | 12349.52 | 2486.638 | 2116.17 | 3101.401 | 3078.854 |
| LateStg2_021402 | 1665.538 | 10941.54 | 2164.561 | 3789.045 | 2091.446 | 23209.96 |
| LateStg2_021404 | 2103.374 | 10730.8 | 2301.383 | 1848.497 | 2619.036 | 2114.464 |
| LateStg2_021409 | 2287.658 | 2560.275 | 2146.635 | 1698.201 | 2258.806 | 2988.973 |
| LateStg2_021411 | 3275.688 | 5937.628 | 3641.948 | 2783.715 | 3631.025 | 3842.071 |
| LateStg2_021412 | 1421.224 | 1966.427 | 1540.838 | 1344.967 | 1777.86 | 1717.123 |
| LateStg2_021413 | 1909.862 | 8649.381 | 1902.606 | 1753.411 | 2701.412 | 2172.419 |
| LateStg2_021418 | 1400.382 | 1756.549 | 6483.009 | 12480.7 | 1712.24 | 1907.998 |
| LateStg2_021421 | 2016.597 | 3387.465 | 1986.933 | 1592.037 | 2362.854 | 2431.391 |
| LateStg2_021422 | 2534.09 | 9135.84 | 3163.03 | 2608.115 | 3364.623 | 3781.505 |
| LateStg2_021424 | 2096.701 | 5080.653 | 2221.863 | 1669.388 | 2880.509 | 2746.375 |
| LateStg2_021425 | 3821.13 | 5625.683 | 5187.55 | 33888.13 | 10796.37 | 22975.41 |
| LateStg2_021427 | 2006.091 | 4911.945 | 5642.549 | 3571.163 | 2693.277 | 6688.38 |
| LateStg2_021428 | 1391.924 | 1660.351 | 1548.41 | 1357.469 | 9092.653 | 1680.029 |
| LateStg2_021429 | 2844.512 | 4992.574 | 2967.538 | 2066.671 | 3387.576 | 2708.596 |
| LateStg2_021431 | 2317.118 | 4144.749 | 2499.042 | 2225.565 | 3046.623 | 2595.132 |
| LateStg2_021432 | 2551.755 | 4449.926 | 2553.865 | 1790.208 | 2791.503 | 2231.627 |
| LateStg2_021433 | 3632.759 | 7242.118 | 3571.259 | 2868.022 | 4197.165 | 4657.339 |
| LateStg2_021437 | 3358.309 | 36422.07 | 3309.372 | 2486.033 | 4058.445 | 5346.232 |
| LateStg2_021441 | 3184.235 | 23989.57 | 3092.49 | 2360.327 | 4081.13 | 3894.148 |
| LateStg2_021442 | 1953.693 | 3097.947 | 2175.145 | 1574.884 | 2440.885 | 1844.334 |
| LateStg2_021450 | 62465.09 | 9856.237 | 6436.29 | 5774.264 | 8325.764 | 7744.436 |
| LateStg2_021452 | 2628.204 | 7171.939 | 2770.725 | 2191.751 | 3443.649 | 2911.636 |
| LateStg2_021456 | 2295.275 | 2391.687 | 1978.448 | 1735.68 | 3055.247 | 2944.797 |
| LateStg2_021457 | 6740.558 | 13294.24 | 7297.811 | 7370.232 | 26310.33 | 10478.36 |
| LateStg2_021459 | 1799.142 | 3100.266 | 1814.398 | 1634.251 | 2973.406 | 2348.097 |
| LateStg2_021467 | 3031.402 | 9162.167 | 3030.005 | 3013.527 | 5899.702 | 3568.804 |
| LateStg2_021468 | 2555.232 | 5898.635 | 2403.385 | 2061.466 | 3099.336 | 3734.919 |
| LateStg2_021469 | 1346.583 | 2408.616 | 1284.269 | 1075.315 | 1683.193 | 1550.628 |
| LateStg2_021471 | 2345.696 | 6284.123 | 2197.31 | 3165.057 | 2970.156 | 2605.741 |
| LateStg2_021476 | 13932.98 | 5353.104 | 4163.6 | 2583.433 | 3163.012 | 14982.35 |
| LateStg2_021479 | 2786.301 | 3761.414 | 3220.481 | 2663.487 | 3713.563 | 16733.18 |
| LateStg2_021485 | 3572.308 | 22588.2 | 3824.449 | 3019.581 | 4860.078 | 5384.661 |
| LateStg2_021490 | 2700.272 | 5644.643 | 2608.352 | 2090.352 | 3147.381 | 3369.221 |
| LateStg2_021493 | 2513.628 | 4698.848 | 2510.315 | 2021.454 | 2975.269 | 2943.559 |
| LateStg2_021498 | 4285.45 | 7355.246 | 4261.771 | 3229.588 | 5198.682 | 4788.694 |

TABLE 6-continued

| Normalised RFU values for the 19 biomarkers | | | | | |
|---|---|---|---|---|---|
| LateStg2_021499 | 3477.192 | 5287.922 | 3132.654 | 2428.364 | 3670.777 | 4016.163 |
| LateStg2_021803 | 2550.41 | 9028.317 | 2471.884 | 2004.119 | 3726.039 | 3126.381 |
| LateStg2_021817 | 3489.376 | 7562.101 | 2882.902 | 2628.133 | 4314.625 | 3248.255 |
| LateStg2_021819 | 3685.966 | 6583.73 | 3108.269 | 2545.667 | 4423.612 | 3748.161 |
| LateStg2_021821 | 3855.53 | 7804.9 | 3294.47 | 2903.67 | 4701.069 | 3552.171 |
| LateStg2_021828 | 3411.682 | 7526.149 | 3897.674 | 3308.141 | 5139.618 | 4285.685 |
| LateStg2_021833 | 1279.158 | 2007.471 | 1216.094 | 974.8655 | 1689.938 | 1283.639 |
| LateStg2_021838 | 2430.028 | 2848.576 | 2289.099 | 1881.045 | 2790.638 | 2913.932 |
| LateStg2_021841 | 4848.952 | 7746.386 | 7852.988 | 5259.368 | 6938.347 | 7712.883 |
| LateStg2_021846 | 2159.849 | 3125.473 | 1474.7 | 1227.702 | 2012.191 | 1497.391 |
| LateStg2_021854 | 2089.664 | 2749.929 | 2461.663 | 2074.198 | 2346.469 | 2996.54 |
| LateStg2_021856 | 2287.684 | 4127.567 | 2147.37 | 1690.916 | 2545.96 | 2611.793 |
| LateStg2_021857 | 3967.139 | 5754.583 | 3596.755 | 3645.516 | 5079.897 | 5358.171 |
| LateStg2_021859 | 2313.868 | 3634.111 | 1929.03 | 1781.592 | 2948.952 | 2406.479 |
| LateStg2_021860 | 1964.879 | 2275.137 | 1656.999 | 1510.77 | 2197.393 | 2036.264 |
| LateStg2_021863 | 1770.846 | 2499.974 | 1226.013 | 1140.628 | 1928.769 | 1697.19 |
| LateStg2_021865 | 1523.649 | 2533.475 | 1172.621 | 1082.984 | 2098.228 | 1465.648 |
| LateStg2_021868 | 1359.645 | 2195.805 | 1229.105 | 1027.971 | 1746.367 | 1267.317 |
| LateStg2_021871 | 7184.004 | 15378.62 | 6834.217 | 5741.78 | 10556.95 | 7021.684 |
| LateStg2_021880 | 2133.393 | 4583.188 | 1977.947 | 1747.046 | 2667.728 | 2526.626 |
| LateStg2_021881 | 2895.45 | 7062.843 | 2719.433 | 2410.467 | 3115.291 | 4520.945 |
| LateStg2_021883 | 2484.5 | 16564.51 | 2198.001 | 2264.344 | 3763.834 | 17526.91 |
| LateStg2_021890 | 2178.214 | 16641.9 | 2523.614 | 2173.581 | 3724.101 | 2897.678 |
| LateStg2_021891 | 1186.718 | 1491.571 | 1603.177 | 1328.941 | 3133.506 | 3413.422 |
| LateStg2_021892 | 2937.444 | 5562.712 | 3328.625 | 2585.967 | 4427.688 | 3443.103 |
| LateStg2_021894 | 1890.908 | 3334.574 | 2396.437 | 2163.834 | 2887.473 | 3018.096 |
| LateStg2_021897 | 3112.535 | 6338.442 | 2545.71 | 2285.715 | 3852.078 | 3186.883 |
| LateStg2_021959 | 1477.145 | 6609.375 | 1137.616 | 1249.313 | 4849.732 | 1808.159 |
| LateStg2_021961 | 3932.856 | 8437.228 | 3262.102 | 2669.569 | 4774.873 | 3491.703 |
| LateStg2_021499 | 3477.192 | 5287.922 | 3132.654 | 2428.364 | 3670.777 | 4016.163 |

| Protein | RAD23B | STAT1 | TPM1 | XAGE1D | ZNRD1 |
|---|---|---|---|---|---|
| Control1_021608 | 2081.126 | 2617.833 | 4049.264 | 1505.695 | 2626.203 |
| Control1_021611 | 905.2051 | 977.5851 | 1796.781 | 863.7998 | 1532.123 |
| Control1_021630 | 1990.034 | 3163.671 | 6107.433 | 1897.377 | 3821.562 |
| Control1_021631 | 2347.861 | 2764.548 | 4874.361 | 1577.602 | 2855.739 |
| Control1_021642 | 2026.351 | 6089.905 | 4518.586 | 1985.198 | 4152.455 |
| Control1_021643 | 1234.18 | 2229.621 | 2248.575 | 1155.519 | 2530.437 |
| Control1_021650 | 2266.734 | 9483.072 | 4720.325 | 2449.356 | 5897.559 |
| Control1_021660 | 1338.988 | 3689.077 | 4882.12 | 1281.009 | 3234.591 |
| Control1_021661 | 2421.713 | 3949.958 | 6032.581 | 1948.014 | 3304.639 |
| Control1_021663 | 4486.685 | 3322.445 | 3789.802 | 2135.498 | 4907.796 |
| Control1_021674 | 1833.585 | 2449.947 | 8639.902 | 1360.602 | 4240.082 |
| Control1_021679 | 1802.526 | 1950.754 | 2527.683 | 1278.041 | 2860.415 |
| Control1_021680 | 2543.393 | 15907.4 | 4196.795 | 1774.904 | 3386.469 |
| Control1_021681 | 4156.378 | 9128.958 | 19809.27 | 6150.266 | 9369.373 |
| Control1_021682 | 2309.431 | 2437.564 | 3893.909 | 1728.037 | 3301.781 |
| Control2_021005 | 5670.086 | 4960.157 | 22784.55 | 18345.03 | 20955.56 |
| Control2_021007 | 17546.81 | 7313.667 | 7748.537 | 3598.932 | 4526.242 |
| Control2_021016 | 2141.714 | 3366.335 | 5555.07 | 2589.406 | 3272.007 |
| Control2_021017 | 1747.83 | 3847.813 | 4092.125 | 2194.708 | 2639.944 |
| Control2_021025 | 1995.162 | 3132.801 | 4412.822 | 2386.34 | 2807.273 |
| Control2_021037 | 1679.377 | 3354.587 | 4200.855 | 2184.704 | 3093.381 |
| Control2_021038 | 1384.307 | 2710.608 | 3518.954 | 1880.842 | 2744.047 |
| Control2_021045 | 1973.987 | 1904.59 | 3795.172 | 2411.016 | 2970.695 |
| Control2_021046 | 2410.957 | 3980.489 | 5714.518 | 4737.667 | 3939.826 |
| Control2_021401 | 5811.137 | 3107.932 | 7447.278 | 2357.483 | 3127.564 |
| Control2_021405 | 1536.453 | 2455.628 | 3139.008 | 1753.436 | 2103.498 |
| Control2_021406 | 2339.278 | 3625.717 | 3868.642 | 1370.279 | 1894.139 |
| Control2_021419 | 1303.955 | 3515.891 | 2877.05 | 1374.645 | 1776.012 |
| Control2_021420 | 1192.939 | 3347.262 | 3224.197 | 1403.629 | 1900.957 |
| Control2_021423 | 3432.053 | 4868.726 | 11813.17 | 4171.47 | 5555.068 |
| Control2_021426 | 3783.557 | 6349.507 | 6183.704 | 3560.529 | 7570.511 |
| Control2_021430 | 1525.482 | 2578.638 | 70438.51 | 1758.205 | 2714.357 |
| Control2_021436 | 1358.224 | 2193.62 | 2708.096 | 1785.438 | 2455.876 |
| Control2_021451 | 3060.993 | 4270.824 | 6303.973 | 2949.225 | 8755.411 |
| Control2_021453 | 2084.262 | 3021.721 | 6835.281 | 1951.169 | 3240.717 |
| Control2_021454 | 2367.539 | 2441.304 | 4791.178 | 1549.041 | 2289.409 |
| Control2_021455 | 2358.646 | 4807.185 | 6212.127 | 2661.667 | 3698.437 |
| Control2_021463 | 3590.858 | 7434.23 | 9568.385 | 4946.078 | 5981.495 |
| Control2_021470 | 1462.485 | 2516.297 | 10171.16 | 1667.289 | 2791.111 |
| Control2_021477 | 2609.898 | 4227.737 | 7400.694 | 3379.937 | 3876.3 |
| Control2_021478 | 1919.419 | 6160.237 | 4680.497 | 3213.554 | 3278.552 |
| Control2_021484 | 1856.142 | 3234.766 | 4323.386 | 2336.339 | 2965.36 |
| Control2_021494 | 1606.667 | 3721.188 | 2527.812 | 1406.064 | 2014.624 |
| Control2_021495 | 10114.45 | 9327.442 | 13563.37 | 10985.96 | 11552.79 |
| Control2_021497 | 8194.55 | 4910.062 | 4861.554 | 2291.933 | 3220.736 |

TABLE 6-continued

| Normalised RFU values for the 19 biomarkers | | | | | |
|---|---|---|---|---|---|
| Control2_021801 | 2481.315 | 2854.822 | 3918.524 | 2763.663 | 2642.432 |
| Control2_021802 | 1385.581 | 3183.812 | 2829.928 | 1533.262 | 3402.505 |
| Control2_021804 | 2550.711 | 2801.768 | 4235.614 | 2523.631 | 5712.794 |
| Control2_021805 | 2154.696 | 3056.303 | 4473.074 | 1850.957 | 5102.744 |
| Control2_021806 | 2606.994 | 5057.475 | 5208.636 | 2913.279 | 7700.55 |
| Control2_021809 | 3831.109 | 2834.949 | 3286.348 | 1695.697 | 2539.116 |
| Control2_021810 | 2098.649 | 3753.405 | 4439.834 | 2398.99 | 3046.975 |
| Control2_021811 | 1837.785 | 2695.945 | 3664.561 | 1835.566 | 1736.29 |
| Control2_021812 | 3646.176 | 6592.742 | 7476.003 | 4860.687 | 5299.261 |
| Control2_021818 | 1766.938 | 13912.53 | 2448.699 | 1935.279 | 5124.145 |
| Control2_021822 | 1965.292 | 3332.935 | 3820.505 | 2458.486 | 4966.497 |
| Control2_021823 | 1343.488 | 2322.024 | 2924.873 | 1400.678 | 3526.075 |
| Control2_021824 | 1756.883 | 6932.623 | 12069.42 | 5871.825 | 7241.109 |
| Control2_021825 | 2659.892 | 3660.737 | 4434.643 | 3017.324 | 6072.551 |
| Control2_021826 | 1588.61 | 3918.005 | 5187.333 | 2401.518 | 3481.845 |
| Control2_021829 | 974.2268 | 1802.962 | 2828.033 | 1128.866 | 2941.595 |
| Control2_021831 | 1234.548 | 2592.773 | 3259.55 | 1438.736 | 2054.688 |
| Control2_021834 | 2709.399 | 4566.653 | 5304.744 | 2605.529 | 7395.801 |
| Control2_021835 | 1843.991 | 4033.994 | 3249.438 | 2702.522 | 3695.011 |
| Control2_021836 | 2803.469 | 3491.743 | 3627.928 | 1791.521 | 2439.615 |
| Control2_021837 | 1769.233 | 3720.748 | 3504.717 | 1782.507 | 4207.138 |
| Control2_021839 | 2231.778 | 3304.446 | 3685.084 | 2180.862 | 5415.791 |
| Control2_021840 | 1310.607 | 2112.964 | 2436.706 | 1458.616 | 3747.051 |
| Control2_021844 | 2283.847 | 3591.101 | 5118.613 | 2345.115 | 5396.899 |
| Control2_021845 | 2272.65 | 4054.93 | 6627.734 | 2873.661 | 6528.291 |
| Control2_021848 | 1689.162 | 11687.5 | 2823.277 | 1698.773 | 4285.151 |
| Control2_021849 | 3212.107 | 4313.128 | 4844.187 | 1940.267 | 5146.62 |
| Control2_021850 | 1710.077 | 2985.272 | 10907.08 | 2022.729 | 4563.897 |
| Control2_021851 | 2906.247 | 5124.673 | 6914.633 | 3478.561 | 5951.68 |
| Control2_021852 | 1947.486 | 3140.212 | 3194.615 | 2367.34 | 5520.482 |
| Control2_021853 | 1300.163 | 3414.311 | 2726.988 | 1324.848 | 4586.414 |
| Control2_021855 | 4717.033 | 3128.178 | 4070.028 | 2258.982 | 6357.409 |
| Control2_021861 | 1846.351 | 3192.134 | 3243.591 | 1926.237 | 3090.701 |
| Control2_021862 | 1345.939 | 2384.382 | 2742.069 | 1728.213 | 3670.252 |
| Control2_021864 | 1423.723 | 2487.983 | 2064.618 | 1366.074 | 2795.789 |
| Control2_021866 | 3376.394 | 5048.73 | 4946.702 | 3457.549 | 6293.909 |
| Control2_021869 | 2079.015 | 5426.798 | 5380.724 | 4940.874 | 4144.626 |
| Control2_021870 | 2362.266 | 4841.695 | 4649.188 | 2360.201 | 5403.713 |
| Control2_021872 | 1797.54 | 3300.761 | 4053.954 | 2168.691 | 4660.637 |
| Control2_021874 | 2208.745 | 3585.306 | 5739.748 | 2704.132 | 5517.491 |
| Control2_021875 | 1994.916 | 3145.048 | 3000.913 | 2236.848 | 5457.432 |
| Control2_021876 | 3490.562 | 2938.155 | 4877.939 | 1748.16 | 2883.442 |
| Control2_021877 | 2617.009 | 6545.128 | 13734.66 | 3055.266 | 4792.461 |
| Control2_021882 | 2502.86 | 9005.231 | 6358.341 | 2580.803 | 4540.223 |
| Control2_021884 | 2109.724 | 3084.8 | 5077.241 | 2120.757 | 3006.417 |
| Control2_021885 | 3397.924 | 3343.496 | 4043.697 | 2422.662 | 3089.727 |
| Control2_021887 | 1760.354 | 2829.737 | 6973.591 | 1813.83 | 2448.871 |
| Control2_021888 | 2180.773 | 10092.09 | 6037.169 | 2303.328 | 3242.51 |
| Control2_021889 | 1402.45 | 2661.556 | 4983.02 | 1468.28 | 2082.255 |
| Control2_021893 | 1290.029 | 2445.214 | 2708.811 | 1151.813 | 2311.744 |
| Control2_021896 | 1920 | 2577.86 | 5293.315 | 1487.054 | 2189.525 |
| Control2_021898 | 1781.437 | 15068.83 | 4513.11 | 1985.627 | 2620.897 |
| Control2_021899 | 1492.37 | 2394.735 | 3072.453 | 1643.78 | 2270.203 |
| Control2_021900 | 2716.952 | 4014.755 | 5178.692 | 2951.938 | 7874.77 |
| Control2_021962 | 2067.581 | 5010.089 | 4188.351 | 1975.819 | 3179.895 |
| EarlyStg1_021633 | 10190.59 | 2556.25 | 3108.472 | 22871.57 | 2088.815 |
| EarlyStg1_021651 | 2358.632 | 2967.15 | 3584.864 | 1801.215 | 6011.781 |
| EarlyStg1_021654 | 2115.876 | 2382.979 | 3204.194 | 1758.753 | 5859.363 |
| EarlyStg1_021655 | 2346.357 | 2888.672 | 5218.852 | 2056.624 | 4117.299 |
| EarlyStg1_021662 | 1478.589 | 7011.551 | 2377.041 | 18653.11 | 1784.796 |
| EarlyStg1_021675 | 2286.916 | 3358.434 | 5073.502 | 2378.691 | 6228.465 |
| EarlyStg1_021678 | 1124.136 | 1342.022 | 2590.081 | 2450.418 | 2513.441 |
| EarlyStg2_021024 | 1825.564 | 3177.2 | 3875.282 | 2259.64 | 2789.643 |
| EarlyStg2_021403 | 826.697 | 1508.257 | 3280.338 | 1056.332 | 1462.285 |
| EarlyStg2_021435 | 3039.989 | 1482.107 | 1708.522 | 1111.212 | 2970.026 |
| EarlyStg2_021440 | 1274.902 | 2116.541 | 3047.862 | 1489.374 | 2207.21 |
| EarlyStg2_021443 | 6291.922 | 3782.145 | 5357.531 | 2910.532 | 4271.11 |
| EarlyStg2_021458 | 2891.019 | 3304.315 | 5084.472 | 3052.856 | 3851.58 |
| EarlyStg2_021462 | 1220.256 | 1848.675 | 3257.003 | 1419.641 | 1844.949 |
| EarlyStg2_021466 | 2380.558 | 3931.357 | 4237.54 | 5538.389 | 4529.409 |
| EarlyStg2_021489 | 1708.257 | 2492.632 | 3881.379 | 2120.155 | 2455.012 |
| EarlyStg2_021496 | 3119.467 | 4494.802 | 6993.668 | 2825.078 | 3852.443 |
| EarlyStg2_021814 | 1240.605 | 2024.513 | 2875.169 | 1276.932 | 1868.431 |
| EarlyStg2_021815 | 4652.537 | 8918.846 | 13542.18 | 10916.19 | 29827.34 |
| EarlyStg2_021820 | 1846.98 | 2687.747 | 3147.172 | 1999.272 | 4358.43 |
| EarlyStg2_021827 | 735.5688 | 1349.104 | 1553.147 | 807.8251 | 2005.31 |
| EarlyStg2_021830 | 1373.751 | 2402.751 | 2745.201 | 1520.204 | 1758.649 |
| EarlyStg2_021832 | 693.6878 | 1215.148 | 1877.743 | 821.4908 | 989.1862 |

TABLE 6-continued

| | | Normalised RFU values for the 19 biomarkers | | | |
|---|---|---|---|---|---|
| EarlyStg2_021842 | 732.0325 | 1241.119 | 1438.012 | 792.5935 | 1880.585 |
| EarlyStg2_021843 | 1218.456 | 1565.295 | 1760.286 | 1234.466 | 2293.205 |
| EarlyStg2_021847 | 916.262 | 1675.788 | 1953.103 | 1106.615 | 2237.163 |
| EarlyStg2_021858 | 3918.399 | 5739.398 | 7182.912 | 4633.46 | 11607.87 |
| EarlyStg2_021867 | 1508.762 | 2039.943 | 2430.543 | 1407.597 | 3551.464 |
| EarlyStg2_021873 | 2360.751 | 3891.723 | 6348.432 | 2662.724 | 6903.598 |
| EarlyStg2_021895 | 1259.669 | 2291.862 | 2859.402 | 1732.711 | 1940.729 |
| EarlyStg2_021960 | 5344.483 | 5542.575 | 7626.605 | 4567.441 | 6935.041 |
| LateStg1_021607 | 2548.429 | 3653.705 | 11731.3 | 2238.342 | 9084.524 |
| LateStg1_021612 | 1226.084 | 4710.854 | 27371.76 | 24821.54 | 2435.91 |
| LateStg1_021632 | 2239.28 | 1861.048 | 3672.684 | 11641.46 | 2496.863 |
| LateStg1_021683 | 1150.62 | 2402.067 | 3062.754 | 1141.802 | 2028.778 |
| LateStg1_021691 | 2437.998 | 7010.066 | 4723.274 | 4053.18 | 6519.304 |
| LateStg1_021692 | 11902.46 | 6559.493 | 12545.8 | 1963.734 | 11183.95 |
| LateStg1_021696 | 3874.061 | 6828.621 | 7978.743 | 5397.418 | 7341.834 |
| LateStg1_021699 | 1197.207 | 12961.49 | 3163.428 | 1263.17 | 2505.567 |
| LateStg2_021004 | 2755.789 | 2133.374 | 7471.008 | 15774.18 | 4833.175 |
| LateStg2_021006 | 3055.728 | 5022.605 | 13003.68 | 3081.717 | 4111.345 |
| LateStg2_021028 | 4476.661 | 3874.278 | 6939.209 | 15318.87 | 4612.729 |
| LateStg2_021029 | 3731.415 | 3904.665 | 18153.11 | 5939.745 | 9798.426 |
| LateStg2_021039 | 3605.788 | 4050.392 | 11286.33 | 31136.4 | 10124.7 |
| LateStg2_021040 | 2011.853 | 2894.685 | 6237.084 | 12377.03 | 3488.47 |
| LateStg2_021402 | 3864.334 | 2131.699 | 16814.28 | 1855.743 | 2460.073 |
| LateStg2_021404 | 2806.652 | 3262.728 | 5923.29 | 2109.56 | 2837.274 |
| LateStg2_021409 | 6123.263 | 45207.66 | 3710.094 | 2240.805 | 2672.31 |
| LateStg2_021411 | 2780.356 | 9740.508 | 8277.123 | 86593.27 | 4647.849 |
| LateStg2_021412 | 1367.526 | 2384.968 | 2527.974 | 4301.716 | 2051.114 |
| LateStg2_021413 | 2608.381 | 3445.016 | 26526.73 | 2274.128 | 2877.102 |
| LateStg2_021418 | 1232.774 | 2193.431 | 2718.157 | 1707.805 | 2045.315 |
| LateStg2_021421 | 1757.695 | 7521.871 | 6986.991 | 2146.607 | 2784.716 |
| LateStg2_021422 | 2337.046 | 6197.789 | 5642.467 | 51156.32 | 3961.097 |
| LateStg2_021424 | 2017.996 | 3606.207 | 4320.564 | 81892.36 | 3396.019 |
| LateStg2_021425 | 17817.6 | 8637.526 | 10970.58 | 4581.09 | 7241.283 |
| LateStg2_021427 | 2318.45 | 6676.587 | 9097.011 | 5138.452 | 3666.584 |
| LateStg2_021428 | 1365.524 | 3474.558 | 2805.974 | 1418.446 | 3555.568 |
| LateStg2_021429 | 2401.982 | 3614.203 | 5568.374 | 3001.216 | 4089.902 |
| LateStg2_021431 | 2159.14 | 4110.286 | 5855.135 | 2399.371 | 4049.696 |
| LateStg2_021432 | 2113.099 | 3429.028 | 4533.118 | 2518.522 | 3669.681 |
| LateStg2_021433 | 3288.039 | 17338.42 | 7431.575 | 3735.118 | 5408.98 |
| LateStg2_021437 | 5720.515 | 51111.89 | 6558.229 | 73076.88 | 5622.161 |
| LateStg2_021441 | 7333.667 | 5608.731 | 12014.06 | 3198.293 | 5385.842 |
| LateStg2_021442 | 3378.815 | 2767.79 | 3709.88 | 1951.919 | 4524.983 |
| LateStg2_021450 | 9800.541 | 10278.63 | 11756.66 | 8106.801 | 13587.36 |
| LateStg2_021452 | 2955.094 | 3955.263 | 26551.05 | 3107.26 | 4242.407 |
| LateStg2_021456 | 7126.781 | 3647.837 | 4024.424 | 2143.845 | 3360.468 |
| LateStg2_021457 | 6932.051 | 9832.866 | 19790.06 | 7344.632 | 13282.43 |
| LateStg2_021459 | 1709.713 | 2914.202 | 3567.059 | 1904.825 | 2874.884 |
| LateStg2_021467 | 2425.005 | 5735.723 | 5177.811 | 3191.262 | 4545.997 |
| LateStg2_021468 | 2250.546 | 3828.926 | 9905.679 | 2752.943 | 3839.993 |
| LateStg2_021469 | 1463.695 | 2068.044 | 2449.744 | 1328.585 | 2466.248 |
| LateStg2_021471 | 2245.675 | 3627.445 | 14696.91 | 2467.378 | 3167.771 |
| LateStg2_021476 | 2189.458 | 4731.425 | 5321.727 | 21050.91 | 5567.529 |
| LateStg2_021479 | 2874.51 | 4326.346 | 7389.014 | 3331.391 | 4580.993 |
| LateStg2_021485 | 7718.838 | 6508.286 | 11009.77 | 3845.124 | 6364.518 |
| LateStg2_021490 | 3426.851 | 3655.384 | 9930.515 | 2640.637 | 3786.199 |
| LateStg2_021493 | 2136.006 | 54080.8 | 4759.46 | 2612.632 | 3790.428 |
| LateStg2_021498 | 3818.572 | 5490.723 | 12841.46 | 5246.952 | 6432.803 |
| LateStg2_021499 | 2945.576 | 8863.933 | 5309.148 | 3196.865 | 4388.622 |
| LateStg2_021803 | 2455.32 | 3660.465 | 5247.491 | 2842.318 | 5724.04 |
| LateStg2_021817 | 5146.921 | 6176.601 | 6944.245 | 3376.811 | 9550.769 |
| LateStg2_021819 | 3673.165 | 5193.176 | 6400.219 | 3449.647 | 7443.841 |
| LateStg2_021821 | 3290.416 | 5084.206 | 5759.796 | 3728.741 | 8677.661 |
| LateStg2_021828 | 3254.309 | 7498.517 | 9501.756 | 4700.525 | 9935.705 |
| LateStg2_021833 | 1469.673 | 2038.617 | 2763.421 | 1149.49 | 1673.634 |
| LateStg2_021838 | 1876.231 | 3387.326 | 4041.425 | 4749.024 | 5877.246 |
| LateStg2_021841 | 4960.22 | 9289.899 | 9842.119 | 12962.39 | 12360.34 |
| LateStg2_021846 | 1289.456 | 2194.223 | 3448.56 | 1486.978 | 3482.839 |
| LateStg2_021854 | 1614.691 | 2547.062 | 15433.09 | 2182.438 | 2600.972 |
| LateStg2_021856 | 1702.953 | 2811.449 | 6186.714 | 2217.469 | 4138.507 |
| LateStg2_021857 | 4070.815 | 12466.72 | 8308.568 | 4216.411 | 8964.893 |
| LateStg2_021859 | 1991.047 | 3284.598 | 3241.526 | 2186.996 | 4791.754 |
| LateStg2_021860 | 1510.892 | 2753.512 | 3284.302 | 4857.857 | 3644.717 |
| LateStg2_021863 | 1274.661 | 2135.424 | 5495.126 | 77817.12 | 3516.442 |
| LateStg2_021865 | 1554.264 | 2245.101 | 2560.516 | 15878.09 | 2716.509 |
| LateStg2_021868 | 1314.046 | 2054.09 | 2606.964 | 1274.319 | 3338.825 |
| LateStg2_021871 | 7260.707 | 32976.48 | 12429.49 | 8715.363 | 19074.28 |
| LateStg2_021880 | 1632.411 | 3510.768 | 4512.184 | 2456.451 | 3226.212 |
| LateStg2_021881 | 2407.219 | 4258.419 | 12393.42 | 2759.778 | 4259.74 |

TABLE 6-continued

| Normalised RFU values for the 19 biomarkers | | | | | |
|---|---|---|---|---|---|
| LateStg2_021883 | 2545.744 | 4550.17 | 6416.215 | 2650.601 | 3773.043 |
| LateStg2_021890 | 2109.595 | 7377.704 | 5154.293 | 2388.609 | 3284.202 |
| LateStg2_021891 | 1392.966 | 3067.306 | 2590.952 | 1235.433 | 1900.166 |
| LateStg2_021892 | 2566.329 | 4587.612 | 6758.511 | 3181.595 | 4032.283 |
| LateStg2_021894 | 2241.106 | 4094.685 | 4474.155 | 5663.077 | 2795.796 |
| LateStg2_021897 | 2396.901 | 6763.967 | 6534.485 | 2598.865 | 3976.887 |
| LateStg2_021959 | 1777.565 | 2373.879 | 3499.995 | 1359.307 | 2181.833 |
| LateStg2_021961 | 3494.667 | 5256.041 | 6366.071 | 3609.642 | 5268.444 |
| LateStg2_021499 | 2945.576 | 8863.933 | 5309.148 | 3196.865 | 4388.622 |

TABLE 7

| | ROC | Variables | Sens | Spec | ROCSD | SensSD | SpecSD | biomarker.panel | AUC |
|---|---|---|---|---|---|---|---|---|---|
| 1 | 0.832 | 7 | 0.753 | 0.721 | 0.051 | 0.046 | 0.216 | XAGE1D, LRRFIP2, MAGEA10, GAGE2C, STAT1, ZNRD1, RAD23B | 0.818 |
| 2 | 0.819 | 5 | 0.723 | 0.752 | 0.044 | 0.123 | 0.091 | XAGE1D, LRRFIP2, STAT1, FADD, RAD23B | 0.812 |
| 3 | 0.821 | 6 | 0.737 | 0.752 | 0.089 | 0.126 | 0.127 | XAGE1D, LRRFIP2, STAT1, GAGE1, FADD, RAD23B | 0.812 |
| 4 | 0.821 | 11 | 0.770 | 0.623 | 0.081 | 0.126 | 0.059 | XAGE1D, LRRFIP2, GAGE2C, DDX43, STAT1, CT47A1, GAGE1, MAP2K5, CTAG2, FADD, RAD23B | 0.812 |
| 5 | 0.814 | 8 | 0.782 | 0.738 | 0.063 | 0.051 | 0.121 | XAGE1D, LRRFIP2, GAGE1, MAGEA4, STAT1, ZNRD1, CTAG2, CTAG1A | 0.811 |
| 6 | 0.816 | 7 | 0.756 | 0.723 | 0.057 | 0.106 | 0.086 | XAGE1D, DDX43, LRRFIP2, GAGE1, GAGE2C, STAT1, PTPN20A | 0.809 |
| 7 | 0.818 | 8 | 0.754 | 0.681 | 0.083 | 0.119 | 0.107 | XAGE1D, LRRFIP2, DDX43, MAGEA10, GAGE2C, STAT1, CTAG2, ZNRD1 | 0.809 |
| 8 | 0.819 | 6 | 0.740 | 0.799 | 0.117 | 0.138 | 0.091 | XAGE1D, LRRFIP2, MAGEA10, STAT1, RAD23B, CTAG2 | 0.808 |
| 9 | 0.828 | 7 | 0.737 | 0.754 | 0.067 | 0.126 | 0.107 | XAGE1D, CT47A1, LRRFIP2, GAGE1, STAT1, ZNRD1, RAD23B | 0.808 |
| 10 | 0.815 | 11 | 0.768 | 0.753 | 0.031 | 0.117 | 0.085 | XAGE1D, LRRFIP2, GAGE2C, CT47A1, STAT1, GAGE1, MAGEA4, ZNRD1, DDX53, MAP2K5, RAD23B | 0.808 |
| 11 | 0.807 | 8 | 0.695 | 0.738 | 0.058 | 0.141 | 0.044 | XAGE1D, LRRFIP2, DDX43, STAT1, GAGE2C, MAGEA10, GAGE1, FADD | 0.807 |
| 12 | 0.813 | 5 | 0.742 | 0.738 | 0.093 | 0.146 | 0.131 | XAGE1D, LRRFIP2, STAT1, FADD, CTAG2 | 0.807 |
| 13 | 0.809 | 9 | 0.766 | 0.769 | 0.081 | 0.135 | 0.115 | XAGE1D, LRRFIP2, DDX43, GAGE1, STAT1, MAGEA4, CTAG2, RAD23B, FADD | 0.807 |
| 14 | 0.826 | 8 | 0.724 | 0.740 | 0.086 | 0.179 | 0.138 | XAGE1D, LRRFIP2, DDX43, GAGE2C, CT47A1, STAT1, CTAG2, RAD23B | 0.807 |

The invention claimed is:

1. A composition comprising a panel of antigens comprising biotinylated proteins, wherein the biotinylated proteins consist of X Antigen Family Member 1D (XAGE1D), LLR Binding FLII Interacting Protein 2 (LRRFIP2), G Antigen 2C (GAGE2C), MAGE Family Member A10 (MAGEA10), Signal Transducer and Activator of Transcription 1 (STAT 1), Zinc Ribbon Domain-Containing 1 (ZNRD1), and RAD23 Homolog B (RAD23B).

2. The composition according to claim 1 wherein each biotinylated protein is formed from a Biotin Carboxyl Carrier Protein folding marker which is fused in-frame with a protein.

3. The composition according to claim 1 wherein the biotinylated proteins are bound to a streptavidin-coated substrate.

4. The composition according to claim 3 wherein the substrate comprises a hydrogel-forming polymer base layer.

5. A composition according to claim 1 wherein the amount of one or more exosomal autoantibody biomarkers binding in vitro to the antigens in a sample from a patient can be measured to determine the presence of non-small cell lung cancer.

6. A composition for detecting non-small cell lung cancer, which comprises a panel of antigens bound to a substrate, wherein the antigens consist of X Antigen Family Member 1D (XAGE1D), LLR Binding FLII Interacting Protein 2 (LRRFIP2), G Antigen 2C (GAGE2C), MAGE Family Member A10 (MAGEA 10), Signal Transducer and Activator of Transcription 1 (STAT 1), Zinc Ribbon Domain-Containing 1 (ZNRD 1), and RAD23 Homolog B (RAD23B).

7. The composition according to claim 6, wherein the substrate comprises a glass slide, biochip, strip, slide, bead, microtitre plate well, surface plasmon resonance support, microfluidic device, thin film polymer base layer, hydrogel-forming polymer base layer, or any other device or technology suitable for detection of antibody-antigen binding.

8. The composition according to claim 6, wherein the antigens are biotinylated proteins.

9. The composition according to claim 8, wherein each biotinylated protein is formed from a Biotin Carboxyl Carrier Protein folding marker which is fused in-frame with a protein.

10. The composition according to claim 6, wherein the substrate is streptavidin-coated.

11. The composition according to claim 6, wherein the substrate comprises a hydrogel-forming polymer base layer.

12. The composition according to claim 6 wherein the amount of one or more exosomal autoantibody biomarkers binding in vitro to the antigens in a sample from a patient can be measured to determine the presence of non-small cell lung cancer.

13. A composition for detecting non-small cell lung cancer, which comprises a panel of antigens comprising biotinylated proteins, wherein the biotinylated proteins consist of X Antigen Family Member 1D (XAGE1D), LLR Binding FLII Interacting Protein 2 (LRRFIP2), G Antigen 2C (GAGE2C), MAGE Family Member A10 (MAGEA 10), Signal Transducer and Activator of Transcription 1 (STAT

108

1), Zinc Ribbon Domain-Containing 1 (ZNRD 1), and RAD23 Homolog B (RAD23B).

14. The composition according to claim 13, wherein each biotinylated protein is formed from a Biotin Carboxyl Carrier Protein folding marker which is fused in-frame with a protein.

15. The composition according to claim 13, wherein the antigens are bound to a substrate.

16. The composition according to claim 15, wherein the substrate is streptavidin-coated.

17. The composition according to claim 15, wherein the substrate comprises a hydrogel-forming polymer base layer.

18. The composition according to claim 15, wherein the substrate comprises a glass slide, biochip, strip, slide, bead, microtitre plate well, surface plasmon resonance support, microfluidic device, thin film polymer base layer, hydrogel-forming polymer base layer, or any other device or technology suitable for detection of antibody-antigen binding.

19. The composition according to claim 13 wherein the amount of one or more exosomal autoantibody biomarkers binding in vitro to the antigens in a sample from a patient can be measured to determine the presence of non-small cell lung cancer.

\* \* \* \* \*

SEQUENCE LISTING

<160> NUMBER OF SEQ ID NOS: 38

<210> SEQ ID NO 1
<211> LENGTH: 243
<212> TYPE: DNA
<213> ORGANISM: Homo sapiens

<400> SEQUENCE: 1
atggaatccc ccaagaagaa gaaccagcag ctgaaggtcg gaatcctgca cctgggttcc       60
cgtcagaaga agatccgtat ccagctgcgt tcccagtgcg ctacctggaa ggtcatctgc      120
aagtcctgca tctcccagac ccccggtatc aacctggacc tgggctccgg tgtcaaggtc      180
aagatcatcc ccaaggaaga acactgcaag atgcccgagg ctggcgagga acagccccag      240
gtg                                                                   243

<210> SEQ ID NO 2
<211> LENGTH: 1200

```
<212> TYPE: DNA
<213> ORGANISM: Homo sapiens

<400> SEQUENCE: 2
atggggactc ctgcttctgg aaggaaaaga acacctgtga aagaccgatt ttctgcagaa      60
gatgaagctt tgagtaacat tgccagagag gcagaggcaa ggctggcagc aaaacgggct     120
gcccgggcag aagcaagaga tatacgcatg agagaactgg aacgacaaca aaaagagttg     180
gatgaaaaat ctgacaaaca gtatgctgaa aattatacaa gaccttcatc tcgaaattct     240
gcctcagcaa caacccctct aagtggaaac tcatccagac gaggaagtgg ggacaccagc     300
agcttaatag atccagacac ttcattaagt gaattgcggg aatctttgtc tgaagtggaa     360
gaaaaataca agaaagccat ggtttccaat gcacagttag acaatgagaa gaacaatttg     420
atctaccaag tagacacact caaggatgtt attgaagagc aggaggaaca gatggcagaa     480
ttttatagag aaaatgaaga aaaatcaaag gagttagaaa ggcagaaaca tatgtgtagt     540
gtgctgcagc ataagatgga agaacttaaa gaaggcctgc ggcaaagaga tgagcttatt     600
gagaaacatg gcttagttat aatccccgat ggcactccca atggtgatgt cagtcatgaa     660
ccagtggctg gagccatcac tgttgtgtct caggaagctg ctcaggtctt ggagtcagca     720
ggagaagggc cattagatgt aaggctacga aaacttgctg gagagaagga agaactactg     780
tcacagatta gaaaactgaa gcttcagtta gaggaggaac gacagaaatg ctccaggaat     840
gatggcacag tgggtgacct ggcaggactg cagaatggct cagacttgca gttcatcgaa     900
atgcagagag atgccaatag acaaattagc gaatacaaat ttaagctttc aaaagcagaa     960
caggatataa ctaccttgga gcaaagtatt agccggcttg agggacaggt tctgagatat    1020
aaaactgctg ctgagaatgc tgagaaagtt gaagatgaat tgaaagcaga aaaacggaag    1080
ctacaacgag agttacgaac agcactggac aagattgagg agatggagat gaccaacagc    1140
cacctggcca agcggctgga agatgaag gccaatagga cagcacttct ggcccagcag    1200

<210> SEQ ID NO 3
<211> LENGTH: 348
<212> TYPE: DNA
<213> ORGANISM: Homo sapiens

<400> SEQUENCE: 3
atgtcctggc gtggtcgttc cacctaccgt ccccgtcctc gtcgttacgt cgagcccccc      60
gagatgatcg gtcccatgcg tcccgagcag ttctccgacg aggtcgagcc cgctaccccc     120
gaggaaggcg agcctgctac tcagcgtcag gaccccgctc tgctcaaga gggcgaggac     180 gagggcgctt ccgctggcca gggtcctaag cccgaggctc actcccaaga gcagggtcac     240
ccccagaccg gttgcgagtg cgaggacggt cccgacggtc aagagatgga cccccccaac     300
cctgaggaag tcaagacccc cgaagagggc gaaaagcagt cccagtgc                   348

<210> SEQ ID NO 4
<211> LENGTH: 1893
<212> TYPE: DNA
<213> ORGANISM: Homo sapiens

<400> SEQUENCE: 4
atgtcccact gggctcccga gtggaagcgt gctgaggcta accccgtga cctgggcgct      60 tcttgggacg tgcgcggttc ccgtggtagc ggttggagcg tcccttcgg tcaccaaggt     120 ccccgtgctg ctggttcccg cgagcccccc ctgtgcttca agatcaagaa caacatggtc     180
```

```
ggagtggtca tcggttactc cggttccaag atcaaggacc tgcagcactc caccaacacc       240
aagatccaga tcatcaacgg cgagtccgag gctaaggtcc gcatcttcgg caaccgcgag       300
atgaaggcta aggccaaggc tgctatcgag actctgatcc gcaagcaaga gtcctacaac       360
tccgagtcct ccgtggacaa cgctgcttcc cagacccca tcggtcgtaa cctgggtcgt       420
aacgacatcg tgggcgaggc tgagccctg tccaactggg accgtatccg cgctgctgtg       480
gtcgagtgcg agaagcgcaa gtgggctgac ctgcccccg tgaagaagaa cttctacatc       540
gagtccaagg ctacctcctg catgtccgag atgcaagtga tcaactggcg caaggaaaac       600
ttcaacatca cttgcgacga cctgaagtcc ggcgagaagc gtctgatccc caagcctacc       660
tgccgtttca aggacgcttt ccagcagtac cccgacctgc tgaagtccat catccgtgtg       720
ggtatcgtga gcccacccc catccagtcc caggcttggc caatcatcct gcagggtatc       780
gacctgatcg tggtggctca gaccggcacc ggcaagaccc tgtcctacct gatgcccggt       840
ttcatccacc tggactccca gcccatcctc cgcgagcagc gtaacggtcc cggcatgctg       900
gtgctgaccc ctacccgtga actggctctg cacgtcgagg ctgagtgctc caagtactcc       960 tacaagggc tgaagtctat ctgcatctac ggtggtcgta accgtaacgg ccagatcgag      1020
gacatctcca agggtgtcga catcatcatt gctacccccg tcgtctgaa cgacctgcag      1080 atgaacaact ccgtgaacct gcgttccatc acctacctgg tcatcgacga ggctgacaag      1140
atgctggaca tggagttcga gccccagatc cgcaagatcc tgctggacgt gcgtcccgac      1200
cgtcagaccg tgatgacctc cgctacctgg cccgacaccg tgcgtcagct ggctctgtct      1260
tacctgaagg accccatgat cgtgtacgtg ggcaacctga acctggtggc tgtgaacacc      1320
gtgaagcaga acatcatcgt gaccaccgag aaggaaaaga gggctctgac ccaagagttc      1380
gtcgagaaca tgtcccccaa cgacaaggtc atcatgttcg tgtcccagaa gcacattgct      1440
gacgacctgt cctccgattt caacatccaa ggcatctccg ctgagtccct gcacggcaac      1500
tccgagcagt ccgaccaaga gcgtgctgtc gaggacttca gtccggcaa catcaagatc      1560 ctcatcacca ccgacatcgt gtcccgtggc ctggacctga cgacgtgac ccacgtgtac      1620 aactacgact cccccgtaa catcgacgtg tacgtgcacc gtgtgggtta catcggtcgc      1680
accggaaaga ccggaacctc cgtgaccctg atcacccagc gcgactccaa gatggctggc      1740
gagctgatca agatcttgga ccgtgctaac cagtccgtgc ccgaggacct ggtggtcatg      1800
gctgagcagt acaagctgaa ccagcagaag cgtcaccgcg agactcgttc ccgcaagccc      1860
ggacagcgtc gcaaggagtt ctacttcctg tcc                                   1893
```

```
<210> SEQ ID NO 5
<211> LENGTH: 1944
<212> TYPE: DNA
<213> ORGANISM: Homo sapiens

<400> SEQUENCE: 5
atgtcccacc acggtggtgc tcccaaggct tccacctggg tggtggcttc ccgtcgttcc        60
tccaccgtgt cccgtgctcc cgagcgtcgt cccgctgagg aactgaaccg taccggtccc       120
gagggctact ccgtgggtcg tggtggtcgt tggcgtggca cctctcgtcc ccctgaggct       180
gtggctgctg gtcacgagga actgcccctg tgcttcgctc tgaagtccca cttcgtgggt       240
gctgtgatcg tcgcggtgg ttccaagatc aagaacatcc agtccaccac caacaccacc       300
atccagatca tccaagagca gcccgagtcc ctggtcaaga tcttcggttc caaggctatg       360
cagaccaagg ctaaggctgt gatcgacaac ttcgtgaaga agctggaaga gaactacaac       420
```

```
tccgagtgcg gtatcgacac cgctttccag ccctccgtgg gcaaggacgg ttccaccgac    480
aacaacgtgg tggctggcga ccgtcccctg atcgactggg accagatccg tgaagagggc    540
ctgaagtggc aaaagaccaa gtgggctgac ctgccccccca tcaagaagaa cttctacaag    600
gaatccaccg ctacctccgc tatgtccaag gtcgaggctg actcctggcg caaggaaaac    660
ttcaacatca cctgggacga cctgaaggac ggcgagaagc gtcccatccc caaccctacc    720
tgcaccttcg acgacgcttt ccagtgctac cccgaagtga tggaaaacat caagaaggct    780
ggtttccaga agcccacccc catccagtcc caggcttggc ccatcgtgct gcagggtatc    840
gacctgatcg gtgtcgctca gaccggcacc ggcaagaccc tgtgctacct gatgcccggt    900
ttcatccacc tggtgctgca gccctccctg aagggccagc gtaaccgtcc cggcatgctg    960
gtgctgaccc ctaccgcga actggctctg caggtcgagg cgagtgctg caagtactcc     1020 tacaagggcc tgcgttccgt gtgcgtgtac ggtggtggca accgtgacga gcagatcgag    1080
gaactcaaga agggtgtcga catcatcatc gctaccccg gtcgtctgaa cgacctgcag     1140
atgtccaact tcgtcaacct gaagaacatc acctacctgg tcctggacga ggctgacaag    1200
atgctggaca tgggtttcga gccccagatc atgaagatcc tgctggacgt gcgtcccgac    1260
cgtcagaccg tgatgacctc cgctacctgg ccccactccg tgcaccgtct ggctcagtcc    1320
tacctgaagg aacccatgat cgtgtacgtg ggcaccctgg acctggtggc tgtgtcctcc    1380
gtgaagcaga acatcatcgt gaccaccgag aagagaagt ggtcccacat gcagactttc     1440
ttgcagtcca tgtcctctac cgacaaggtc atcgtgttcg tgtcccgcaa ggctgtcgct    1500
gaccacctgt cctccgacct gatcctgggc aacatctccg tcgagtccct gcacggcgac    1560
cgcgagcagc gtgaccgcga gaaggctctc gagaacttca agaccggcaa ggtccgcatc    1620
ctgatcgcta ccgacctggc tttcccgcgga ctggacgtgc acgacgtgac ccacgtgtac    1680
aacttcgact tccccccgtaa catcgaggaa tacgtgcacc gtatcggtcg taccggtcgt    1740
gctggtcgca ccggtgtctc catcaccacc ctgacccgta acgactggcg tgtggcttcc    1800
gagctgatca acatcctcga gcgtgctaac cagtccatcc ccgaggaact ggtgtctatg    1860
gctgagcgtt tcaaggctca ccagcaaaag cgcgagatgg aacgcaagat ggaacgtccc    1920
cagggtcgtc ccaagaagtt ccac                                          1944
```

<210> SEQ ID NO 6
<211> LENGTH: 351
<212> TYPE: DNA
<213> ORGANISM: Homo sapiens

<400> SEQUENCE: 6

```
atgtcctggc gtggtcgttc cacctactac tggccccgtc cccgtcgtta cgtgcagccc     60
cccgagatga tcggtcccat gcgtcccgag cagttctccg acgaggtcga gcccgctacc    120
cccgaggaag gcgagcctgc tactcagcgt caggaccccg ctgctgctca agagggcgag    180
gacgagggcg cttccgctgg ccagggtcct aagcccgagg ctgactccca agagcagggt    240 caccccaga ccggttgcga gtgcgaggac ggtcccgacg tcaagagat ggacccccc       300 aaccctgagg aagtcaagac ccccgaagag ggcgaaggcc agtcccagtg c             351
```

<210> SEQ ID NO 7
<211> LENGTH: 1107
<212> TYPE: DNA
<213> ORGANISM: Homo sapiens

```
<400> SEQUENCE: 7
atgccccgtg ctcccaagcg tcagcgttgc atgcccgaag aggacctgca gtcccagtcc        60
gagactcagg gcctcgaggg tgctcaggct cccctggctg tggaagagga cgcttccagc       120
tctacctcta cctcctccag cttccccagc agcttcccat cctccagctc ctctagctcc       180
tcctcctgct acccctgat  cccctccacc cccgaggaag tgtccgctga cgacgagact       240
cccaaccccc cccagtccgc tcagatcgct tgctcctccc cctccgtggt ggcttccctg       300
cctctggacc agtccgacga gggttccagc tcccagaagg aagagtcccc cagcaccctg       360
caggtcctgc ccgactccga gtccctgccc cgttccgaga tcgacgagaa ggttacagac       420
ctggtgcagt tcctgctgtt caagtaccag atgaaggaac ccatcaccaa ggctgagatc       480
ctcgagtccg tgatcaagaa ctacgaggac cacttccccc tgctgttctc cgaggcttcc       540
gagtgcatgc tgctggtgtt cggtatcgac gtgaaggaag tggaccctac cggtcactcc       600
ttcgtgctgg tcacctccct gggcctgacc tacgacggca tgctgtccga cgtgcagtcc       660
atgcccaaga ccggtatcct gatcctcatc ctgtccatca tcttcatcga gggctactgc       720
actcctgagg aagtgatctg ggaggctctg aacatgatgg gcctgtacga cggaatggaa       780
cacctgatct acggcgagcc ccgcaagctg ctgacccagg actgggtgca agagaactac       840
ctcgagtacc gtcaggtgcc cggttccgac cccgctcgtt acgagttcct gtggggtccc       900
cgtgctcacg ctgagatccg caagatgtcc ctgctgaagt tcctggctaa ggtcaacggc       960 tccgacccec gttccttccc actgtggtac gaggaagctc tgaaggacga ggaagagagg      1020
gctcaggacc gtatcgctac caccgacgac accaccgcta tggcttccgc ttcctctagc      1080
gctaccggtt ccttcagcta ccccgag                                         1107

<210> SEQ ID NO 8
<211> LENGTH: 378
<212> TYPE: DNA
<213> ORGANISM: Homo sapiens

<400> SEQUENCE: 8
atgtctgtca tggacctcgc caatacttgc tccagctttc agtcggacct ggatttctgt        60
tcagattgcg gctcggtcct gcctctgccc ggggctcagg atacggtcac ctgtattcgc       120
tgtggcttca acatcaacgt tcgggacttt gaggggaagg ttgtgaagac ttcggttgtg       180
ttccaccaac tggggacagc catgcctatg tcggtggagg aagggcctga gtgccaggga       240
cctgtggttg acaggcgctg ccctcgatgt ggtcatgaag gaatggcata ccacaccaga       300
cagatgcgtt cagccgatga agggcaaact gtcttctaca cctgtaccaa ctgcaagttc       360
caggagaagg aagactct                                                     378

<210> SEQ ID NO 9
<211> LENGTH: 1344
<212> TYPE: DNA
<213> ORGANISM: Homo sapiens

<400> SEQUENCE: 9
atgctgtggc tagcccttgg ccccttttcct gccatggaga accaggtgct ggtaattcgc        60
atcaagatcc caaatagtgg cgcggtggac tggacagtgc actccgggcc gcagttactc       120
ttcagggatg tgctggatgt gataggccag gttctgcctg aagcaacaac tacagcattt       180
gaatatgaag atgaagatgg tgatcgaatt acagtgagaa gtgatgagga aatgaaggca       240
atgctgtcat attattattc cacagtaatg gaacagcaag taaatggaca gttaatagag       300
```

-continued

```
cctctgcaga tatttccaag agcctgcaag cctcctgggg aacgaacat  acatggcctg      360 aaggtgaata ctcgggccgg accctctcaa cacagcagcc cagcagtctc agattcactt      420
ccaagcaata gcttaaagaa gtcttctgct gaactgaaaa aaatactagc caatggccag      480
atgaatgaac aagacatacg atatcgggac actcttggtc atggcaacgg aggcacagtc      540
tacaaagcat atcatgtccc gagtgggaaa atattagctg taaaggtcat actactagat      600
attacactgg aacttcagaa gcaaattatg tctgaattgg aaattcttta taagtgcgat      660
tcatcatata tcattggatt ttatggagca ttttttgtag aaaacaggat ttcaatatgt      720
acagaattca tggatggggg atctttggat gtatatagga aaatgccaga acatgtcctt      780
ggaagaattg cagtagcagt tgttaaaggc cttacttatt tgtggagttt aaagatttta      840
catagagacg tgaagccctc caatatgcta gtaaacacaa gaggacaggt taagctgtgt      900
gattttggag ttagcactca gctggtgaat tctatagcca agacgtatgt tggaacaaat      960
gcttatatgg cgcctgaaag gatttcaggg gagcagtatg gaattcattc tgatgtctgg     1020
agcttaggaa tctctttat ggagcttgct cttgggaggt ttccatatcc tcagattcag     1080
aaaaaccagg gatctttaat gcctctccag cttctgcagt gcattgttga tgaggattcg     1140
cccgtccttc cagttggaga gttctcggag ccatttgtac atttcatcac tcagtgtatg     1200
cgaaaacagc caaagaaag gccagcacct gaagaattga tgggccaccc gttcatcgtg     1260
cagttcaatg atggaaatgc cgccgtggtg tccatgtggg tgtgccgggc gctggaggag     1320
aggcggagcc agcaggggcc cccg                                          1344
```

<210> SEQ ID NO 10
<211> LENGTH: 951
<212> TYPE: DNA
<213> ORGANISM: Homo sapiens

<400> SEQUENCE: 10

```
atgtcttctg agcagaagag tcagcactgc aagcctgagg aaggcgttga ggcccaagaa       60
gaggccctgg gcctggtggg tgcacaggct cctactactg aggagcagga ggctgctgtc      120
tcctcctcct ctcctctggt ccctggcacc ctggaggaag tgcctgctgc tgagtcagca      180
ggtcctcccc agagtcctca gggagcctct gccttaccca ctaccatcag cttcacttgc      240
tggaggcaac ccaatgaggg ttccagcagc caagaagagg aggggccaag cacctcgcct      300
gacgcagagt ccttgttccg agaagcactc agtaacaagg tggatgagtt ggctcatttt      360
ctgctccgca gtatcgagc caaggagctg gtcacaaagg cagaaatgct ggagagagtc      420
atcaaaaatt acaagcgctg ctttcctgtg atcttcggca aagcctccga gtccctgaag      480
atgatctttg gcattgacgt gaaggaagtg acccccacca gcaacaccta caccettgtc      540 acctgcctgg gcctttccta tgatggcctg ctgggtaata atcagatctt tcccaagaca      600
ggccttctga taatcgtcct gggcacaatt gcaatggagg gcgacagcgc ctctgaggag      660
gaaatctggg aggagctggg tgtgatgggg gtgtatgatg ggagggagca cactgtctat      720
ggggagccca ggaaactgct cacccaagat tgggtgcagg aaaactacct ggagtaccgg      780
caggtacccg gcagtaatcc tgcgcgctat gagttcctgt ggggtccaag ggctctggct      840
gaaaccagct atgtgaaagt cctggagcat gtggtcaggg tcaatgcaag agttcgcatt      900
gcctacccat ccctgcgtga agcagctttg ttagaggagg aagagggagt c               951
```

<210> SEQ ID NO 11

-continued

```
<211> LENGTH: 2136
<212> TYPE: DNA
<213> ORGANISM: Homo sapiens

<400> SEQUENCE: 11
atgtctcagt ggtacgaact tcagcagctt gactcaaaat tcctggagca ggttcaccag     60
ctttatgatg acagttttcc catggaaatc agacagtacc tggcacagtg gttagaaaag    120
caagactggg agcacgctgc caatgatgtt tcatttgcca ccatccgttt tcatgacctc    180
ctgtcacagc tggatgatca atatagtcgc ttttctttgg agaataactt cttgctacag    240
cataacataa ggaaaagcaa gcgtaatctt caggataatt ttcaggaaga cccaatccag    300
atgtctatga tcatttacag ctgtctgaag gaagaaagga aaattctgga aaacgcccag    360
agatttaatc aggctcagtc ggggaatatt cagagcacag tgatgttaga caaacagaaa    420
gagcttgaca gtaaagtcag aaatgtgaag gacaaggtta tgtgtataga gcatgaaatc    480
aagagcctgg aagatttaca agatgaatat gacttcaaat gcaaaacctt gcagaacaga    540
gaacacgaga ccaatggtgt ggcaaagagt gatcagaaac aagaacagct gttactcaag    600
aagatgtatt taatgcttga caataagaga aaggaagtag ttcacaaaat aatagagttg    660
ctgaatgtca ctgaacttac ccagaatgcc ctgattaatg atgaactagt ggagtggaag    720
cggagacagc agagcgcctg tattgggggg ccgcccaatg cttgcttgga tcagctgcag    780
aactggttca ctatagttgc ggagagtctg cagcaagttc ggcagcagct taaaaagttg    840
gaggaattgg aacagaaata cacctacgaa catgacccta tcacaaaaaa caaacaagtg    900
ttatgggacc gcaccttcag tcttttccag cagctcattc agagctcgtt tgtggtggaa    960
agacagccct gcatgccaac gcaccctcag aggccgctgg tcttgaagac aggggtccag   1020
ttcactgtga agttgagact gttggtgaaa ttgcaagagc tgaattataa tttgaaagtc   1080
aaagtcttat ttgataaaga tgtgaatgag agaaatacag taaaaggatt taggaagttc   1140
aacattttgg gcacgcacac aaaagtgatg aacatggagg agtccaccaa tggcagtctg   1200
gcggctgaat ttcggcacct gcaattgaaa gaacagaaaa atgctggcac cagaacgaat   1260
gagggtcctc tcatcgttac tgaagagctt cactccctta gttttgaaac ccaattgtgc   1320
cagcctggtt tggtaattga cctcgagacg acctctctgc ccgttgtggt gatctccaac   1380
gtcagccagc tcccgagcgg ttgggcctcc atcctttggt acaacatgct ggtggcggaa   1440
cccaggaatc tgtccttctt cctgactcca ccatgtgcac gatgggctca gctttcagaa   1500
gtgctgagtt ggcagttttc ttctgtcacc aaaagaggtc tcaatgtgga ccagctgaac   1560
atgttgggag agaagcttct tggtcctaac gccagccccg atggtctcat tccgtggacg   1620
aggttttgta aggaaaatat aaatgataaa aattttccct tctggctttg gattgaaagc   1680
atcctagaac tcattaaaaa acacctgctc cctctctgga atgatgggtg catcatgggc   1740
ttcatcagca aggagcgaga gcgtgccctg ttgaaggacc agcagccggg gaccttcctg   1800
ctgcggttca gtgagagctc ccgggaaggg gccatcacat tcacatgggt ggagcggtcc   1860
cagaacggag gcgaacctga cttccatgcg gttgaaccct acacgaagaa agaactttct   1920
gctgttactt tccctgacat cattcgcaat tacaaagtca tggctgctga gaatattcct   1980
gagaatcccc tgaagtatct gtatccaaat attgacaaag accatgcctt tggaaagtat   2040
tactccaggc caaaggaagc accagagcca atggaacttg atggccctaa aggaactgga   2100
tatatcaaga ctgagttgat ttctgtgtct gaagtg                             2136
```

-continued

```
<210> SEQ ID NO 12
<211> LENGTH: 864
<212> TYPE: DNA
<213> ORGANISM: Homo sapiens

<400> SEQUENCE: 12
atgtccgcta ccggcgaccg tcaccctacc cagggcgacc aagaggctcc cgtgtcccaa      60
gagggtgctc aggctgaggc tgctggtgct ggcaaccagg aaggtggcga ctccggtccc     120
gactcctccg acgtggtgcc tgctgctgag gtcgtgggtg tcgctggtcc tgtcgagggc     180
ctgggagagg aagagggcga gcaggctgct ggcctggctg ctgtgcctcg tggtggttcc     240
gctgaagagg actccgacat cggtcccgct accgaggaag aggaagaaga agagggcaac     300
gaggctgcta acttcgacct ggctgtggtg gctcgtcgtt accccgcttc cggtatccac     360
ttcgtgctgc tggacatggt gcactccctg ctgcaccgtc tgtcccacaa cgaccacatc     420
ctgatcgaga accgtcagct gtcccgtctg atggtcggac cccacgctgc tgctcgtaac     480
ctgtggggca acctgccccc cctgctgctg cctcaacgtc tgggagctgg tgctgctgct     540
agggctggcg agggactggg cctgatccaa gaggctgctt ccgtgcccga gcccgctgtg     600
cctgctgact tggctgagat ggcccgcgag cctgctgagg aagctgctga agagaagctg     660
tccgaggaag ccaccgagga acccgacgct gaggaaccag ctactgagga acccaccgct     720
caagaggcta ccgctcctga ggaagtgacc aagtcccagc ccgagaagtg ggacgaggaa     780
gctcaggacg ctgctggcga ggaagagaag aacaagaaa aggaaaagga cgccgagaac     840
aaggtcaaga actccaaggg cacc                                           864

<210> SEQ ID NO 13
<211> LENGTH: 1737
<212> TYPE: DNA
<213> ORGANISM: Homo sapiens

<400> SEQUENCE: 13
atgaacaagc tgtacatcgg caacctgtcc gagaacgctg ctccctccga cctcgagtcc      60
atcttcaagg acgctaagat ccccgtgtcc ggacccttcc tggtcaagac cggttacgct     120
ttcgtggact gccccgacga gtcctgggct ctgaaggcta tcgaggctct gtccggcaag     180
atcgagctgc acggcaagcc catcgaggtc gagcactccg tgcccaagcg tcagcgtatc     240
cgcaagctgc agatccgtaa catccccca cacctccagt gggaggtgct ggactccctg     300
ctggtgcagt acggtgtcgt cgagtcctgc gagcaagtga acaccgactc cgagactgct     360
gtggtcaacg tgacctactc ctccaaggac caggctcgtc aggctctgga caagctgaac     420
ggtttccagc tcgagaactt caccctgaag gtggcctaca tccccgacga gatggctgct     480
cagcagaacc ccctgcagca gccccgtggt cgtcgtggac tgggacagcg tggtagctcc     540
cgtcagggtt cccccggttc cgtgtccaag cagaagccct gcgacctgcc cctgcgtctg     600
ctggtgccta cccagttcgt gggtgctatc atcggcaagg aaggtgctac catccgcaac     660
atcaccaagc agacccagtc caagatcgac gtccaccgca aggaaaacgc tggcgctgct     720
gagaagtcca tcaccatcct gtccacccc gagggcacct ccgctgcttg caagtccatc     780
ctcgagatca tgcacaagga gcccaggac atcaagttca ccgaggaaat ccccctgaag     840
atcctggctc acaacaactt cgtgggtcgt ctgatcggaa aggaaggccg taacctgaag     900
aagatcgagc aggacaccga caccaagatc accatctccc cactgcaaga gctgaccctg     960
tacaaccccg agcgtaccat caccgtgaag ggcaacgtgg aaacctgcgc taaggctgaa    1020
```

-continued

```
gaggaaatca tgaagaagat ccgcgagtcc tacgagaacg atatcgcttc catgaacctg       1080
caggctcacc tgatccccgg cctgaacctg aacgctctgg gcctgttccc ccctacctcc       1140
ggcatgcctc ctcccacctc tggtccccc  tccgctatga ccccccata ccccagttc        1200 gagcagtccg agactgagac tgtgcacctg ttcatccccg ctctgtccgt cggtgccatc       1260
atcggaaagc agggccagca catcaagcag ctgtcccgtt cgctggtgc ttccatcaag        1320 atcgctcccg ctgaggctcc cgacgctaag gtccgcatgg tcatcatcac cggtcccccc       1380
gaggctcagt tcaaggctca gggtcgtatc tacggcaaga tcaaggaaga gaacttcgtc       1440
agccccaagg aagaagtgaa gctcgaggct cacatccgtg tgccatcctt cgctgctggt       1500
cgtgttatcg gcaagggtgg caagaccgtg aacgagctgc agaacctgtc ctccgctgag       1560
gtggtggtgc ccgtgacca gaccctgac  gagaacgacc aggtggtggt caagatcacc        1620
ggtcacttct acgcttgcca ggtggcccag cgcaagatcc aagagatcct gacccaagtg       1680
aagcagcacc agcagcagaa ggctctgcag tccggtcccc ctcagtcccg tcgcaag          1737
```

```
<210> SEQ ID NO 14
<211> LENGTH: 630
<212> TYPE: DNA
<213> ORGANISM: Homo sapiens

<400> SEQUENCE: 14
```

```
atgcaggccg aaggccgggg cacaggggt  tcgacgggcg atgctgatgg cccaggaggc          60
cctggcattc ctgatggccc aggggggcaat gctggcggcc caggagaggc gggtgccacg         120
ggcggcagag gtccccgggg cgcaggggca gcaaggggcct cggggccgag aggaggcgcc         180
ccgcggggtc cgcatggcgg tgccgcttct gcgcaggatg gaaggtgccc ctgcggggcc         240
aggaggccgg acagccgcct gcttgagttg cacatcacga tgcctttctc gtcgcccatg         300
gaagcggagc tggtccgcag gatcctgtcc cgggatgccg caccgctccc ccgaccaggg         360
gcggttctga aggacttcac cgtgtccggc aacctactgt ttatgtcagt tcgggaccag         420
gacagggaag gcgctgggcg gatgagggtg gtgggttggg ggctgggatc cgcctccccg         480
gaggggcaga aagctagaga tctcagaaca cccaaacaca aggtctcaga acagagacct         540
ggtacaccag gcccgccgcc acccgaggga gcccagggag atgggtgcag aggtgtcgcc         600
tttaatgtga tgttctctgc ccctcacatt                                          630
```

```
<210> SEQ ID NO 15
<211> LENGTH: 1227
<212> TYPE: DNA
<213> ORGANISM: Homo sapiens

<400> SEQUENCE: 15
```

```
atgcaggtca ccctgaagac cctccagcag cagaccttca agatagacat tgaccccgag          60
gagacggtga aagcactgaa agagaagatt gaatctgaaa aggggaaaga tgcctttcca         120
gtagcaggtc aaaaattaat ttatgcaggc aaaatcctca atgatgatac tgctctcaaa         180
gaatataaaa ttgatgagaa aaactttgtg gtggttatgg tgaccaaacc caaagcagtg         240
tccacaccag caccagctac aactcagcag tcagctcctg ccagcactac agcagttact         300
tcctccacca ccacaactgt ggctcaggct ccaaccctg  tccctgcctt ggcccccact         360
tccacacctg catccatcac tccagcatca gcgacagcat cttctgaacc tgcacctgct         420
agtgcagcta acaagagaa  gcctgcagaa aagccagcag agacaccagt ggctactagc         480
ccaacagcaa ctgacagtac atcgggtgat tcttctcggt caaacctttt tgaagatgca         540
```

```
acgagtgcac ttgtgacggg tcagtcttac gagaatatgg taactgagat catgtcaatg    600
ggctatgaac gagagcaagt aattgcagcc ctgagagcca gtttcaacaa ccctgacaga    660
gcagtggagt atcttttaat gggaatccct ggagatagag aaagtcaggc tgtggttgac    720 cccctcaag cagctagtac tggggttcct cagtcttcag cagtggctgc agctgcagca    780
actacgacag caacaactac aacaacaagt tctggaggac atcccttga atttttacgg    840 aatcagcctc agtttcaaca gatgagacaa attattcagc agaatccttc cttgcttcca    900
gcgttactac agcagatagg tcgagagaat cctcaattac ttcagcaaat tagccaacac    960
caggagcatt ttattcagat gttaaatgaa ccagttcaag aagctggtgg tcaaggagga   1020
ggaggtggag gtggcagtgg aggaattgca gaagctggaa gtggtcatat gaactacatt   1080
caagtaacac ctcaggaaaa agaagctata gaaaggttaa aggcattagg atttcctgaa   1140
ggacttgtga tacaagcgta ttttgcttgt gagaagaatg agaatttggc tgccaatttt   1200
cttctacagc agaactttga tgaagat                                      1227

<210> SEQ ID NO 16
<211> LENGTH: 624
<212> TYPE: DNA
<213> ORGANISM: Homo sapiens

<400> SEQUENCE: 16
atggacccgt tcctggtgct gctgcactcg gtgtcgtcca gcctgtcgag cagcgagctg     60
accgagctca agttcctatg cctcgggcgc gtgggcaagc gcaagctgga gcgcgtgcag    120
agcggcctag acctcttctc catgctgctg gagcagaacg acctggagcc cgggcacacc    180
gagctcctgc gcgagctgct cgcctccctg cggcgccacg acctgctgcg gcgcgtcgac    240
gacttcgagg cggggcggc ggccggggcc gcgcctgggg aagaagacct gtgtgcagca    300
tttaacgtca tatgtgataa tgtggggaaa gattggagaa ggctggctcg tcagctcaaa    360
gtctcagaca ccaagatcga cagcatcgag gacagatacc cccgcaacct gacagagcgt    420
gtgcgggagt cactgagaat ctggaagaac acagagaagg agaacgcaac agtggcccac    480
ctggtggggg ctctcaggtc ctgccagatg aacctggtgg ctgacctggt acaagaggtt    540
cagcaggccc gtgacctcca gaacaggagt ggggccatgt ccccgatgtc atggaactca    600
gacgcatcta cctccgaagc gtcc                                         624

<210> SEQ ID NO 17
<211> LENGTH: 678
<212> TYPE: DNA
<213> ORGANISM: Homo sapiens

<400> SEQUENCE: 17
atgtcctccc cccgtgactt ccgtgctgag cccgtgaacg actacgaggg caacgactcc     60
gaggctgagg acctgaactt ccgtgaaacc ctgccctcca gctcccaaga gaacaccccc    120
cgttccaagg tgttcgagaa caaggtcaac tccgagaagg tcaagctgtc cctgcgcaac    180
ttcccccaca cgattacga ggacgtgttc gaggaaccct ccgagtccgg ttccgacccc    240
tccatgtgga ccgctcgtgg tcccttccgt cgtgaccgtt ggtcctccga ggacgaggaa    300
gctgctggac cctccaggc tctgtccccc ctgctgtccg acacccgcaa gatcgtgtcc    360
gagggcgagc tggaccagct ggctcagatc cgtcccctga tcttcaactt ccacgagcag    420
accgctatca aggactgcct gaagatcctc gaggaaaaga ccgctgctta cgacatcatg    480
```

-continued

```
caagagttca tggctctcga gctgaagaac ctgcccggcg agttcaactc cggcaaccag          540
ccctccaacc gcgagaagaa ccgttaccgt gacatcctgc ctttccagca ccacggttac          600
tccggtccca acgagcgtac caccttctgg cacggttcca acgagggtgc tgtgtccctg          660
ctgctgcgct actgcgct                                                        678

<210> SEQ ID NO 18
<211> LENGTH: 852
<212> TYPE: DNA
<213> ORGANISM: Homo sapiens

<400> SEQUENCE: 18
atggacgcca tcaagaagaa gatgcagatg ctgaagctcg acaaggagaa cgccttggat           60
cgagctgagc aggcggaggc cgacaagaag gcggcggaag acaggagcaa gcagctggaa          120
gatgagctgg tgtcactgca aaagaaactc aagggcaccg aagatgaact ggacaaatat          180
tctgaggctc tcaaagatgc ccaggagaag ctggagctgg cagagaaaaa ggccaccgat          240
gctgaagccg acgtagcttc tctgaacaga cgcatccagc tggttgagga agagttggat          300
cgtgcccagg agcgtctggc aacagctttg cagaagctgg aggaagctga gaaggcagca          360
gatgagagtg agagaggcat gaaagtcatt gagagtcgag cccaaaaaga tgaagaaaaa          420
atggaaattc aggagatcca actgaaagag gcaaagcaca ttgctgaaga tgccgaccgc          480
aaatatgaag aggtggcccg taagctggtc atcattgaga gcgacctgga acgtgcagag          540
gagcgggctg agctctcaga aggccaagtc cgacagctgg aagaacaatt aagaataatg          600
gatcagacct tgaaagcatt aatggctgca gaggataagt actcgcagaa ggaagacaga          660
tatgaggaag agatcaaggt cctttccgac aagctgaagg aggctgagac tcgggctgag          720
tttgcggaga ggtcagtaac taaattggag aaaagcattg atgacttaga agacgagctg          780
tacgctcaga aactgaagta caaagccatc agcgaggagc tggaccacgc tctcaacgat          840
atgacttcca tg                                                             852

<210> SEQ ID NO 19
<211> LENGTH: 540
<212> TYPE: DNA
<213> ORGANISM: Homo sapiens

<400> SEQUENCE: 19
atgcaggctg agggtcgtgg caccggtggt tccactggcg acgctgacgg tcccggtggt           60
cctggtatcc ccgacggtcc tggtggcaac gctggtggtc aggcgaggc tggtgctacc          120 ggtggtcgtg gtcctcgtgg tgctggtgct gctcgtgctt ccggtccagg tggtggtgct          180
ccccgtggtc ctcacggtgg tgctgcttcc ggcctgaacg gttgctgccg ttgcggtgct          240
cgcggtcccg agtcccgtct gctcgagttc tacctggcta tgcccttcgc taccccctatg          300 gaagctgagc tggctcgtcg ttccctggct caggacgctc ctcctctgcc cgtgcccggt          360
gtcctgctga aggagttcac tgtctccggc aacatcctga ccatccgtct gaccgctgct          420
gaccaccgtc agctccagct gtccatctcc tcatgcctgc agcagctgtc cctgctgatg          480
tggatcaccc agtgtttctt gcccgtgttc ctggctcagc cccctccgg tcaacgtcgt          540

<210> SEQ ID NO 20
<211> LENGTH: 81
<212> TYPE: PRT
<213> ORGANISM: Homo sapiens

<400> SEQUENCE: 20
```

-continued

```
Met Glu Ser Pro Lys Lys Lys Asn Gln Gln Leu Lys Val Gly Ile Leu
1               5                   10                  15

His Leu Gly Ser Arg Gln Lys Lys Ile Arg Ile Gln Leu Arg Ser Gln
            20                  25                  30

Cys Ala Thr Trp Lys Val Ile Cys Lys Ser Cys Ile Ser Gln Thr Pro
        35                  40                  45

Gly Ile Asn Leu Asp Leu Gly Ser Gly Val Lys Val Lys Ile Ile Pro
        50                  55                  60

Lys Glu Glu His Cys Lys Met Pro Glu Ala Gly Glu Glu Gln Pro Gln
65                  70                  75                  80

Val
```

```
<210> SEQ ID NO 21
<211> LENGTH: 400
<212> TYPE: PRT
<213> ORGANISM: Homo sapiens

<400> SEQUENCE: 21
```

```
Met Gly Thr Pro Ala Ser Gly Arg Lys Arg Thr Pro Val Lys Asp Arg
1               5                   10                  15

Phe Ser Ala Glu Asp Glu Ala Leu Ser Asn Ile Ala Arg Glu Ala Glu
            20                  25                  30

Ala Arg Leu Ala Ala Lys Arg Ala Ala Arg Ala Glu Ala Arg Asp Ile
        35                  40                  45

Arg Met Arg Glu Leu Glu Arg Gln Gln Lys Glu Leu Asp Glu Lys Ser
        50                  55                  60

Asp Lys Gln Tyr Ala Glu Asn Tyr Thr Arg Pro Ser Ser Arg Asn Ser
65                  70                  75                  80

Ala Ser Ala Thr Thr Pro Leu Ser Gly Asn Ser Ser Arg Arg Gly Ser
            85                  90                  95

Gly Asp Thr Ser Ser Leu Ile Asp Pro Asp Thr Ser Leu Ser Glu Leu
            100                 105                 110

Arg Glu Ser Leu Ser Glu Val Glu Glu Lys Tyr Lys Lys Ala Met Val
            115                 120                 125

Ser Asn Ala Gln Leu Asp Asn Glu Lys Asn Asn Leu Ile Tyr Gln Val
        130                 135                 140

Asp Thr Leu Lys Asp Val Ile Glu Glu Gln Glu Glu Gln Met Ala Glu
145                 150                 155                 160

Phe Tyr Arg Glu Asn Glu Glu Lys Ser Lys Glu Leu Glu Arg Gln Lys
            165                 170                 175

His Met Cys Ser Val Leu Gln His Lys Met Glu Glu Leu Lys Glu Gly
            180                 185                 190

Leu Arg Gln Arg Asp Glu Leu Ile Glu Lys His Gly Leu Val Ile Ile
            195                 200                 205

Pro Asp Gly Thr Pro Asn Gly Asp Val Ser His Glu Pro Val Ala Gly
        210                 215                 220

Ala Ile Thr Val Val Ser Gln Glu Ala Ala Gln Val Leu Glu Ser Ala
225                 230                 235                 240

Gly Glu Gly Pro Leu Asp Val Arg Leu Arg Lys Leu Ala Gly Glu Lys
            245                 250                 255

Glu Glu Leu Leu Ser Gln Ile Arg Lys Leu Lys Leu Gln Leu Glu Glu
            260                 265                 270

Glu Arg Gln Lys Cys Ser Arg Asn Asp Gly Thr Val Gly Asp Leu Ala
            275                 280                 285
```

-continued

```
Gly Leu Gln Asn Gly Ser Asp Leu Gln Phe Ile Glu Met Gln Arg Asp
    290             295             300

Ala Asn Arg Gln Ile Ser Glu Tyr Lys Phe Lys Leu Ser Lys Ala Glu
305             310             315             320

Gln Asp Ile Thr Thr Leu Glu Gln Ser Ile Ser Arg Leu Glu Gly Gln
                325             330             335

Val Leu Arg Tyr Lys Thr Ala Ala Glu Asn Ala Glu Lys Val Glu Asp
            340             345             350

Glu Leu Lys Ala Glu Lys Arg Lys Leu Gln Arg Glu Leu Arg Thr Ala
        355             360             365

Leu Asp Lys Ile Glu Glu Met Glu Met Thr Asn Ser His Leu Ala Lys
    370             375             380

Arg Leu Glu Lys Met Lys Ala Asn Arg Thr Ala Leu Leu Ala Gln Gln
385             390             395             400
```

<210> SEQ ID NO 22
<211> LENGTH: 116
<212> TYPE: PRT
<213> ORGANISM: Homo sapiens

<400> SEQUENCE: 22

```
Met Ser Trp Arg Gly Arg Ser Thr Tyr Arg Pro Arg Pro Arg Arg Tyr
1               5               10              15

Val Glu Pro Pro Glu Met Ile Gly Pro Met Arg Pro Glu Gln Phe Ser
            20              25              30

Asp Glu Val Glu Pro Ala Thr Pro Glu Glu Gly Glu Pro Ala Thr Gln
        35              40              45

Arg Gln Asp Pro Ala Ala Ala Gln Glu Gly Glu Asp Glu Gly Ala Ser
    50              55              60

Ala Gly Gln Gly Pro Lys Pro Glu Ala His Ser Gln Glu Gln Gly His
65              70              75              80

Pro Gln Thr Gly Cys Glu Cys Glu Asp Gly Pro Asp Gly Gln Glu Met
                85              90              95

Asp Pro Pro Asn Pro Glu Glu Val Lys Thr Pro Glu Glu Gly Glu Lys
            100             105             110

Gln Ser Gln Cys
        115
```

<210> SEQ ID NO 23
<211> LENGTH: 631
<212> TYPE: PRT
<213> ORGANISM: Homo sapiens

<400> SEQUENCE: 23

```
Met Ser His Trp Ala Pro Glu Trp Lys Arg Ala Glu Ala Asn Pro Arg
1               5               10              15

Asp Leu Gly Ala Ser Trp Asp Val Arg Gly Ser Arg Gly Ser Gly Trp
            20              25              30

Ser Gly Pro Phe Gly His Gln Gly Pro Arg Ala Ala Gly Ser Arg Glu
        35              40              45

Pro Pro Leu Cys Phe Lys Ile Lys Asn Asn Met Val Gly Val Val Ile
    50              55              60

Gly Tyr Ser Gly Ser Lys Ile Lys Asp Leu Gln His Ser Thr Asn Thr
65              70              75              80

Lys Ile Gln Ile Ile Asn Gly Glu Ser Glu Ala Lys Val Arg Ile Phe
                85              90              95
```

-continued

```
Gly Asn Arg Glu Met Lys Ala Lys Ala Lys Ala Ala Ile Glu Thr Leu
            100             105             110

Ile Arg Lys Gln Glu Ser Tyr Asn Ser Glu Ser Ser Val Asp Asn Ala
            115             120             125

Ala Ser Gln Thr Pro Ile Gly Arg Asn Leu Gly Arg Asn Asp Ile Val
        130             135             140

Gly Glu Ala Glu Pro Leu Ser Asn Trp Asp Arg Ile Arg Ala Ala Val
145             150             155             160

Val Glu Cys Glu Lys Arg Lys Trp Ala Asp Leu Pro Pro Val Lys Lys
                165             170             175

Asn Phe Tyr Ile Glu Ser Lys Ala Thr Ser Cys Met Ser Glu Met Gln
            180             185             190

Val Ile Asn Trp Arg Lys Glu Asn Phe Asn Ile Thr Cys Asp Asp Leu
            195             200             205

Lys Ser Gly Glu Lys Arg Leu Ile Pro Lys Pro Thr Cys Arg Phe Lys
        210             215             220

Asp Ala Phe Gln Gln Tyr Pro Asp Leu Leu Lys Ser Ile Ile Arg Val
225             230             235             240

Gly Ile Val Lys Pro Thr Pro Ile Gln Ser Gln Ala Trp Pro Ile Ile
                245             250             255

Leu Gln Gly Ile Asp Leu Ile Val Val Ala Gln Thr Gly Thr Gly Lys
            260             265             270

Thr Leu Ser Tyr Leu Met Pro Gly Phe Ile His Leu Asp Ser Gln Pro
        275             280             285

Ile Ser Arg Glu Gln Arg Asn Gly Pro Gly Met Leu Val Leu Thr Pro
290             295             300

Thr Arg Glu Leu Ala Leu His Val Glu Ala Glu Cys Ser Lys Tyr Ser
305             310             315             320

Tyr Lys Gly Leu Lys Ser Ile Cys Ile Tyr Gly Gly Arg Asn Arg Asn
            325             330             335

Gly Gln Ile Glu Asp Ile Ser Lys Gly Val Asp Ile Ile Ala Thr
            340             345             350

Pro Gly Arg Leu Asn Asp Leu Gln Met Asn Asn Ser Val Asn Leu Arg
        355             360             365

Ser Ile Thr Tyr Leu Val Ile Asp Glu Ala Asp Lys Met Leu Asp Met
    370             375             380

Glu Phe Glu Pro Gln Ile Arg Lys Ile Leu Leu Asp Val Arg Pro Asp
385             390             395             400

Arg Gln Thr Val Met Thr Ser Ala Thr Trp Pro Asp Thr Val Arg Gln
                405             410             415

Leu Ala Leu Ser Tyr Leu Lys Asp Pro Met Ile Val Tyr Val Gly Asn
            420             425             430

Leu Asn Leu Val Ala Val Asn Thr Val Lys Gln Asn Ile Ile Val Thr
        435             440             445

Thr Glu Lys Glu Lys Arg Ala Leu Thr Gln Glu Phe Val Glu Asn Met
    450             455             460

Ser Pro Asn Asp Lys Val Ile Met Phe Val Ser Gln Lys His Ile Ala
465             470             475             480

Asp Asp Leu Ser Ser Asp Phe Asn Ile Gln Gly Ile Ser Ala Glu Ser
            485             490             495

Leu His Gly Asn Ser Glu Gln Ser Asp Gln Glu Arg Ala Val Glu Asp
        500             505             510
```

-continued

```
Phe Lys Ser Gly Asn Ile Lys Ile Leu Ile Thr Thr Asp Ile Val Ser
        515                 520                 525

Arg Gly Leu Asp Leu Asn Asp Val Thr His Val Tyr Asn Tyr Asp Phe
    530                 535                 540

Pro Arg Asn Ile Asp Val Tyr Val His Arg Val Gly Tyr Ile Gly Arg
545                 550                 555                 560

Thr Gly Lys Thr Gly Thr Ser Val Thr Leu Ile Thr Gln Arg Asp Ser
                565                 570                 575

Lys Met Ala Gly Glu Leu Ile Lys Ile Leu Asp Arg Ala Asn Gln Ser
                580                 585                 590

Val Pro Glu Asp Leu Val Val Met Ala Glu Gln Tyr Lys Leu Asn Gln
                595                 600                 605

Gln Lys Arg His Arg Glu Thr Arg Ser Arg Lys Pro Gly Gln Arg Arg
        610                 615                 620

Lys Glu Phe Tyr Phe Leu Ser
625                 630

<210> SEQ ID NO 24
<211> LENGTH: 648
<212> TYPE: PRT
<213> ORGANISM: Homo sapiens

<400> SEQUENCE: 24

Met Ser His His Gly Gly Ala Pro Lys Ala Ser Thr Trp Val Val Ala
1               5                   10                  15

Ser Arg Arg Ser Ser Thr Val Ser Arg Ala Pro Glu Arg Arg Pro Ala
                20                  25                  30

Glu Glu Leu Asn Arg Thr Gly Pro Glu Gly Tyr Ser Val Gly Arg Gly
            35                  40                  45

Gly Arg Trp Arg Gly Thr Ser Arg Pro Pro Glu Ala Val Ala Ala Gly
    50                  55                  60

His Glu Glu Leu Pro Leu Cys Phe Ala Leu Lys Ser His Phe Val Gly
65                  70                  75                  80

Ala Val Ile Gly Arg Gly Gly Ser Lys Ile Lys Asn Ile Gln Ser Thr
                85                  90                  95

Thr Asn Thr Thr Ile Gln Ile Ile Gln Glu Gln Pro Glu Ser Leu Val
            100                 105                 110

Lys Ile Phe Gly Ser Lys Ala Met Gln Thr Lys Ala Lys Ala Val Ile
        115                 120                 125

Asp Asn Phe Val Lys Lys Leu Glu Glu Asn Tyr Asn Ser Glu Cys Gly
        130                 135                 140

Ile Asp Thr Ala Phe Gln Pro Ser Val Gly Lys Asp Gly Ser Thr Asp
145                 150                 155                 160

Asn Asn Val Val Ala Gly Asp Arg Pro Leu Ile Asp Trp Asp Gln Ile
                165                 170                 175

Arg Glu Glu Gly Leu Lys Trp Gln Lys Thr Lys Trp Ala Asp Leu Pro
            180                 185                 190

Pro Ile Lys Lys Asn Phe Tyr Lys Glu Ser Thr Ala Thr Ser Ala Met
        195                 200                 205

Ser Lys Val Glu Ala Asp Ser Trp Arg Lys Glu Asn Phe Asn Ile Thr
        210                 215                 220

Trp Asp Asp Leu Lys Asp Gly Glu Lys Arg Pro Ile Pro Asn Pro Thr
225                 230                 235                 240

Cys Thr Phe Asp Asp Ala Phe Gln Cys Tyr Pro Glu Val Met Glu Asn
                245                 250                 255
```

```
Ile Lys Lys Ala Gly Phe Gln Lys Pro Thr Pro Ile Gln Ser Gln Ala
        260                 265             270

Trp Pro Ile Val Leu Gln Gly Ile Asp Leu Ile Gly Val Ala Gln Thr
        275                 280             285

Gly Thr Gly Lys Thr Leu Cys Tyr Leu Met Pro Gly Phe Ile His Leu
        290                 295             300

Val Leu Gln Pro Ser Leu Lys Gly Gln Arg Asn Arg Pro Gly Met Leu
305                 310             315                 320

Val Leu Thr Pro Thr Arg Glu Leu Ala Leu Gln Val Glu Gly Glu Cys
                325             330             335

Cys Lys Tyr Ser Tyr Lys Gly Leu Arg Ser Val Cys Val Tyr Gly Gly
        340                 345             350

Gly Asn Arg Asp Glu Gln Ile Glu Glu Leu Lys Lys Gly Val Asp Ile
        355                 360             365

Ile Ile Ala Thr Pro Gly Arg Leu Asn Asp Leu Gln Met Ser Asn Phe
        370                 375             380

Val Asn Leu Lys Asn Ile Thr Tyr Leu Val Leu Asp Glu Ala Asp Lys
385                 390             395                 400

Met Leu Asp Met Gly Phe Glu Pro Gln Ile Met Lys Ile Leu Leu Asp
                405             410             415

Val Arg Pro Asp Arg Gln Thr Val Met Thr Ser Ala Thr Trp Pro His
                420             425             430

Ser Val His Arg Leu Ala Gln Ser Tyr Leu Lys Glu Pro Met Ile Val
        435                 440             445

Tyr Val Gly Thr Leu Asp Leu Val Ala Val Ser Ser Val Lys Gln Asn
        450                 455             460

Ile Ile Val Thr Thr Glu Glu Glu Lys Trp Ser His Met Gln Thr Phe
465                 470             475                 480

Leu Gln Ser Met Ser Ser Thr Asp Lys Val Ile Val Phe Val Ser Arg
                485             490             495

Lys Ala Val Ala Asp His Leu Ser Ser Asp Leu Ile Leu Gly Asn Ile
        500                 505             510

Ser Val Glu Ser Leu His Gly Asp Arg Glu Gln Arg Asp Arg Glu Lys
        515                 520             525

Ala Leu Glu Asn Phe Lys Thr Gly Lys Val Arg Ile Leu Ile Ala Thr
        530                 535             540

Asp Leu Ala Ser Arg Gly Leu Asp Val His Asp Val Thr His Val Tyr
545                 550             555                 560

Asn Phe Asp Phe Pro Arg Asn Ile Glu Glu Tyr Val His Arg Ile Gly
                565             570             575

Arg Thr Gly Arg Ala Gly Arg Thr Gly Val Ser Ile Thr Thr Leu Thr
        580                 585             590

Arg Asn Asp Trp Arg Val Ala Ser Glu Leu Ile Asn Ile Leu Glu Arg
        595                 600             605

Ala Asn Gln Ser Ile Pro Glu Glu Leu Val Ser Met Ala Glu Arg Phe
        610                 615             620

Lys Ala His Gln Gln Lys Arg Glu Met Glu Arg Lys Met Glu Arg Pro
625                 630             635                 640

Gln Gly Arg Pro Lys Lys Phe His
                645
```

```
<210> SEQ ID NO 25
<211> LENGTH: 139
```

<212> TYPE: PRT
<213> ORGANISM: Homo sapiens

<400> SEQUENCE: 25

Met Ser Trp Arg Gly Arg Ser Thr Tyr Tyr Trp Pro Arg Pro Arg Arg
1               5                   10                  15

Tyr Val Gln Pro Pro Glu Met Ile Gly Pro Met Arg Pro Glu Gln Phe
                20                  25                  30

Ser Asp Glu Val Glu Pro Ala Thr Pro Glu Glu Gly Glu Pro Ala Thr
            35                  40                  45

Gln Arg Gln Asp Pro Ala Ala Ala Gln Glu Gly Glu Asp Glu Gly Ala
        50                  55                  60

Ser Ala Gly Gln Gly Pro Lys Pro Glu Ala Asp Ser Gln Glu Gln Gly
65                  70                  75                  80

His Pro Gln Thr Gly Cys Glu Cys Glu Asp Gly Pro Asp Gly Gln Glu
                85                  90                  95

Met Asp Pro Pro Asn Pro Glu Glu Val Lys Thr Pro Glu Glu Glu Met
            100                 105                 110

Arg Ser His Tyr Val Ala Gln Thr Gly Ile Leu Trp Leu Leu Met Asn
        115                 120                 125

Asn Cys Phe Leu Asn Leu Ser Pro Arg Lys Pro
        130                 135

<210> SEQ ID NO 26
<211> LENGTH: 369
<212> TYPE: PRT
<213> ORGANISM: Homo sapiens

<400> SEQUENCE: 26

Met Pro Arg Ala Pro Lys Arg Gln Arg Cys Met Pro Glu Glu Asp Leu
1               5                   10                  15

Gln Ser Gln Ser Glu Thr Gln Gly Leu Glu Gly Ala Gln Ala Pro Leu
                20                  25                  30

Ala Val Glu Glu Asp Ala Ser Ser Ser Thr Ser Thr Ser Ser Ser Phe
            35                  40                  45

Pro Ser Ser Phe Pro Ser Ser Ser Ser Ser Ser Ser Ser Cys Tyr
        50                  55                  60

Pro Leu Ile Pro Ser Thr Pro Glu Glu Val Ser Ala Asp Asp Glu Thr
65                  70                  75                  80

Pro Asn Pro Pro Gln Ser Ala Gln Ile Ala Cys Ser Ser Pro Ser Val
                85                  90                  95

Val Ala Ser Leu Pro Leu Asp Gln Ser Asp Glu Gly Ser Ser Ser Gln
            100                 105                 110

Lys Glu Glu Ser Pro Ser Thr Leu Gln Val Leu Pro Asp Ser Glu Ser
        115                 120                 125

Leu Pro Arg Ser Glu Ile Asp Glu Lys Val Thr Asp Leu Val Gln Phe
        130                 135                 140

Leu Leu Phe Lys Tyr Gln Met Lys Glu Pro Ile Thr Lys Ala Glu Ile
145                 150                 155                 160

Leu Glu Ser Val Ile Arg Asn Tyr Glu Asp His Phe Pro Leu Leu Phe
                165                 170                 175

Ser Glu Ala Ser Glu Cys Met Leu Leu Val Phe Gly Ile Asp Val Lys
            180                 185                 190

Glu Val Asp Pro Thr Gly His Ser Phe Val Leu Val Thr Ser Leu Gly
        195                 200                 205

-continued

```
Leu Thr Tyr Asp Gly Met Leu Ser Asp Val Gln Ser Met Pro Lys Thr
    210             215                 220

Gly Ile Leu Ile Leu Ile Leu Ser Ile Val Phe Ile Glu Gly Tyr Cys
225             230                 235                 240

Thr Pro Glu Glu Val Ile Trp Glu Ala Leu Asn Met Met Gly Leu Tyr
            245                 250                 255

Asp Gly Met Glu His Leu Ile Tyr Gly Glu Pro Arg Lys Leu Leu Thr
            260                 265                 270

Gln Asp Trp Val Gln Glu Asn Tyr Leu Glu Tyr Arg Gln Val Pro Gly
            275                 280                 285

Ser Asp Pro Ala Arg Tyr Glu Phe Leu Trp Gly Pro Arg Ala His Ala
    290                 295                 300

Glu Ile Arg Lys Met Ser Leu Leu Lys Phe Leu Ala Lys Val Asn Gly
305             310                 315                 320

Ser Asp Pro Arg Ser Phe Pro Leu Trp Tyr Glu Glu Ala Leu Lys Asp
            325                 330                 335

Glu Glu Glu Arg Ala Gln Asp Arg Ile Ala Thr Thr Asp Asp Thr Thr
            340                 345                 350

Ala Met Ala Ser Ala Ser Ser Ser Ala Thr Gly Ser Phe Ser Tyr Pro
            355                 360                 365

Glu
```

```
<210> SEQ ID NO 27
<211> LENGTH: 126
<212> TYPE: PRT
<213> ORGANISM: Homo sapiens

<400> SEQUENCE: 27

Met Ser Val Met Asp Leu Ala Asn Thr Cys Ser Ser Phe Gln Ser Asp
1               5                   10                  15

Leu Asp Phe Cys Ser Asp Cys Gly Ser Val Leu Pro Leu Pro Gly Ala
            20                  25                  30

Gln Asp Thr Val Thr Cys Ile Arg Cys Gly Phe Asn Ile Asn Val Arg
        35                  40                  45

Asp Phe Glu Gly Lys Val Val Lys Thr Ser Val Val Phe His Gln Leu
    50                  55                  60

Gly Thr Ala Met Pro Met Ser Val Glu Glu Gly Pro Glu Cys Gln Gly
65              70                  75                  80

Pro Val Val Asp Arg Arg Cys Pro Arg Cys Gly His Glu Gly Met Ala
                85                  90                  95

Tyr His Thr Arg Gln Met Arg Ser Ala Asp Glu Gly Gln Thr Val Phe
            100                 105                 110

Tyr Thr Cys Thr Asn Cys Lys Phe Gln Glu Lys Glu Asp Ser
        115                 120                 125
```

```
<210> SEQ ID NO 28
<211> LENGTH: 448
<212> TYPE: PRT
<213> ORGANISM: Homo sapiens

<400> SEQUENCE: 28

Met Leu Trp Leu Ala Leu Gly Pro Phe Pro Ala Met Glu Asn Gln Val
1               5                   10                  15

Leu Val Ile Arg Ile Lys Ile Pro Asn Ser Gly Ala Val Asp Trp Thr
            20                  25                  30

Val His Ser Gly Pro Gln Leu Leu Phe Arg Asp Val Leu Asp Val Ile
```

-continued

```
              35                   40                   45

Gly Gln Val Leu Pro Glu Ala Thr Thr Thr Ala Phe Glu Tyr Glu Asp
    50                   55                   60

Glu Asp Gly Asp Arg Ile Thr Val Arg Ser Asp Glu Glu Met Lys Ala
65                   70                   75                   80

Met Leu Ser Tyr Tyr Tyr Ser Thr Val Met Glu Gln Gln Val Asn Gly
                85                   90                   95

Gln Leu Ile Glu Pro Leu Gln Ile Phe Pro Arg Ala Cys Lys Pro Pro
            100                  105                  110

Gly Glu Arg Asn Ile His Gly Leu Lys Val Asn Thr Arg Ala Gly Pro
            115                  120                  125

Ser Gln His Ser Ser Pro Ala Val Ser Asp Ser Leu Pro Ser Asn Ser
    130                  135                  140

Leu Lys Lys Ser Ser Ala Glu Leu Lys Lys Ile Leu Ala Asn Gly Gln
145                  150                  155                  160

Met Asn Glu Gln Asp Ile Arg Tyr Arg Asp Thr Leu Gly His Gly Asn
                165                  170                  175

Gly Gly Thr Val Tyr Lys Ala Tyr His Val Pro Ser Gly Lys Ile Leu
            180                  185                  190

Ala Val Lys Val Ile Leu Leu Asp Ile Thr Leu Glu Leu Gln Lys Gln
            195                  200                  205

Ile Met Ser Glu Leu Glu Ile Leu Tyr Lys Cys Asp Ser Ser Tyr Ile
    210                  215                  220

Ile Gly Phe Tyr Gly Ala Phe Phe Val Glu Asn Arg Ile Ser Ile Cys
225                  230                  235                  240

Thr Glu Phe Met Asp Gly Gly Ser Leu Asp Val Tyr Arg Lys Met Pro
                245                  250                  255

Glu His Val Leu Gly Arg Ile Ala Val Ala Val Val Lys Gly Leu Thr
            260                  265                  270

Tyr Leu Trp Ser Leu Lys Ile Leu His Arg Asp Val Lys Pro Ser Asn
    275                  280                  285

Met Leu Val Asn Thr Arg Gly Gln Val Lys Leu Cys Asp Phe Gly Val
    290                  295                  300

Ser Thr Gln Leu Val Asn Ser Ile Ala Lys Thr Tyr Val Gly Thr Asn
305                  310                  315                  320

Ala Tyr Met Ala Pro Glu Arg Ile Ser Gly Glu Gln Tyr Gly Ile His
                325                  330                  335

Ser Asp Val Trp Ser Leu Gly Ile Ser Phe Met Glu Leu Ala Leu Gly
                340                  345                  350

Arg Phe Pro Tyr Pro Gln Ile Gln Lys Asn Gln Gly Ser Leu Met Pro
            355                  360                  365

Leu Gln Leu Leu Gln Cys Ile Val Asp Glu Asp Ser Pro Val Leu Pro
    370                  375                  380

Val Gly Glu Phe Ser Glu Pro Phe Val His Phe Ile Thr Gln Cys Met
385                  390                  395                  400

Arg Lys Gln Pro Lys Glu Arg Pro Ala Pro Glu Glu Leu Met Gly His
                405                  410                  415

Pro Phe Ile Val Gln Phe Asn Asp Gly Asn Ala Ala Val Val Ser Met
                420                  425                  430

Trp Val Cys Arg Ala Leu Glu Glu Arg Arg Ser Gln Gln Gly Pro Pro
            435                  440                  445
```

<210> SEQ ID NO 29

```
<211> LENGTH: 317
<212> TYPE: PRT
<213> ORGANISM: Homo sapiens

<400> SEQUENCE: 29

Met Ser Ser Glu Gln Lys Ser Gln His Cys Lys Pro Glu Glu Gly Val
1               5                   10                  15

Glu Ala Gln Glu Glu Ala Leu Gly Leu Val Gly Ala Gln Ala Pro Thr
            20                  25                  30

Thr Glu Glu Gln Glu Ala Ala Val Ser Ser Ser Ser Pro Leu Val Pro
        35                  40                  45

Gly Thr Leu Glu Glu Val Pro Ala Ala Glu Ser Ala Gly Pro Pro Gln
    50                  55                  60

Ser Pro Gln Gly Ala Ser Ala Leu Pro Thr Thr Ile Ser Phe Thr Cys
65                  70                  75                  80

Trp Arg Gln Pro Asn Glu Gly Ser Ser Ser Gln Glu Glu Glu Gly Pro
                85                  90                  95

Ser Thr Ser Pro Asp Ala Glu Ser Leu Phe Arg Glu Ala Leu Ser Asn
            100                 105                 110

Lys Val Asp Glu Leu Ala His Phe Leu Leu Arg Lys Tyr Arg Ala Lys
            115                 120                 125

Glu Leu Val Thr Lys Ala Glu Met Leu Glu Arg Val Ile Lys Asn Tyr
        130                 135                 140

Lys Arg Cys Phe Pro Val Ile Phe Gly Lys Ala Ser Glu Ser Leu Lys
145                 150                 155                 160

Met Ile Phe Gly Ile Asp Val Lys Glu Val Asp Pro Ala Ser Asn Thr
                165                 170                 175

Tyr Thr Leu Val Thr Cys Leu Gly Leu Ser Tyr Asp Gly Leu Leu Gly
            180                 185                 190

Asn Asn Gln Ile Phe Pro Lys Thr Gly Leu Leu Ile Ile Val Leu Gly
            195                 200                 205

Thr Ile Ala Met Glu Gly Asp Ser Ala Ser Glu Glu Glu Ile Trp Glu
        210                 215                 220

Glu Leu Gly Val Met Gly Val Tyr Asp Gly Arg Glu His Thr Val Tyr
225                 230                 235                 240

Gly Glu Pro Arg Lys Leu Leu Thr Gln Asp Trp Val Gln Glu Asn Tyr
                245                 250                 255

Leu Glu Tyr Arg Gln Val Pro Gly Ser Asn Pro Ala Arg Tyr Glu Phe
            260                 265                 270

Leu Trp Gly Pro Arg Ala Leu Ala Glu Thr Ser Tyr Val Lys Val Leu
        275                 280                 285

Glu His Val Val Arg Val Asn Ala Arg Val Arg Ile Ala Tyr Pro Ser
    290                 295                 300

Leu Arg Glu Ala Ala Leu Leu Glu Glu Glu Glu Gly Val
305                 310                 315

<210> SEQ ID NO 30
<211> LENGTH: 712
<212> TYPE: PRT
<213> ORGANISM: Homo sapiens

<400> SEQUENCE: 30

Met Ser Gln Trp Tyr Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30
```

-continued

```
Tyr Leu Ala Gln Trp Leu Glu Lys Gln Asp Trp Glu His Ala Ala Asn
        35              40              45

Asp Val Ser Phe Ala Thr Ile Arg Phe His Asp Leu Leu Ser Gln Leu
        50              55              60

Asp Asp Gln Tyr Ser Arg Phe Ser Leu Glu Asn Asn Phe Leu Leu Gln
65              70              75              80

His Asn Ile Arg Lys Ser Lys Arg Asn Leu Gln Asp Asn Phe Gln Glu
            85              90              95

Asp Pro Ile Gln Met Ser Met Ile Ile Tyr Ser Cys Leu Lys Glu Glu
            100             105             110

Arg Lys Ile Leu Glu Asn Ala Gln Arg Phe Asn Gln Ala Gln Ser Gly
            115             120             125

Asn Ile Gln Ser Thr Val Met Leu Asp Lys Gln Lys Glu Leu Asp Ser
        130             135             140

Lys Val Arg Asn Val Lys Asp Lys Val Met Cys Ile Glu His Glu Ile
145             150             155             160

Lys Ser Leu Glu Asp Leu Gln Asp Glu Tyr Asp Phe Lys Cys Lys Thr
            165             170             175

Leu Gln Asn Arg Glu His Glu Thr Asn Gly Val Ala Lys Ser Asp Gln
            180             185             190

Lys Gln Glu Gln Leu Leu Leu Lys Lys Met Tyr Leu Met Leu Asp Asn
            195             200             205

Lys Arg Lys Glu Val Val His Lys Ile Ile Glu Leu Leu Asn Val Thr
        210             215             220

Glu Leu Thr Gln Asn Ala Leu Ile Asn Asp Glu Leu Val Glu Trp Lys
225             230             235             240

Arg Arg Gln Gln Ser Ala Cys Ile Gly Gly Pro Pro Asn Ala Cys Leu
            245             250             255

Asp Gln Leu Gln Asn Trp Phe Thr Ile Val Ala Glu Ser Leu Gln Gln
            260             265             270

Val Arg Gln Gln Leu Lys Lys Leu Glu Glu Leu Glu Gln Lys Tyr Thr
        275             280             285

Tyr Glu His Asp Pro Ile Thr Lys Asn Lys Gln Val Leu Trp Asp Arg
        290             295             300

Thr Phe Ser Leu Phe Gln Gln Leu Ile Gln Ser Ser Phe Val Val Glu
305             310             315             320

Arg Gln Pro Cys Met Pro Thr His Pro Gln Arg Pro Leu Val Leu Lys
            325             330             335

Thr Gly Val Gln Phe Thr Val Lys Leu Arg Leu Leu Val Lys Leu Gln
            340             345             350

Glu Leu Asn Tyr Asn Leu Lys Val Lys Val Leu Phe Asp Lys Asp Val
            355             360             365

Asn Glu Arg Asn Thr Val Lys Gly Phe Arg Lys Phe Asn Ile Leu Gly
        370             375             380

Thr His Thr Lys Val Met Asn Met Glu Glu Ser Thr Asn Gly Ser Leu
385             390             395             400

Ala Ala Glu Phe Arg His Leu Gln Leu Lys Glu Gln Lys Asn Ala Gly
            405             410             415

Thr Arg Thr Asn Glu Gly Pro Leu Ile Val Thr Glu Glu Leu His Ser
            420             425             430

Leu Ser Phe Glu Thr Gln Leu Cys Gln Pro Gly Leu Val Ile Asp Leu
            435             440             445
```

```
Glu Thr Thr Ser Leu Pro Val Val Val Ile Ser Asn Val Ser Gln Leu
    450                 455                 460

Pro Ser Gly Trp Ala Ser Ile Leu Trp Tyr Asn Met Leu Val Ala Glu
465                 470                 475                 480

Pro Arg Asn Leu Ser Phe Phe Leu Thr Pro Pro Cys Ala Arg Trp Ala
                485                 490                 495

Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
    530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
    610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
    675                 680                 685

Glu Pro Met Glu Leu Asp Gly Pro Lys Gly Thr Gly Tyr Ile Lys Thr
    690                 695                 700

Glu Leu Ile Ser Val Ser Glu Val
705                 710
```

```
<210> SEQ ID NO 31
<211> LENGTH: 288
<212> TYPE: PRT
<213> ORGANISM: Homo sapiens

<400> SEQUENCE: 31

Met Ser Ala Thr Gly Asp Arg His Pro Thr Gln Gly Asp Gln Glu Ala
1               5                   10                  15

Pro Val Ser Gln Glu Gly Ala Gln Ala Glu Ala Ala Gly Ala Gly Asn
            20                  25                  30

Gln Glu Gly Gly Asp Ser Gly Pro Asp Ser Ser Asp Val Val Pro Ala
        35                  40                  45

Ala Glu Val Val Gly Val Ala Gly Pro Val Glu Gly Leu Gly Glu Glu
    50                  55                  60

Glu Gly Glu Gln Ala Ala Gly Leu Ala Ala Val Pro Arg Gly Gly Ser
65                  70                  75                  80

Ala Glu Glu Asp Ser Asp Ile Gly Pro Ala Thr Glu Glu Glu Glu
            85                  90                  95

Glu Glu Gly Asn Glu Ala Ala Asn Phe Asp Leu Ala Val Val Ala Arg
            100                 105                 110
```

```
Arg Tyr Pro Ala Ser Gly Ile His Phe Val Leu Leu Asp Met Val His
        115             120             125

Ser Leu Leu His Arg Leu Ser His Asn Asp His Ile Leu Ile Glu Asn
    130             135             140

Arg Gln Leu Ser Arg Leu Met Val Gly Pro His Ala Ala Ala Arg Asn
145             150             155             160

Leu Trp Gly Asn Leu Pro Pro Leu Leu Leu Pro Gln Arg Leu Gly Ala
            165             170             175

Gly Ala Ala Ala Arg Ala Gly Glu Gly Leu Gly Leu Ile Gln Glu Ala
            180             185             190

Ala Ser Val Pro Glu Pro Ala Val Pro Ala Asp Leu Ala Glu Met Ala
            195             200             205

Arg Glu Pro Ala Glu Glu Ala Ala Glu Glu Lys Leu Ser Glu Glu Ala
    210             215             220

Thr Glu Glu Pro Asp Ala Glu Glu Pro Ala Thr Glu Glu Pro Thr Ala
225             230             235             240

Gln Glu Ala Thr Ala Pro Glu Glu Val Thr Lys Ser Gln Pro Glu Lys
            245             250             255

Trp Asp Glu Glu Ala Gln Asp Ala Ala Gly Glu Glu Gly Lys Glu Gln
            260             265             270

Glu Lys Glu Lys Asp Ala Glu Asn Lys Val Lys Asn Ser Lys Gly Thr
            275             280             285

<210> SEQ ID NO 32
<211> LENGTH: 579
<212> TYPE: PRT
<213> ORGANISM: Homo sapiens

<400> SEQUENCE: 32

Met Asn Lys Leu Tyr Ile Gly Asn Leu Ser Glu Asn Ala Ala Pro Ser
1               5               10              15

Asp Leu Glu Ser Ile Phe Lys Asp Ala Lys Ile Pro Val Ser Gly Pro
            20              25              30

Phe Leu Val Lys Thr Gly Tyr Ala Phe Val Asp Cys Pro Asp Glu Ser
        35              40              45

Trp Ala Leu Lys Ala Ile Glu Ala Leu Ser Gly Lys Ile Glu Leu His
    50              55              60

Gly Lys Pro Ile Glu Val Glu His Ser Val Pro Lys Arg Gln Arg Ile
65              70              75              80

Arg Lys Leu Gln Ile Arg Asn Ile Pro Pro His Leu Gln Trp Glu Val
            85              90              95

Leu Asp Ser Leu Leu Val Gln Tyr Gly Val Val Glu Ser Cys Glu Gln
            100             105             110

Val Asn Thr Asp Ser Glu Thr Ala Val Val Asn Val Thr Tyr Ser Ser
    115             120             125

Lys Asp Gln Ala Arg Gln Ala Leu Asp Lys Leu Asn Gly Phe Gln Leu
    130             135             140

Glu Asn Phe Thr Leu Lys Val Ala Tyr Ile Pro Asp Glu Met Ala Ala
145             150             155             160

Gln Gln Asn Pro Leu Gln Gln Pro Arg Gly Arg Arg Gly Leu Gly Gln
            165             170             175

Arg Gly Ser Ser Arg Gln Gly Ser Pro Gly Ser Val Ser Lys Gln Lys
            180             185             190

Pro Cys Asp Leu Pro Leu Arg Leu Leu Val Pro Thr Gln Phe Val Gly
```

-continued

```
               195                 200                 205
Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
                245                 250                 255

Cys Lys Ser Ile Leu Glu Ile Met His Lys Glu Ala Gln Asp Ile Lys
                260                 265                 270

Phe Thr Glu Glu Ile Pro Leu Lys Ile Leu Ala His Asn Asn Phe Val
                275                 280                 285

Gly Arg Leu Ile Gly Lys Glu Gly Arg Asn Leu Lys Lys Ile Glu Gln
    290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
                325                 330                 335

Ala Lys Ala Glu Glu Glu Ile Met Lys Lys Ile Arg Glu Ser Tyr Glu
                340                 345                 350

Asn Asp Ile Ala Ser Met Asn Leu Gln Ala His Leu Ile Pro Gly Leu
                355                 360                 365

Asn Leu Asn Ala Leu Gly Leu Phe Pro Pro Thr Ser Gly Met Pro Pro
    370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Leu Phe Ile Pro Ala Leu Ser
                405                 410                 415

Val Gly Ala Ile Ile Gly Lys Gln Gly Gln His Ile Lys Gln Leu Ser
                420                 425                 430

Arg Phe Ala Gly Ala Ser Ile Lys Ile Ala Pro Ala Glu Ala Pro Asp
    435                 440                 445

Ala Lys Val Arg Met Val Ile Ile Thr Gly Pro Pro Glu Ala Gln Phe
    450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
                485                 490                 495

Phe Ala Ala Gly Arg Val Ile Gly Lys Gly Gly Lys Thr Val Asn Glu
                500                 505                 510

Leu Gln Asn Leu Ser Ser Ala Glu Val Val Val Pro Arg Asp Gln Thr
                515                 520                 525

Pro Asp Glu Asn Asp Gln Val Val Val Lys Ile Thr Gly His Phe Tyr
    530                 535                 540

Ala Cys Gln Val Ala Gln Arg Lys Ile Gln Glu Ile Leu Thr Gln Val
545                 550                 555                 560

Lys Gln His Gln Gln Gln Lys Ala Leu Gln Ser Gly Pro Pro Gln Ser
                565                 570                 575

Arg Arg Lys

<210> SEQ ID NO 33
<211> LENGTH: 210
<212> TYPE: PRT
<213> ORGANISM: Homo sapiens
```

-continued

```
<400> SEQUENCE: 33

Met Gln Ala Glu Gly Gln Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Arg Gly Gly Ala Pro Arg Gly Pro
    50                  55                  60

His Gly Gly Ala Ala Ser Ala Gln Asp Gly Arg Cys Pro Cys Gly Ala
65                  70                  75                  80

Arg Arg Pro Asp Ser Arg Leu Leu Gln Leu His Ile Thr Met Pro Phe
                85                  90                  95

Ser Ser Pro Met Glu Ala Glu Leu Val Arg Arg Ile Leu Ser Arg Asp
                100                 105                 110

Ala Ala Pro Leu Pro Arg Pro Gly Ala Val Leu Lys Asp Phe Thr Val
            115                 120                 125

Ser Gly Asn Leu Leu Phe Met Ser Val Arg Asp Gln Asp Arg Glu Gly
    130                 135                 140

Ala Gly Arg Met Arg Val Val Gly Trp Gly Leu Gly Ser Ala Ser Pro
145                 150                 155                 160

Glu Gly Gln Lys Ala Arg Asp Leu Arg Thr Pro Lys His Lys Val Ser
                165                 170                 175

Glu Gln Arg Pro Gly Thr Pro Gly Pro Pro Pro Glu Gly Ala Gln
                180                 185                 190

Gly Asp Gly Cys Arg Gly Val Ala Phe Asn Val Met Phe Ser Ala Pro
                195                 200                 205

His Ile
    210

<210> SEQ ID NO 34
<211> LENGTH: 409
<212> TYPE: PRT
<213> ORGANISM: Homo sapiens

<400> SEQUENCE: 34

Met Gln Val Thr Leu Lys Thr Leu Gln Gln Gln Thr Phe Lys Ile Asp
1               5                   10                  15

Ile Asp Pro Glu Glu Thr Val Lys Ala Leu Lys Glu Lys Ile Glu Ser
                20                  25                  30

Glu Lys Gly Lys Asp Ala Phe Pro Val Ala Gly Gln Lys Leu Ile Tyr
            35                  40                  45

Ala Gly Lys Ile Leu Asn Asp Asp Thr Ala Leu Lys Glu Tyr Lys Ile
    50                  55                  60

Asp Glu Lys Asn Phe Val Val Val Met Val Thr Lys Pro Lys Ala Val
65                  70                  75                  80

Ser Thr Pro Ala Pro Ala Thr Thr Gln Gln Ser Ala Pro Ala Ser Thr
                85                  90                  95

Thr Ala Val Thr Ser Ser Thr Thr Thr Thr Val Ala Gln Ala Pro Thr
            100                 105                 110

Pro Val Pro Ala Leu Ala Pro Thr Ser Thr Pro Ala Ser Ile Thr Pro
            115                 120                 125

Ala Ser Ala Thr Ala Ser Ser Glu Pro Ala Pro Ala Ser Ala Ala Lys
    130                 135                 140
```

Gln Glu Lys Pro Ala Glu Lys Pro Ala Glu Thr Pro Val Ala Thr Ser
145                 150                 155                 160

Pro Thr Ala Thr Asp Ser Thr Ser Gly Asp Ser Ser Arg Ser Asn Leu
                165                 170                 175

Phe Glu Asp Ala Thr Ser Ala Leu Val Thr Gly Gln Ser Tyr Glu Asn
                180                 185                 190

Met Val Thr Glu Ile Met Ser Met Gly Tyr Glu Arg Glu Gln Val Ile
                195                 200                 205

Ala Ala Leu Arg Ala Ser Phe Asn Asn Pro Asp Arg Ala Val Glu Tyr
                210                 215                 220

Leu Leu Met Gly Ile Pro Gly Asp Arg Glu Ser Gln Ala Val Val Asp
225                 230                 235                 240

Pro Pro Gln Ala Ala Ser Thr Gly Ala Pro Gln Ser Ser Ala Val Ala
                245                 250                 255

Ala Ala Ala Ala Thr Thr Thr Ala Thr Thr Thr Thr Ser Ser Gly
                260                 265                 270

Gly His Pro Leu Glu Phe Leu Arg Asn Gln Pro Gln Phe Gln Gln Met
                275                 280                 285

Arg Gln Ile Ile Gln Gln Asn Pro Ser Leu Leu Pro Ala Leu Leu Gln
                290                 295                 300

Gln Ile Gly Arg Glu Asn Pro Gln Leu Leu Gln Gln Ile Ser Gln His
305                 310                 315                 320

Gln Glu His Phe Ile Gln Met Leu Asn Glu Pro Val Gln Glu Ala Gly
                325                 330                 335

Gly Gln Gly Gly Gly Gly Gly Gly Gly Ser Gly Gly Ile Ala Glu Ala
                340                 345                 350

Gly Ser Gly His Met Asn Tyr Ile Gln Val Thr Pro Gln Glu Lys Glu
                355                 360                 365

Ala Ile Glu Arg Leu Lys Ala Leu Gly Phe Pro Glu Gly Leu Val Ile
                370                 375                 380

Gln Ala Tyr Phe Ala Cys Glu Lys Asn Glu Asn Leu Ala Ala Asn Phe
385                 390                 395                 400

Leu Leu Gln Gln Asn Phe Asp Glu Asp
                405

<210> SEQ ID NO 35
<211> LENGTH: 208
<212> TYPE: PRT
<213> ORGANISM: Homo sapiens

<400> SEQUENCE: 35

Met Asp Pro Phe Leu Val Leu Leu His Ser Val Ser Ser Ser Leu Ser
1               5               10              15

Ser Ser Glu Leu Thr Glu Leu Lys Phe Leu Cys Leu Gly Arg Val Gly
                20              25              30

Lys Arg Lys Leu Glu Arg Val Gln Ser Gly Leu Asp Leu Phe Ser Met
                35              40              45

Leu Leu Glu Gln Asn Asp Leu Glu Pro Gly His Thr Glu Leu Leu Arg
        50              55              60

Glu Leu Leu Ala Ser Leu Arg Arg His Asp Leu Leu Arg Arg Val Asp
65              70              75              80

Asp Phe Glu Ala Gly Ala Ala Ala Gly Ala Ala Pro Gly Glu Glu Asp
                85              90              95

Leu Cys Ala Ala Phe Asn Val Ile Cys Asp Asn Val Gly Lys Asp Trp
                100             105             110

Arg Arg Leu Ala Arg Gln Leu Lys Val Ser Asp Thr Lys Ile Asp Ser
        115                 120                 125

Ile Glu Asp Arg Tyr Pro Arg Asn Leu Thr Glu Arg Val Arg Glu Ser
        130                 135                 140

Leu Arg Ile Trp Lys Asn Thr Glu Lys Glu Asn Ala Thr Val Ala His
145                 150                 155                 160

Leu Val Gly Ala Leu Arg Ser Cys Gln Met Asn Leu Val Ala Asp Leu
                165                 170                 175

Val Gln Glu Val Gln Gln Ala Arg Asp Leu Gln Asn Arg Ser Gly Ala
                180                 185                 190

Met Ser Pro Met Ser Trp Asn Ser Asp Ala Ser Thr Ser Glu Ala Ser
        195                 200                 205

<210> SEQ ID NO 36
<211> LENGTH: 420
<212> TYPE: PRT
<213> ORGANISM: Homo sapiens

<400> SEQUENCE: 36

Met Ser Ser Pro Arg Asp Phe Arg Ala Glu Pro Val Asn Asp Tyr Glu
1               5                   10                  15

Gly Asn Asp Ser Glu Ala Glu Asp Leu Asn Phe Arg Glu Thr Leu Pro
                20                  25                  30

Ser Ser Ser Gln Glu Asn Thr Pro Arg Ser Lys Val Phe Glu Asn Lys
        35                  40                  45

Val Asn Ser Glu Lys Val Lys Leu Ser Leu Arg Asn Phe Pro His Asn
        50                  55                  60

Asp Tyr Glu Asp Val Phe Glu Glu Pro Ser Glu Ser Gly Ser Asp Pro
65                  70                  75                  80

Ser Met Trp Thr Ala Arg Gly Pro Phe Arg Arg Asp Arg Trp Ser Ser
                85                  90                  95

Glu Asp Glu Glu Ala Ala Gly Pro Ser Gln Ala Leu Ser Pro Leu Leu
                100                 105                 110

Ser Asp Thr Arg Lys Ile Val Ser Glu Gly Glu Leu Asp Gln Leu Ala
        115                 120                 125

Gln Ile Arg Pro Leu Ile Phe Asn Phe His Glu Gln Thr Ala Ile Lys
        130                 135                 140

Asp Cys Leu Lys Ile Leu Glu Glu Lys Thr Ala Ala Tyr Asp Ile Met
145                 150                 155                 160

Gln Glu Phe Met Ala Leu Glu Leu Lys Asn Leu Pro Gly Glu Phe Asn
                165                 170                 175

Ser Gly Asn Gln Pro Ser Asn Arg Glu Lys Asn Arg Tyr Arg Asp Ile
                180                 185                 190

Leu Pro Tyr Asp Ser Thr Arg Val Pro Leu Gly Lys Ser Lys Asp Tyr
        195                 200                 205

Ile Asn Ala Ser Tyr Ile Arg Ile Val Asn Cys Gly Glu Glu Tyr Phe
        210                 215                 220

Tyr Ile Ala Thr Gln Gly Pro Leu Leu Ser Thr Ile Asp Asp Phe Trp
225                 230                 235                 240

Gln Met Val Leu Glu Asn Asn Ser Asn Val Ile Ala Met Ile Thr Arg
                245                 250                 255

Glu Ile Glu Gly Gly Ile Ile Lys Cys Tyr His Tyr Trp Pro Ile Ser
                260                 265                 270

Leu Lys Lys Pro Leu Glu Leu Lys His Phe Arg Val Phe Leu Glu Asn

-continued

```
                275                 280                 285

Tyr Gln Ile Leu Gln Tyr Phe Ile Ile Arg Met Phe Gln Val Val Glu
    290                 295                 300

Lys Ser Thr Gly Thr Ser His Ser Val Lys Gln Leu Gln Phe Thr Lys
305                 310                 315                 320

Trp Pro Asp His Gly Thr Pro Ala Ser Ala Asp Ser Phe Ile Lys Tyr
                325                 330                 335

Ile Arg Tyr Ala Arg Lys Ser His Leu Thr Gly Pro Met Val Val His
                340                 345                 350

Cys Ser Ala Gly Ile Gly Arg Thr Gly Val Phe Leu Cys Val Asp Val
                355                 360                 365

Val Phe Cys Ala Ile Val Lys Asn Cys Ser Phe Asn Ile Met Asp Ile
    370                 375                 380

Val Ala Gln Met Arg Glu Gln Arg Ser Gly Met Val Gln Thr Lys Glu
385                 390                 395                 400

Gln Tyr His Phe Cys Tyr Asp Ile Val Leu Glu Val Leu Arg Lys Leu
                405                 410                 415

Leu Thr Leu Asp
            420

<210> SEQ ID NO 37
<211> LENGTH: 284
<212> TYPE: PRT
<213> ORGANISM: Homo sapiens

<400> SEQUENCE: 37

Met Asp Ala Ile Lys Lys Lys Met Gln Met Leu Lys Leu Asp Lys Glu
1               5                   10                  15

Asn Ala Leu Asp Arg Ala Glu Gln Ala Glu Ala Asp Lys Lys Ala Ala
                20                  25                  30

Glu Asp Arg Ser Lys Gln Leu Glu Asp Glu Leu Val Ser Leu Gln Lys
            35                  40                  45

Lys Leu Lys Gly Thr Glu Asp Glu Leu Asp Lys Tyr Ser Glu Ala Leu
    50                  55                  60

Lys Asp Ala Gln Glu Lys Leu Glu Leu Ala Glu Lys Lys Ala Thr Asp
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
            115                 120                 125

Val Ile Glu Ser Arg Ala Gln Lys Asp Glu Glu Lys Met Glu Ile Gln
    130                 135                 140

Glu Ile Gln Leu Lys Glu Ala Lys His Ile Ala Glu Asp Ala Asp Arg
145                 150                 155                 160

Lys Tyr Glu Glu Val Ala Arg Lys Leu Val Ile Ile Glu Ser Asp Leu
                165                 170                 175

Glu Arg Ala Glu Glu Arg Ala Glu Leu Ser Glu Gly Lys Cys Ala Glu
            180                 185                 190

Leu Glu Glu Glu Leu Lys Thr Val Thr Asn Asn Leu Lys Ser Leu Glu
            195                 200                 205

Ala Gln Ala Glu Lys Tyr Ser Gln Lys Glu Asp Arg Tyr Glu Glu Glu
    210                 215                 220
```

-continued

```
Ile Lys Val Leu Ser Asp Lys Leu Lys Glu Ala Glu Thr Arg Ala Glu
225             230                 235                 240

Phe Ala Glu Arg Ser Val Thr Lys Leu Glu Lys Ser Ile Asp Asp Leu
                245                 250                 255

Glu Asp Glu Leu Tyr Ala Gln Lys Leu Lys Tyr Lys Ala Ile Ser Glu
                260                 265                 270

Glu Leu Asp His Ala Leu Asn Asp Met Thr Ser Ile
            275                 280

<210> SEQ ID NO 38
<211> LENGTH: 180
<212> TYPE: PRT
<213> ORGANISM: Homo sapiens

<400> SEQUENCE: 38

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Gly Ala Pro Arg Gly Pro
        50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
                115                 120                 125

Ser Gly Asn Ile Leu Thr Ile Arg Leu Thr Ala Ala Asp His Arg Gln
            130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180
```